(12) United States Patent
Gluckman et al.

(10) Patent No.: US 7,605,177 B2
(45) Date of Patent: *Oct. 20, 2009

(54) EFFECTS OF GLYCYL-2 METHYL PROLYL GLUTAMATE ON NEURODEGENERATION

(75) Inventors: Peter David Gluckman, Auckland (NZ); Gregory Brian Thomas, Western Australia (AU); Jian Guan, Auckland (NZ); Michael Dragunow, Auckland (NZ); Ashmit Kumar Anand, Auckland (NZ); Frank Sieg, Auckland (NZ); Margaret Anne Brimble, Auckland (NZ)

(73) Assignee: Neuren Pharmaceuticals Limited, Auckland (NL)

( * ) Notice: Subject to any disclaimer, the term of this patent is extended or adjusted under 35 U.S.C. 154(b) by 115 days.

This patent is subject to a terminal disclaimer.

(21) Appl. No.: 11/314,424

(22) Filed: Dec. 20, 2005

(65) Prior Publication Data

US 2007/0298009 A1 Dec. 27, 2007

Related U.S. Application Data

(63) Continuation-in-part of application No. 10/155,864, filed on May 24, 2002, now Pat. No. 7,041,314.

(60) Provisional application No. 60/293,853, filed on May 24, 2001.

(51) Int. Cl.
*A61K 31/401* (2006.01)
*C07D 207/16* (2006.01)

(52) U.S. Cl. .................................................. 514/423

(58) Field of Classification Search ................ 424/451, 424/464; 548/537; 514/423
See application file for complete search history.

(56) References Cited

U.S. PATENT DOCUMENTS

| | | | |
|---|---|---|---|
| 4,444,879 A | 4/1984 | Foster et al. | |
| 4,511,390 A | 4/1985 | Kauer et al. | |
| 4,699,875 A | 10/1987 | Appel et al. | |
| 4,783,524 A | 11/1988 | Larsen et al. | |
| 4,906,614 A | 3/1990 | Giertz et al. | |
| 5,068,224 A | 11/1991 | Fryklund et al. | |
| 5,089,406 A | 2/1992 | Williams et al. | |
| 5,093,317 A | 3/1992 | Lewis et al. .................. | 514/12 |
| 5,106,832 A | 4/1992 | Froesch et al. | |
| 5,114,840 A | 5/1992 | Tryggvason et al. | |
| 5,149,657 A | 9/1992 | Maugh et al. | |
| 5,243,038 A | 9/1993 | Ferrari et al. | |
| 5,273,961 A | 12/1993 | Clark et al. | |
| 5,420,112 A | 5/1995 | Lewis et al. | |
| 5,451,660 A | 9/1995 | Builder et al. | |
| 5,496,712 A | 3/1996 | Cappello et al. | |
| 5,635,604 A | 6/1997 | Dalboge et al. | |
| 5,639,729 A | 6/1997 | Goldstein et al. | |
| 5,648,335 A | 7/1997 | Lewis et al. | |
| 5,670,616 A | 9/1997 | Weber | |
| 5,679,552 A | 10/1997 | Dalboge et al. | |
| 5,686,423 A | 11/1997 | Wang et al. | |
| 5,691,169 A | 11/1997 | Dalboge et al. | |
| 5,703,045 A | 12/1997 | Lewis et al. | |
| 5,710,252 A | 1/1998 | Weber et al. | |
| 5,714,460 A | 2/1998 | Gluckman et al. | |
| 5,750,376 A | 5/1998 | Weiss et al. | |
| 5,801,045 A | 9/1998 | Weber et al. | |
| 5,804,550 A | 9/1998 | Bourguignon et al. | |
| 5,804,563 A | 9/1998 | Still et al. | |
| 5,861,373 A | 1/1999 | Gluckman et al. | |
| 5,965,531 A | 10/1999 | Webster et al. .................. | 514/12 |
| 6,054,579 A | 4/2000 | Harriman ..................... | 540/200 |
| 6,187,906 B1 | 2/2001 | Gluckman et al. .......... | 530/331 |
| 6,294,585 B1 | 9/2001 | Brown | |
| 6,342,585 B1 | 1/2002 | Grossmann | |
| 6,365,573 B1 | 4/2002 | Gluckman et al. ............ | 514/18 |
| 6,444,657 B1 | 9/2002 | Slusher et al. | |
| 2001/0018199 A1 | 8/2001 | Dalboge et al. | |
| 2002/0013277 A1 | 1/2002 | Gluckman et al. | |
| 2002/0035066 A1 | 3/2002 | Gluckman et al. | |
| 2002/0115594 A1 | 8/2002 | Bourguignon | |
| 2002/0177239 A1 | 11/2002 | Thomas et al. | |
| 2003/0027755 A1 | 2/2003 | Guan et al. | |
| 2003/0211990 A1 | 11/2003 | Sieg et al. | |

FOREIGN PATENT DOCUMENTS

| | | |
|---|---|---|
| EP | 86850417.6 | 12/1986 |
| EP | 227619 | 1/1987 |
| EP | 0 289 314 | 2/1988 |
| EP | 289314 | 2/1988 |
| EP | 88303855.6 | 4/1988 |
| EP | 8850306.7 | 9/1988 |
| EP | 308386 | 3/1989 |
| EP | 0366 638 A2 | 5/1990 |
| EP | 366638 | 5/1990 |
| EP | 0 357 240 B1 | 1/1993 |
| EP | 357240 | 1/1993 |
| EP | 1043027 | 11/2000 |
| EP | 1043027 A1 | 11/2000 |
| FR | 2 707 170 | 1/1995 |

(Continued)

OTHER PUBLICATIONS

Anthony J. Williams, et al., "Characterization of a New Rat Model of Penetrating Ballistic Brain Injury", Jnl. of Neurotrauma, MD, vol. 22, No. 2, 2005, pp. 314-332.

(Continued)

*Primary Examiner*—Rebecca L Anderson
(74) *Attorney, Agent, or Firm*—D. Benjamin Borson

(57) ABSTRACT

This invention provides analogs and peptidomimetics of glycyl-L-prolyl-L-glutamic acid (GPE). In particular, this invention relates to GPE analogs and peptidomimetics that are anti-apoptotic, anti-necrotic and have neuroprotective effects. These agents are useful in treating neurodegeneration and behavioural disorders caused by toxins, traumatic brain injury and autoimmune disorders of the brain, such as multiple sclerosis and in reducing seizures.

13 Claims, 30 Drawing Sheets

FOREIGN PATENT DOCUMENTS

| FR | 270717 | 1/1995 |
|---|---|---|
| WO | WO 88/03533 | 5/1988 |
| WO | WO 88/08848 | 11/1988 |
| WO | WO 88/09171 | 12/1988 |
| WO | WO 89/01343 | 2/1989 |
| WO | WO 89/05822 | 6/1989 |
| WO | WO 90/05177 | 5/1990 |
| WO | WO 92/09695 | 6/1992 |
| WO | WO 93/02695 | 2/1993 |
| WO | WO93/08826 | 5/1993 |
| WO | WO 93/08826 | 5/1993 |
| WO | WO 93/08828 | 5/1993 |
| WO | WO 93/10806 | 6/1993 |
| WO | WO 93/20836 | 10/1993 |
| WO | WO 93/21216 | 10/1993 |
| WO | WO 94/23754 | 10/1994 |
| WO | WO 94/26301 | 11/1994 |
| WO | PCT/NZ 94/00143 | 12/1994 |
| WO | WO 94/00143 | 12/1994 |
| WO | WO 95/13823 | 5/1995 |
| WO | WO 95/17204 | 6/1995 |
| WO | WO 97/17090 | 5/1997 |
| WO | WO 97/39032 | 10/1997 |
| WO | WO 97/47735 | 12/1997 |
| WO | WO 98/14202 | 4/1998 |
| WO | WO 98/52620 | 11/1998 |
| WO | WO 99/08702 | 2/1999 |
| WO | WO 99/15192 | 4/1999 |
| WO | WO 99 15192 A | 4/1999 |
| WO | WO 99/39210 | 8/1999 |
| WO | WO 99/65509 | 12/1999 |
| WO | WO 00/13650 | 3/2000 |
| WO | WO 02/16408 | 2/2002 |
| WO | WO 02/094856 | 11/2002 |

OTHER PUBLICATIONS

Jed a. Hartings, et al, "Occurrence of nonconclusive seizures, periodic epileptiform discharges, and intermittent rhythmic delta activity in rat *Focal ischemia*", Experimental Neurology 179 (2003) pp. 139-149.

P.M. Vespa, MD, et al., "Acute seizures after intracerebral hemorrhage—A factor in progressive midline shift and outcome", Division of Neurosurgery, Department of Neurology, UCLA Stroke Center, Jan. 20, 2003, pp. 1441-1446.

Michael Privitera, et al., "EEG detection of nontonic-clonic status epilepticus in patients with altered consciousness", Department of Neurology, University of Cincinnati Medical Center, Feb. 16, 1994, pp. 155-166.

Paul M. Vespa, M.D., et al., "Increased incidence and impact of nonconvulsive and convulsive seizures after traumatic brain injury as detected by continuous electroencephalographic monitoring", J. Neurosurg vol. 91:750-760, 1999.

Lu, X.-C, A Glypromate Analog, NNZ-2566, is Neuroprotective in Rats Subjected to Penetrating Ballistic-Like Brain Injury (PBBI), Div. Psychiatry and Neuroscience, Walter Reed.

Army Institute of Research, Silver Spring, MD, 20910, Journal of Neurotrauma, vol. 10 (#22), p. 1255, Oct. 2005.

Notification of Transmittal of The International Search Report and The Written Opinion of the International Searching Authority; International Bureau dated Apr. 24, 2007 in International Application No. PCT/US06/19909.

Lucas, M.D., D. R., et. al., "The Toxic Effect of Sodium $_L$-Glutamate on the Inner Layers of the Retina", *Archives of Opthamology*, 58, 1957, pp. 198-204.

Curtis, David R., et. al., "Amino Acid Transmitters in the Mammalian Central Nervous System", *Ergebnisse der Physiologie*, 69, 1974, pp. 97-188.

Bauer, Carl-Axel, "Active Centers of α-Chymotrypsin and of *Streptomyces griseus* Proteases 1 and 3," Department of Biochemistry, University of Lund, Nov. 5, 1979, pp. 565-570.

Carone, R.A. et al., "Differences Between in vitro and in vivo Degradation of LHRH by Rat Brain and Other Organs," *American Journal of Physiology*, 253, 1987, E317-E321.

Szabo, Laszlo, et. al., "The Bovine Insulin-like Growth Factor (IGF) Binding Protein Purified from Conditioned Medium Requires the N-Terminal Tripeptide in IGF-1 for Binding," *Biochemical and Biophysical Research Communications*, vol. 151, No. 1, Feb. 29, 1988, pp. 207-214.

Shepard, M.D., Gordon M.,"Neurotransmitters and Neuromodulators," Neurobiology, 2nd edition, 1988, pp. 145-176.

Sakaki, Atsushi, et al., "Multiple Forms of Immunoreative Growth Hormone-Releasing Hormone in Human Plasma, Hypothalamus, and Tumor Tissues," Journal of Clinical Endocrinology and Metabolism, vol. 68, No. 1, 1989, pp. 180-185.

Bourguignon, Jean-Pierre, et. al., "Pulsatile Release of Gonadortropin-Releasing Hormone from Hypothalamic Explants is Restrained by Blockade of $N$-Methyl-$_{D,L}$-Aspartate Receptors," Endocrinology, vol. 125, No. 2, 1989, pp. 1090-1096.

Sara, Vicki R., et. al., "Identification of Gly-Pro-Glu (GPE), the Aminoterminal Tripeptide of Insulin-like Growth Factor 1 Which is Truncated in Brain, as a Novel Neuroactive Peptide," Biochemical and Biophysical Research Communications, Vol. 165, No. 2, Dec. 15, 1989, pp. 766-771.

Donoso, Alfredo O., et. al., "Glutamate Receptors of the Non-$N$-Methyl-$_D$-Aspartic Acid Type Mediate the Increase in Luteinizing Hormone-Releasing Hormone Release by Excitatory Amino Acids in Vitro", *Endocrinology*, vol. 126, No. 1, 1990, pp. 414-420.

Bourguignon, Jean-Pierre, et. al., "Maturation of the Hypothalamic Control of Pulsatile Gonadotropin-Releasing Hormone Secretion at Onset of Puberty: II. Reduced Potency of an Inhibitory Autofeedback," *Endocrinology*, vol. 127, No. 6, 1990, pp. 2884-2890.

Challis, Brian C., et al., "Synthesis and Characterisation of Some New $N$-Nitrosodipeptides," J. Chemistry Society Perkin Trans., 1990, pp. 3103-3108.

Sara, Vicki R., et al., "Neuroactive Products of IGF-1 and IGF-2 Gene Expression in the CNS,"*Molecular Biology and Physiology of Insulin and Insulin-Like Growth Factors*New York, 1991, pp. 439-448.

Hiney, Jill K., et al., "Insulin-Like Growth Factor I: A Possible Metabolic Signal Involved in the Regulation of Female Puberty," *Neuroendocrinology*, 54, 1991, pp. 420-423.

Bourguignon, Jean-Pierre, et. al., "Gonadal-Independent Developmental Changes in Activation of $N$-Methyl-D-Aspartate Receptors Involved in Gonadotropin-Releasing Hormone Secretion," *Neuroendocrinology*, 55, 1992, pp. 634-641.

Guan, Jian, et. al., "The Effects of IGF-1 Treatment After Hypoxic-Ischemic Brain Injury in Adult Rats," *J Cereb Blood Flow Metab*, vol. 13, No. 4, 1993, pp. 609-616.

Nilsson-Hakansson, Lena, et al., "The Effects of IGF-1, Truncated IGF-1 and the Tripeptide Gly-Pro-Glu on Acetylcholine Release from Parietal Cortex of Rat Brain," *NeuroReport*, vol. 4, No. 9, Aug. 6, 1993, pp. 1111-1114.

Di Blasio,B., et al. "β-Alanine Containing Peptides: γ-Turns in Cyclotetrapeptides," Research Center on Bioactive Peptides, Napoli, Italy, *Biopolymers*, vol. 33, 1993, pp. 621-631.

Sara, Vicki R., et. al., "The Biological Role of Truncated Insulin-like Growth Factor-1 and the Tripeptide GPE in the Central Nervous System," *Annals of the New York Academy of Sciences*, 692, 1993, pp. 183-191.

Bourguignon, Jean-Pierre et. al., "Gonadotropin Releasing Hormone Inhibitory Autofeedback by Subproducts Antagonist at $N$-Methly-D-Aspartate Receptors: A Model of Autocrine Regulation of Peptide Scretion," The Endocrine Society, vol. 134, No. 3, 1994, pp. 1589-1592. The Endocrine Society, vol. 132, No. 3, 1994, pp. 1589- 1592.

Saura, J. et al., "Neuroprotective Effects of Gly-Pro-Glu, the N-terminal Tripeptide of IGF-1, in the Hippocampus in vitro," *NeuroReport*, vol. 10, No. 1, Jan. 1999, pp. 161-164.

Néel, J., "Experimental Study of the Influence of Specific Intramolecular Interactions on the Conformation of Model Molecules (Peptides and Oligopetides)," Lagoratoire de Chimie-Physique Macromolecular, pp. 201-225.

Hanusch-Kompa and Ivar Ugi, "Multi-Component Reactions 13: Synthesis of γ-Lactams as Part of a Multi-Ring System Via Ugi-4-

Centre-3-Component Reaction," Technische Universität München, Tetrahedron Letters 39, 1998, pp. 2725-2728.

Mewar, Reema, "Expression of Insulin-Like Growth Factor-Binding Protein Messenger RNAs in Developing Rat Oligodendrocytes and Astrocytes", Journal of Neuroscience, 50:721-728 (1997).

Goddard, Diane, "In Vivo Actions of Fibroblast Growth Factor-2 and Insuling-Like Growth Factor-1 on Oligodendrocyte Development and Myelination in the Central Nervous System", Journal of Neuroscience Research 57:74-85 (1999).

Komoly, Samuel, "Insulin-like Growth Factor I Gene Expression is Induced in Astrocytes During Experimental Demyelination", Proc. Natl. Acad. Sci., vol. 89, pp. 1894-1898, Mar. 1992.

Yamaguchi, F., "Increase of Extracellular Insulin-like Growth Factor I (IGF-I) Concentration Following Electrolytical Lesion in Rat Hippocampus", Neuroscience Letters, 128, 273-276, (1991).

Hinks, G.L., "Distinctive Patterns of PDGF-A, FGF-2, IGF-1, and TGF βGene Expression During Remyelination of Experimentally-Induced Spinal Cord Demyelination", Molecular and Cellular Neuroscience 14, 153-168 (1999).

Kiess, Wieland, "Rat C6 Glial Cells Synthesize Insulin-Like Growth Factor I(IGF-I) and Express IGF-I Receptors and IGF-II/Mannose 6-Phosphate Receptors", Endocrinology, vol. 124, 1727-1736, (1989).

Ye, P. "Insulin-Like Growth Factor I Protects Olilgodendrocytes From Tumor Necrosis Factor-α-Inducted Injury", Endocrinology, vol. 140, No. 7, 3063-3072, (1999).

Gluckman, Peter, "A Role for IGF-1 in the Rescue of CNS Neurons Following Hypoxic-Ischemic Injury", Biochemical and Biophysical Research Communications, vol. 182, No. 2, pp. 593-599, (1992).

Wilcazk, N. "Insulin-like growth Factor-I Receptors in Normal Appearing White Matter and Chronic Plaques in Multiple Sclerosis", Brain Research, 772, pp. 243-246, 1997.

Lee, Wei-Hua, "Insulin-like Growth Factors and Cerebral Ischemia", Annals New York Academy of Sciences, 28;679:418-22 (May 1993).

Compston, A., "Treatment and management of multiple sclerosis", Chapter 14, McAlpin's Multiple Sclerosis, Third Edition, Churchill Livingstone, London, 1988.

Sara, Vicki R., et. al., "The Biological Role of Truncated Insulin-like Growth Factor-1 and the Tripeptide GPE in the Central Nervous System", Annals of the New York Academy of Sciences, 692, 1993, 183-191.

Bourguignon, Jean-Pierre., et. al., "Pulsatile Release of Gonadortropin-Releasing Hormone from Hypothalamic Explants is Restrained by Blockade of $N$-Methyl-$_{D,L}$-Aspartate Receptors", Endocrinology, vol. 125, No. 2, 1989, 1090-1096.

Bourguignon, Jean-Pierre, et. al., "Glutamate Receptors of the Non-$N$-Methyl-D-Aspartic Acid Type Mediate the Increase in Luteinizing Hormone-Releasing Hormone Release by Excitatory Amino Acids in Vitro", Endocrinology, Vol. 126, No. 1, 1990, 414-420.

Bourguignon, Jean-Pierre, et. al., "Maturation of the Hypothalamic Control of Pulsatile Gonadotropin-Releasing Hormone Secretion at Onset of Puberty: II. Reduced Potency of an Inhibitory Autofeedback", Endocrinology, vol. 127, No. 6, 1990, 2884-2890. (1990).

Guan, Jian, et. al., "The Effects of IGF-1 Treatment After Hypoxic-Ischemic Brain Injury in Adult Rats", J Cereb Blood Flow Metab, vol. 13, No. 4, 1993, 609-616.

Nilsson-Hakansson, Lena, et. al., "Effects of IGF-1, truncated IGF-1 and the tripeptide Gly-Pro-Glu on acetylcholine release from parietal cortex of rat brain", NeuroReport, vol. 4, No. 9, Aug. 1993 (Sep. Issue), 1111-1114.

Sara, Vicki R., et. al., "Identification of Gly-Pro-Glu (GPE), the Aminoterminal tripeptide of insulin-like growth factor 1 which is truncated in brain, as a novel neuroactive peptide", Biochemical and Biophysical Research Communications, vol. 165. No. 2, Dec. 15, 1989, 766-771.

Bourguignon, Jean-Pierre, et. al., "Gonadal-Independent Developmental Changes in Activation of $N$-Methyl-D-Aspartate Receptors Involved in Gonadotropin-Releasing Hormone Secretion", Neuroendocrinology, 55, 1992, 634-641.

Hiney, Jill K., et. al., Insulin-Like Growth Factor I: A Possible Metabolic Signal Involved in the Regulation of Female Puberty, Neuroendocrinology, 54, 1991, 420-423.1001US2.

Szabo, Laszlo, et. al., The Bovine Insulin-like Growth Factor (IGF) binding protein purified from conditioned medium requires the N-Terminal Tripeptide in IGF-1 for binding, Biochemical and Biophysical Research Communications, vol. 151, No. 1, Feb. 29, 1988, 207-214.

Lucas, M.D., D. R., et. al., "The Toxic Effect of Sodium $_L$-Glutamate on the Inner Layers of the Retina", Archives of Opthamology, 58, 1957, 198-204.

Shepard, M.D., Gordon M.,"Neurotransmitters and Neuromodulators", Neurobiology, 2$^{nd}$ edition, 1988, 145-176.

Sara, V. R. et al.: "The Biological Role of Truncated Insulin-Like Growth Factor-1 and The Tripeptide GPE in The Central Nervous System", Annals of the New York Academy of Sciences, vol. 692, pp. 183-191, (1991).

Curtis, David R., et. al., "Amino Acid Transmitters in the Mammalian Central Nervous System", Ergebnisse der Physiologie, 69, 1974, 97-188.

Hiney, Jill K., et. al., Insulin-Like Growth Factor I: A Possible Metabolic Signal Involved in the Regulation of Female Puberty, Neuroendocrinology, 54, 1991, 420-423.1001US2;.

Bourguignon, Jean-Pierre, et. al., "Gonadal-Independent Developmental Changes in Activation of N-Methyl-DAspartate Receptors Involved in Gonadotropin-Releasing Hormone Secretion", Neuroendocrinology, 55, 1992, 634-641.

Sara, Vicki R., et. al., "Identification of Gly-Pro-Glu (GPE), the Aminoterminal tripeptide of insulin-like growth factor 1 which is truncated in brain, as a novel neuroactive peptide", Biochemical and Biophysical Research Communications, vol. 165. No. 2, Dec. 15, 1989, 766-771.

McCafferty, John, et al., "Phage antibodies: filamentous phage displaying antibody variable domains", Nature vol. 348, Dec. 6, 1990 p. 552-554.

Hanes, Jozef, et al., "In vitro selection and evolution of functional proteins by using ribosome display", Proc. Natl. Acad. Sci., USA, vol. 94, pp. 4937-4942, May 1997.

Crameria, Reto and Suter, Mark, "Display of biologically active proteins on the surface of filamentous phages: a cDNA cloning system for selection of functional gene products linked to the genetic information responsible for their production", Gene, (1993) pp. 69-75.

Luft, Benjamin J., "The 93-Kilodalton Protein of Borrelia burgodorferi: an Immunodominant Protoplasmic Cylinder Antigen", Infection and Immunity, pp. 4309-4320, Oct. 1992.

Liu, Bin et al, "Applying Phage Antibodies to Proteomics: Selecting Single Chain Fv Antibodies to Antigens Blotted on Nitrocellulose", Analytical Biochemistry 286, pp. 119-128 (2000).

Sorensen, Anne L., "Purification and Characterization of a Low-Molecular-Mass T-Cell antigen Secreted by Mycobacterium tuberculosis", Infection and Immunity pp. 1710-1717, May 1995.

Little, Melvyn, "Generation of a large complex antibody library from multiple donors", Journal of Immunological Methods 231, p. 3-9, (1999).

Schaffitzel, Christiane, "Ribosome display: an in vitro method for selection and evolution of antibodies from libraries", Journal of Immunological Methods 231, p. 119-135, (1999).

Mewar, Reema, "Expression of Insulin-Like Growth Factor-Binding Protein Messenger RNAs in Developing Rat Oligodendrocytes and Astrocytes", Journal of Neuroscience, 50:721-728 (1997).

Goddard, Diane, "In Vivo Actions of Fibroblast Growth Factor-2 and Insuling-Like Growth Factor-1 on Oligodendrocyte Development and Myelination in the Central Nervous System", Journal of Neuroscience Research 57:74-85 (1999).

Komoly, Samuel, "Insulin-like Growth Factor I Gene Expression is Induced in Astrocytes During Experimental Demyelination", Proc. Natl. Acad. Sci., vol. 89, pp. 1894-1898, Mar. 1992.

Yamaguchi, F., "Increase of Extracellular Insulin-like Growth Factor I (IGF-I) Concentration Following Electrolytical Lesion in Rat Hippocampus", Neuroscience Letters, 128, 273-276, (1991).

Hinks, G.L., "Distinctive Patterns of PDGF-A, FGF-2, IGF-1, and TGFβ. Gene Expression During Remyelination of Experimentally-Induced Spinal Cord Demyelination", Molecular and Cellular Neuroscience 14, 153-168 (1999).

Kiess, Wieland, "Rat C6 Glial Cells Synthesize Insulin-Like Growth Factor I(IGF-I) and Express IGF-I Receptors and IGF-II/Mannose 6-Phosphate Receptors", Endocrinology, vol. 124, 1727-1736, (1989).

Ye, P. "Insulin-Like Growth Factor I Protects Olilgodendrocytes From Tumor Necrosis Factor-α-Inducted Injury", Endocrinology, vol. 140, No. 7, 3063-3072, (1999).

Gluckman, Peter, "A Role for IGF-1 In The Rescue of CNS Neurons Following Hypoxic-Ischemic Injury", Biochemical and Biophysical Research Communications, vol. 182, No. 2, pp. 593-599, (1992).

Wilcazk, N. "Insulin-like growth Factor-I Receptors in Normal Appearing White Matter and Chronic Plaques in Multiple Sclerosis", Brain Research, 772, pp. 243-246, 1997.

Lee, Wei-Hua, "Insulin-like Growth Factors and Cerebral Ischemia", Annals New York Academy of Sciences, 28;679:418-22 (May 1993).

Compston, A., "Treatment and management of multiple sclerosis", Chapter 14, McAlpin's Multiple Sclerosis, Third Edition, Churchill Livingstone, London, 1988.

Guan, Jian et al., "Insulin-like Growth Factor-1 Reduces Postischemic White Matter Injury in Fetal Sheep", Journal of Cerebral Blood Flow and Metabolism vol. 21, No. 5, May 2001 pp. 493-50.

Yao Da-Lin, et al. "Insulin-like growth factor I treatment reduces demyelination and up-regulates gene expression of myelin-related proteins in experimental autoimmune encephalomyelitis", Proceedings of the National Academy of Sciences of the United States, vol. 92, No. 13, 1995, pp. 6190-6194, 1995.

Ballard, F.J., et al., "DS(1-3) IGF-I: A Truncated Form of Insulin-Like Growth Factor-I," *International Journal of Biochemistry and Cell Biology*, Exeter, Great Britain, vol. 28, No. 10, 1996, pp. 1085-1087.

Saura, J. et al. Neuroprotective effects of Gly-Pro-Glu, the N-terminal tripeptide of IGF-1, in the hippocampus in vitro. NeuroReport. 1999, vol. 10, pp. 161-164.

Nilsson-Hakansson et al. Effects of 1GF-1, truncated IGF-1 and the tripeptide Gly-Pro-Glu on acetylcholine relese from parietal cortex of rat brain. NeuroReport. Aug. 6, 1993, vol. 4, No. 9, pp. 1111-1114.

Sara, et al., Identification of Gly-Pro-Glu (GPE), the aminoterminal tripeptide of insulin-like growth factor 1 whihc is truncated in brain, as a novel neuroactive peptide. *Biochemical and Biophysical Research Communications*, Dec. 15, 1989, vol. 165, No. 2, pp. 766-771.

Ballard, F.J., et al., "Des (1-3) Igf-I: a truncated form of insuling-like growth factor-I", Int. J. Biochem. Cell Biol. 1996, vol. 28, No. 10, pp. 1085-1087.

Hanusch-Kompa, et al., *Multi-Component Reactions 13: Synthesis of y-Lactams as Part of a Multi-Ring System via Ugi-4-Centre-3-Component Reactions*, Tetrahedron Letters, 39 (1998) pp. 2725-2728.

Wu, Dahao David et al: "Expression of the activin axis and neuronal rescue effects of recombinant activin A following hypoxic-ischemic brain injury in the infant rat", Brain Research, vol. 835, No. 2, Jul. 24, 1999, pp. 369-378.

Hughes P. E et al: "Administration of recombinant human activin-A has powerful neurotrophic effects on select striatal phenotypes in the quinolinic acid lesion model of Huntington's disease." Neuroscience, vol. 92, No. 1, May 20, 1999, pp. 197-209.

Tretter Yvonne P. et al: "Induction of activin A is essential for the neuroprotective action of basic fibroblast growth factor in vivo." Nature Medicine, vol. 6, No. 7, Jul. 2000, pp. 812-815.

Hughes Paul e et al: "Activity and injury-dependent expression of inducible transcription factors, growth factors and apoptosis-related genes within the central nervous system." Progress in Neurobiology (Oxford), vol. 57, No. 4, Feb. 1999, pp. 421-450.

Di Loreto S et al: "Interleukin 1-beta modulates the effects of hypoxia in neuronal culture." Journal of Neuroimmunology, vol. 106, No. 1-2, Jul. 1, 2000, pp. 32-42.

Costantini Lauren C et al: "Immunophilin ligands can prevent progressive dopaminergic degeneration in animal models of Parkinson's disease." European Journal of Neuroscience, vol. 13, No. 6, Mar. 2001, pp. 1085-1092.

Sharkey J. et al., "Calcineurin Inhibitors As Neuroprotectants Focs of Tacrolimus and Cyclosporin" CNS Drugs, Adis, International, Auckland<NZ, vol. 13, No. 1, Jan. 2000, pp. 1-13.

Yang, Shao-Hua et al., "Estradiol exerts neuroprotective effects when administered after ischemic insult." Stroke, vol. 31, No. 3 Mar. 2000, pp. 745-750.

I. MODIFY GLYCINE RESIDUE

G*PE

II. MODIFY GLUTAMIC ACID RESIDUE

GPE* i. α-carboxylic acid residue
ii. γ-carboxylic acid residue
iii. GPE diesters

III. MODIFY PEPTIDE LINKAGES

GP*E and GPE# i. modify Pro - α-methylproline
ii. modify Glu - N-Methylglutamic acid
    α-Methylglutamic acid

*γ-carboxylic acid - modify to an amide*

*synthesis of amide*

EFFECTS OF GLYCYL-2 METHYL PROLYL GLUTAMATE ON NEURODEGENERATION

CLAIM OF PRIORITY

This application is a continuation in part of application Ser. No. 10/155,864, filed May 24, 2002, now U.S. Pat. No. 7,041,314, which claims priority under 35 U.S.C. 119(e) to U.S Provisional Application No. 60/293,853, filed May 24, 2001. Both of the above applications are expressly incorporated herein by reference as if separately so incorporated.

BACKGROUND

1. Field of the Invention

This invention relates to analogs and peptidomimetics of glycyl-L-prolyl-L-glutamic acid (GPE). In particular, this invention relates to GPE analogs and peptidomimetics that are anti-apoptotic and anti-necrotic neuroprotective, to methods of making them, to pharmaceutical compositions containing them, and to their use in treating neurological disorders.

2. Description of Related Art

EP 0 366 638 discloses GPE (a tri-peptide consisting of the amino acids Gly-Pro-Glu) and its di-peptide derivatives Gly-Pro and Pro-Glu. EP 0 366 638 discloses that GPE is effective as a neuromodulator and is able to affect the electrical properties of neurons.

WO95/172904 discloses that GPE has neuroprotective properties and that administration of GPE can reduce damage to the central nervous system (CNS) by the prevention or inhibition of neuronal and glial cell death.

WO 98/14202 discloses that administration of GPE can increase the effective amount of choline acetyltransferase (ChAT), glutamic acid decarboxylase (GAD), and nitric oxide synthase (NOS) in the central nervous system (CNS).

WO99/65509 discloses that increasing the effective amount of GPE in the CNS, such as by administration of GPE, can increase the effective amount of tyrosine hydroxylase (TH) in the CNS in order to increase TH-mediated dopamine production in the treatment of diseases such as Parkinson's disease.

WO02/16408 discloses GPE analogs capable of inducing a physiological effect equivalent to GPE within a patient. The applications of the GPE analogs include the treatment of acute brain injury and neurodegenerative diseases, including but not limited to, injury or disease in the CNS.

The disclosures of these and other documents referred to in this application (including in the Figures) are expressly incorporated herein by reference as if each one was individually incorporated by reference.

SUMMARY

In its first aspect, this invention provides compounds of Formula 1 and Formula 2: where:

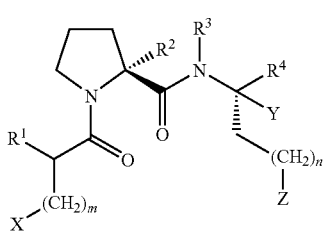

Formula 1

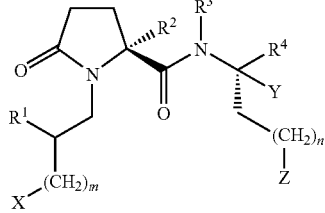

Formula 2 m is 0 or 1;
n is 0 or 1;
X is H or $-NR^6R^7$;
Y is H, alkyl, $-CO_2R^5$, or $-CONR^6R^7$;
Z is H, alkyl, $-CO_2R^5$ or $-CONR^6R^7$;
$R^1$ is H, alkyl, or aralkyl;
$R^2$, $R^3$, and $R^4$ are independently H or alkyl;
each $R^5$ is independently H, alkyl, or a fatty alcohol residue;
each $R^6$ and $R^7$ is independently H, alkyl, or aralkyl, or $-NR^6R^7$ is pyrrolidino, piperidino, or morpholino;
or a lactone formed when a compound where Y is $-CO_2$(alkyl) and Z is $-CO_2H$ or where
Y is $-CO_2H$ and Z is $-CO_2$(alkyl) is lactonized;
and the pharmaceutically acceptable salts thereof,
provided that the compound is not GPE, N-Me-GPE, GPE amide, APE, GPQ or a salt thereof.

In yet another aspect, this invention provides pharmaceutical compositions comprising a pharmaceutically acceptable excipient and a therapeutically effective amount of at least one compound of this invention. These compositions find use as anti-apoptotic agents, anti-necrotic agents, anti-neurodegenerative agents, are useful for conditions where use of an anti-neurodegenerative agent is indicated.

In another aspect, this invention provides a method of treating an animal having a disease or injury capable of treatment by administration of a GPE analog or peptidomimetic, comprising administration to that animal of at least one compound of this invention, optionally in conjunction with at least one other conventional therapeutic agent for the disease being treated. Compositions of this invention can be effective in treating neurodegeneration caused by hypoxic-ischemic injury, hemorrhagic stroke, non-hemorrhagic stroke, penetrating brain injury and chronic neurodegenerative disorders including Alzheimer's disease, Parkinson's disease, Huntington's disease, neuropathy caused by type I or type II diabetes (diabetic neuropathies), autoimmune disorders of the brain and multiple sclerosis.

In a further aspect, this invention provides methods of preparing the compounds of the first aspect of this invention.

BRIEF DESCRIPTION OF THE DRAWINGS

This invention is described with reference to specific embodiments thereof. Other aspects and features of this invention can be understood with reference to the Figures, in which:

FIG. 12 depicts a graph showing effects of GPE on cortical neurons injured with okadaic acid.

FIG. 13 depicts a graph showing effects of G-2MePE on cortical neurons injured with okadaic acid.

FIG. 14 depicts a graph showing effects of G-2MePE, GPE on cerebellar microexplants injured with okadaic acid.

FIG. 15 depicts a graph showing effects of G-2MePE or GPE on striatal cells injured with okadaic acid.

FIG. 16A depicts a graph of neural damage scores in animals treated with vehicle or G-2MePE. A highly significant reduction (overall $P<0.0001$) in the tissue damage in the injured right hemisphere when compared with the saline control group was observed (FIG. 16B).

DETAILED DESCRIPTION

Definitions

Figure 1:
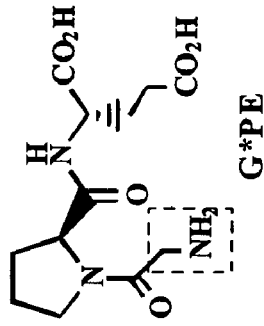
FIG. 1 is a general scheme for preparation of synthetic analogues of GPE of the invention.
Figure 1:
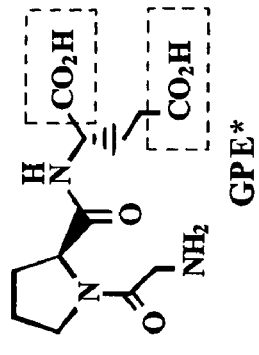
Figure 1:
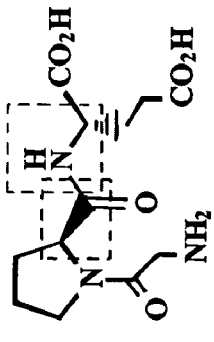

The term "about" with reference to a dosage or time refers to a particular variable and a range around that variable that is within normal measurement error or is within about 20% of the value of the variable.

The term "alkyl" means a linear saturated hydrocarbyl group having from one to six carbon atoms, or a branched or cyclic saturated hydrocarbyl group having from three to six carbon atoms. Exemplary alkyl groups include straight and branched chain, or cyclic alkyl groups, methyl, ethyl, isopropyl, cyclopropyl, tert-butyl, cyclopropylmethyl, and hexyl.

The term "animal" includes humans and non-human animals, such as domestic animals (cats, dogs, and the like) and farm animals (cattle, horses, sheep, goats, swine, and the like).

The term "aralkyl" means a group of the formula —$CH_2)_{1-2}$Ar, where Ar is a 5- or 6-membered carbocyclic or heterocyclic aromatic ring, optionally substituted with 1 to 3 substituents selected from Cl, Br, —OH, —O-alkyl, —$CO_2R^8$ (where $R^8$ is H or alkyl), or —$NR^8R^9$, where $R^8$ is as described previously and $R^9$ is H or alkyl. Exemplary aralkyl groups include benzyl, 2-chlorobenzyl, 4-(dimethylamino)benzyl, phenethyl, 1-pyrrolylmethyl, 2-thienylmethyl, and 3-pyridylmethyl.

The term "disease" includes any unhealthy condition of an animal including particularly Parkinson's disease, Huntington's disease, Alzheimer's disease, multiple sclerosis, diabetes, motor disorders, seizures, and cognitive dysfunctions due to aging.

The term "fatty alcohol residue" is a linear hydrocarbyl group having from seven to twenty carbon atoms, optionally containing up to three carbon-carbon double bonds. Exemplary fatty alcohol residues include decyl, pentadecyl, hexadecyl (cetyl), octadecyl (stearyl), oleyl, linoleyl, and eicosyl.

The term "growth factor" means an extracellular polypeptide-signaling molecule that stimulates a cell to grow or proliferate.

The term "injury" includes any acute damage of an animal including non-hemorrhagic stroke, traumatic brain injury, perinatal asphyxia associated with fetal distress such as that following abruption, cord occlusion or associated with intrauterine growth retardation, perinatal asphyxia associated with failure of adequate resuscitation or respiration, severe CNS insults associated with near miss drowning, near miss cot death, carbon monoxide inhalation, ammonia or other gaseous intoxication, cardiac arrest, coma, meningitis, hypoglycemia and status epilepticus, episodes of cerebral asphyxia associated with coronary bypass surgery, hypotensive episodes and hypertensive crises, cerebral trauma and toxic injury.

The term "pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

The term "pharmaceutically acceptable salt" means a salt that is pharmaceutically acceptable and has the desired pharmacological properties. Such salts include salts that can be formed where acidic protons present in the compounds react with inorganic or organic bases. Suitable inorganic salts include those formed with the alkali metals, e.g. sodium and potassium, magnesium, calcium, and aluminium. Suitable organic salts include those formed with organic bases such as amines e.g. ethanolamine, diethanolamine, triethanolamine, tromethamine, N-methylglucamine, and the like. Salts also include acid addition salts formed by reaction of an amine group or groups present in the compound with an acid. Suitable acids include inorganic acids (e.g. hydrochloric and hydrobromic acids) and organic acids (e.g. acetic acid, citric acid, maleic acid, and alkane- and arene-sulfonic acids such as methanesulfonic acid and benzenesulfonic acid). When there are two acidic groups present in a compound, a pharmaceutically acceptable salt may be a mono-acid mono-salt or a di-salt; and similarly where there are more than two acidic groups present, some or all of such groups can be salified. The same reasoning can be applied when two or more amine groups are present in a compound.

The term "protecting group" is a group that selectively blocks one or more reactive sites in a multifunctional compound such that a chemical reaction can be carried out selectively on another unprotected reactive site and such that the group can readily be removed after the selective reaction is complete.

The term "therapeutically effective amount" means the amount of an agent that, when administered to an animal for treating a disease, is sufficient to effect treatment for that disease as measured using a test system recognized in the art.

The term "treating" or "treatment" of a disease may include preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

The term "functional deficit" means a behavioral deficit associated with neurological damage. Such deficits include deficits of gait, as observed in patients with Parkinson's disease, motor abnormalities as observed in patients with Huntington's disease. Functional deficit also includes abnormal foot placement.

The term "seizure" means an abnormal pattern of neural activity in the brain that results in a motor deficit or lack of motor control resulting in abnormal motion, including spasmodic motion. "Seizure" includes electroencephalographic abnormalities, whether or not accompanied by abnormal motor activity.

Implicit hydrogen atoms (such as hydrogen atoms on a pyrrolidine ring, etc.) are omitted from the formulae for clarity, but should be understood to be present.

Compounds of the Invention

While the broadest definition of the invention is set out in the Summary, certain compounds of this invention are presently described.

Some compounds of this invention are compounds where:
(a) the compounds are compounds of Formula 1;
(b) m is 0;
(c) n is 1;
(d) at least one of X, Y, $R^1$, $R^2$, $R^3$, $R^4$, and $R^5$ is not hydrogen;
(e) X is $-NR^6R^7$; and
(f) Y is $-CO_2R^5$ or $-CO_2NR^6R^7$; and
(g) Z is $-CO_2R^5$ or $-CO_2NR^6R^7$.

Other compounds of the invention are compounds of Formula 1 wherein X is $-NR^6R^7$ and $R^6$ and $R^7$ are independently alkyl or aralkyl. The more preferred embodiment is a compound of Formula 1 wherein X is $-NR^6R^7$ and both $R^6$ and $R^7$ are alkyl.

Yet another compound of the invention is Glycyl-L-2-Methylprolyl-L-Glutamic Acid (G-2MePE), a compound of Formula 1 wherein m is 0, n is 1, $R^1=R^3=R^4=H$, $R^2$ is methyl, X is $NR^6R^7$ where $R^6=R^7=H$, Y is $CO_2R^5$ where $R^5=H$, Z is $CO_2R^5$ where $R^5=H$.

Pharmacology and Utility

Compounds of this invention can have anti-apoptotic, anti-necrotic effects and/or anti-neurodegenerative effects. Their activity in vivo can be measured by cell counts, specific staining of desired markers, or by methods such as those discussed in Klempt N D et al: Hypoxia-ischemia induces transforming growth factor β1 mRNA in the infant rat brain. Molecular Brain Research: 13: 93-101. Their activity can also be measured in vitro. The compounds of this invention also can have pharmacological and therapeutic activities similar to those of GPE, and these activities can be measured by methods known in the art, and discussed in the documents cited herein, and by methods used for measuring the activity of GPE. Additionally, compounds of this invention can have pharmacokinetic properties that differ from those of GPE. In particular, G-2MePE can have a longer plasma half-life (t½) than that of GPE. Thus, in certain embodiments, G-2MePE can be administered as a bolus, and its effects can be sustained for a longer period of time than effects of GPE.

Therapeutic efficacy can also be assessed using behavioral tests. Such tests are known in the art and include tests of foot placement in animals and monitoring of motor activity. Other tests of neurological impairment in animals correlate with neurological impairment in humans, although the precise end-point being measured may differ. For example, a flaccid tail in a small mammal (rat or mouse) can indicate neurological impairment and can correlate with impairment in humans, even though humans do not have a tail. However, in spite of these differences, changes in tail flaccidity or other metrics correlate with impairment in humans, and therefore, tests in animals of therapeutic efficacy can be predictive of similar effects in human beings. In certain disorders, seizures can be observed as a result of loss of neurons or their function. Seizure activity therefore can reflect underlying neurological damage, and improvement in seizure activity can reflect therapeutic efficacy of GPE compounds. In certain cases, behavioral tests and tests for motor deficits can be more sensitive than histological or anatomical measurements.

Additionally, therapeutic efficacy can be assessed using in vitro studies of neural cells, or can be assessed using in vivo studies of art-recognized animal systems. In particular, we have tested pharmaceutical efficacy of GPE compounds using cultured neural cells. Such studies are recognized in the art as being predictive of therapeutic effects in human disease. Diseases for which animal systems are recognized as useful include autoimmune encephalopathies such as multiple sclerosis, Alzheimer's disease, Parkinson's disease, Huntington's disease, type I diabetes, type II diabetes and conditions characterized by loss of neural cells, including hypoxia/ischemia, perinatal asphyxia, hemorrhagic and non-hemorrhatic stroke and toxic neurological damage. Additionally, certain in vivo animal systems are well recognized in the art as being predictive of therapeutic effects of pharmaceutical agents in human brain injuries. Such injuries include hypoxia/ischemia, stroke and traumatic brain injuries including penetrating brain injury. Additionally, in vivo animal systems for studying functional disorders including seizures are recognized in the art as being predictive of such functional disorder in human beings. Thus, with the use of in vitro and/or in vivo studies of neuroprotection in the above-mentioned art-recognized animal systems, and of studies of functional neurological disorders, studies of therapeutic efficacy of GPE compounds are predictive of effects observed in human patients having such disorders.

The therapeutic ratio of a compound can be determined, for example, by comparing the dose that gives effective anti-apoptotic and anti-necrotic activity in a suitable in vivo model such as a hypoxic-ischemic injury (Sirimanne E S, Guan J, Williams C E and Gluckman P D: Two models for determining the mechanisms of damage and repair after hypoxic-ischemic injury in the developing rat brain. Journal of Neuroscience Methods: 55: 7-14, 1994) in a suitable animal species such as the rat, with the dose that gives significant observable side-effects in the test animal species.

The therapeutic ratio of a compound can also be determined, for example by comparing the dose that gives effective neuroprotection in a suitable in vivo model (Examples 3, 4, 5, 6 and 7 below) in a suitable animal species such as the rat, with the dose that gives significant weight loss (or other observable side-effects) in the test animal species.

Pharmaceutical Compositions and Administration

In general, compounds of this invention can be administered in therapeutically effective amounts by any of the usual modes known in the art, either singly or in combination with at least one other compound of this invention and/or at least one other conventional therapeutic agent for the disease being treated. A therapeutically effective amount may vary widely depending on the disease or injury, the severity of the disease, the age and relative health of the animal being treated, the potency of the compound(s), and other factors. As anti-apoptotic, anti-necrotic, anti-neurodegenerative, therapeutically effective amounts of compounds of this invention can range from about 0.001 milligrams per kilogram (mg/kg) to about 100 (mg/kg) mass of the animal, for example, about 0.1 to about 10 mg/kg, with lower doses such as about 0.001 to about 0.1 mg/Kg, e.g. about 0.01 mg/Kg, being appropriate for administration through the cerebrospinal fluid, such as by intracerebroventricular administration, and higher doses such as about 1 to about 100 mg/Kg, e.g. about 10 mg/Kg, being appropriate for administration by methods such as oral, systemic (e.g. transdermal), or parenteral (e.g. intravenous) administration. A person of ordinary skill in the art will be able without undue experimentation, having regard to that skill and this disclosure, to determine a therapeutically effective amount of a compound of this invention for a given disease or injury.

In general, compounds of this invention can be administered as pharmaceutical compositions by one of the following routes: oral, topical, systemic (e.g. transdermal, intranasal, or by suppository), or parenteral (e.g. intramuscular, subcutaneous, or intravenous injection), by administration to the CNS (e.g. by intraspinal or intercisternal injection); by implantation, and by infusion through such devices as osmotic pumps, transdermal patches, and the like. Compositions can take the form of tablets, pills, capsules, semisolids, powders, sustained release formulation, solutions, suspensions, elixirs, aerosols, or any other appropriate compositions; and comprise at least one compound of this invention in combination with at least one pharmaceutically acceptable or physiological acceptable excipient. Suitable excipients are well known to persons of ordinary skill in the art, and they, and the methods of formulating the compositions, may be found in such standard references as Gennaro A R: Remington: The Science and Practice of Pharmacy, $20^{th}$ ed., Lippincott, Williams & Wilkins, 2000. Suitable liquid carriers, especially for injectable solutions, include water, aqueous saline solution, aqueous dextrose solution, glycols, and the like, with isotonic solutions being preferred for intravenous, intraspinal, and intracisternal administration and vehicles such as artificial cerebrospinal fluid being also especially suitable for administration of the compound to the CNS. The above text is expressly incorporated herein fully by reference.

Compounds of this invention can be administered after or before onset of a condition that is likely to result in neurodegeneration or a symptom thereof. For example, it is known that hypoxia/ischemia can occur during coronary artery bypass graft (CABG) surgery. Thus, a patient can be pretreated with a compound of this invention before being placed on an extracorporeal oxygenation system. In some embodiments, it can be desirable to administer a compound of this invention beginning about 4 hours before surgery or before an event that is likely to lead to traumatic or other neurological injury. In other embodiments, it can be desirable to infuse a compound of this invention during the surgery or during a surgical procedure to repair a neurological injury. Compounds of this invention can also be used in emergency situations, for example in a patient that has just experienced a stroke, hypoxic event, traumatic brain injury or other acute insult. In such situations, a compound of this invention can be administered immediately after a diagnosis of neural injury is made.

In some situations, kits containing compound of this invention can be prepared in advance of use in the field. A kit can contain a vial containing a compound of the invention in a pharmaceutically acceptable formulation (e.g., for injection), along with a syringe or other delivery device, and instructions for use. In situations in which a seizure is diagnosed, a compound of this invention can be administered along with an anticonvulsant. Many anticonvulsants are known in the art and need not be described in detail herein.

Additionally, "secondary" neurological injuries can occur after a primary insult such as a traumatic injury, stroke or surgical procedure. For example, after a stroke, penetrating brain injury or a CABG procedure, inflammation of neural tissue can lead to neurodegeneration. Secondary injuries can be reflected by increased activation of inflammatory cells (e.g., astrocytes and/or microglia), and actions of inflammatory mediators can cause neurological damage. Thus, in some embodiments, it can be desirable to administer a compound of this invention for periods beginning before the insult, to up to about 100 hours after the insult. In other embodiments, it can be desirable to administer a compound of this invention beginning before the insult, during the insult and after the insult, either continuously, as an infusion, or in discrete doses separated by a desired time interval.

Compounds of this invention can also be suitably administered by a sustained-release system. Suitable examples of sustained-release compositions include semi-permeable polymer matrices in the form of shaped articles, e.g., films, or microcapsules. Sustained-release matrices, include polylactides (U.S. Pat. No. 3,773,919; EP 58,481), copolymers of L-glutamic acid and gamma-ethyl-L-glutamate (Sidman et al., 1983), poly(2-hydroxyethyl methacrylate) (Langer et al., 1981), ethylene vinyl acetate (Langer et al., supra), or poly-D-(−)-3-hydroxybutyric acid (EP 133,988). Sustained-release compositions also include a liposomally entrapped compound. Liposomes containing the compound are prepared by methods known per se: DE 3,218,121; Epstein et al., 1985; Hwang et al., 1980; EP 52,322; EP 36,676; EP 88,046; EP 143,949; EP 142,641; Japanese Pat. Appln. 83-118008; U.S. Pat. Nos. 4,485,045 and 4,544,545 and EP 102, 324. Ordinarily, liposomes are of the small (from or about 200 to 800 Angstroms) unilamellar type in which the lipid content is greater than about 30 mole percent cholesterol, the selected proportion being adjusted for the most efficacious therapy.

Compounds of this invention can also be attached to polyethylene glycol ("PEGylated") to increase their lifetime in vivo, based on, e.g., the conjugate technology described in WO 95/32003.

Desirably, if possible, when administered as an anti-apoptotic agent, an anti-necrotic agent, or an anti-neurodegenerative agent, compounds of this invention can be administered orally. The amount of a compound of this invention in the composition can vary widely depending on the type of composition, size of a unit dosage, kind of excipients, and other factors well known to those of ordinary skill in the art. In general, the final composition can comprise from about 0.0001 percent by weight (% w) to about 10% w of the compound of this invention, preferably about 0.001% w to about 1% w, with the remainder being a excipient or excipients.

A composition may optionally contain, in addition to a compound of this invention, at least one agent selected from, for example, growth factors and associated derivatives (insulin-like growth factor-I (IGF-I), insulin-like growth factor-II (IGF-II), transforming growth factor-$\beta1$, activin, growth hormone, nerve growth factor, growth hormone binding protein, IGF-binding proteins (especially IGFBP-3), basic fibroblast growth factor, acidic fibroblast growth factor, the hst/Kfgk gene product, FGF-3, FGF-4, FGF-6, keratinocyte growth factor, androgen-induced growth factor. Additional members of the FGF family include, for example, int-2, fibroblast growth factor homologous factor-1 (FHF-1), FHF-2, FHF-3 and FHF-4, karatinocyte growth factor 2, glial-activating factor, FGF-10 and FGF-16, ciliary neurotrophic factor, brain derived growth factor, neurotrophin 3, neurotrophin 4, bone morphogenetic protein 2 (BMP-2), glial-cell line derived neurotrophic factor, activity-dependant neurotrophic factor, cytokine leukaemia inhibiting factor, oncostatin M, interleukin), $\alpha$-, $\beta$-, $\gamma$-, or consensus interferon, and TNF-$\alpha$. Other forms of neuroprotective therapeutic agents include, for example, clomethiazole; kynurenic acid, Semax, tacrolimus, L-threo-1-phenyl-2-decanoylamino-3-morpholino-1-propanol, andrenocorticotropin-(4-9) analogue [ORG 2766] and dizolcipine (MK-801), selegiline; glutamate antagonists such as, NPS1506, GV1505260, MK-801, GV150526; AMPA antagonists such as 2,3-dihydroxy-6-nitro-7-sulfamoylbenzo(f)quinoxaline (NBQX), LY303070 and LY300164; anti-inflammatory agents directed against the addressin MAdCAM-1 and/or its integrin $\alpha4$ receptors ($\alpha4\beta1$ and $\alpha4\beta7$), such as anti-MAdCAM-1mAb MECA-367 (ATCC accession no. HB-9478). Most of these agents, especially the peptides such as the growth factors, etc. are not orally active, and will require administration by injection or infusion.

Preparation of Compositions

Starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to the person of ordinary skill in the art following procedures described in such references as Fieser and Fieser's Reagents for Organic Synthesis, vols. 1-17, John Wiley and Sons, New York, N.Y., 1991; Rodd's Chemistry of Carbon Compounds, vols. 1-5 and supplements, Elsevier Science Publishers, 1989; Organic Reactions, vols. 1-40, John Wiley and Sons, New York, N.Y., 1991; March J; Advanced Organic Chemistry, $4^{th}$ ed. John Wiley and Sons, New York, N.Y., 1992; and Larock: Comprehensive Organic Transformations, VCH Publishers, 1989. In most instances, amino acids and their esters or amides, and protected amino acids, are widely commercially available; and the preparation of modified amino acids and their amides or esters are extensively described in the chemical and biochemical literature and thus well-known to persons of ordinary skill in the art. For example, N-pyrrolidineacetic acid is described in Dega-Szafran Z and Pryzbylak R. Synthesis, IR, and NMR studies of zwitterionic $\alpha$-(1-pyrrolidine)alkanocarboxylic acids and their N-methyl derivatives. J. Mol. Struct.: 436-7, 107-121, 1997; and N-piperidineacetic acid is described in Matsuda O, Ito S, and Sekiya M. Reaction of N-(alkoxymethyl)dialkylamines and N,N'-methylenebisdialkylamines with isocyanides. Chem. Pharm. Bull. 23(1), 219-221, 1975, each article herein expressly incorporated herein fully by reference.

Starting materials, intermediates, and compounds of this invention may be isolated and purified using conventional techniques, including filtration, distillation, crystallization, chromatography, and the like. They may be characterized using conventional methods, including physical constants and spectral data.

Compounds of this invention may be prepared by the methods described below and as given in the Examples.

Compounds of Formula 1 are analogues of GPE, or modifications thereof, such as esters or amides. In general, they may be prepared by methods such as are already well-known to persons of ordinary skill in the art of peptide and modified peptide synthesis, following the reaction schemes set forth in the FIGS. 1-11 accompanying this specification, or by following other methods well-known to those of ordinary skill in the art of the synthesis of peptides and analogs.

Conveniently, synthetic production of the polypeptides of the invention may be according to the solid-phase synthetic method described by Merrifield et al. Solid phase peptide synthesis. I. The synthesis of a tetrapeptide: J. Amer. Chem. Soc.: 85, 2149-2156, 1963, herein expressly incorporated fully by reference. This technique is well understood and is a common method for preparation of peptides. The general concept of this method depends on attachment of the first amino acid of the chain to a solid polymer by a covalent bond.

Succeeding protected amino acids are added, on at a time (stepwise strategy), or in blocks (segment strategy), until the desired sequence is assembled. Finally, the protected peptide is removed from the solid resin support and the protecting groups are cleaved off. By this procedure, reagents and by-products are removed by filtration, thus eliminating the necessity of purifying intermediaries.

Amino acids may be attached to any suitable polymer as a resin. The resin must contain a functional group to which the first protected amino acid can be firmly linked by a covalent bond. Various polymers are suitable for this purpose, such as cellulose, polyvinyl alcohol, polymethylmethacrylate and polystyrene. Suitable resins are commercially available and well known to those of skill in the art. Appropriate protective groups usable in such synthesis include tert-butyloxycarbonyl (BOC), benzyl (Bzl), t-amyloxycarbonyl (Aoc), tosyl (Tos), o-bromo-phenylmethoxycarbonyl (BrZ), 2,6-dichlorobenzyl ($BzlCl_2$), and phenylmethoxycarbonyl (Z or CBZ). Additional protective groups are identified in Merrifield, cited above, as well as in McOmie J F W: Protective Groups in Organic Chemistry, Plenum Press, New York, 1973, both references expressly incorporated fully herein.

General procedures for preparing peptides of this invention involve initially attaching a carboxyl-terminal protected amino acid to the resin. After attachment the resin is filtered, washed and the protecting group (desirably BOC) on the I-amino group of the carboxyl-terminal amino acid is removed. The removal of this protecting group must take place, of course, without breaking the bond between that amino acid and the resin. The next amino, and if necessary, side chain protected amino acid, is then coupled to the free I-amino group of the amino acid on the resin. This coupling takes place by the formation of an amide bond between the free carboxyl group of the second amino acid and the amino group of the first amino acid attached to the resin. This sequence of events is repeated with successive amino acids until all amino acids are attached to the resin. Finally, the protected peptide is cleaved from the resin and the protecting groups removed to reveal the desired peptide. The cleavage techniques used to separate the peptide from the resin and to remove the protecting groups depend upon the selection of resin and protecting groups and are known to those familiar with the art of peptide synthesis.

Alternative techniques for peptide synthesis are described in Bodanszky et al, Peptide Synthesis, 2nd ed, John Wiley and Sons, New York, 1976, expressly incorporated herein fully by reference. For example, the peptides of the invention may also be synthesized using standard solution peptide synthesis methodologies, involving either stepwise or block coupling of amino acids or peptide fragments using chemical or enzymatic methods of amide bond formation. [See, e.g. H. D. Jakubke in The Peptides, Analysis, Synthesis, Biology, Academic Press, New York, 1987, p. 103-165; J. D. Glass, ibid., pp. 167-184; and European Patent 0324659 A2, describing enzymatic peptide synthesis methods.] These solution synthesis methods are well known in the art.

Commercial peptide synthesizers, such as the Applied Biosystems Model 430A, are available for the practice of these methods.

A person of ordinary skill in the art will not have to undertake undue experimentation, taking account of that skill and the knowledge available, and of this disclosure, in developing one or more suitable synthetic methods for compounds of this invention.

Figure 2:
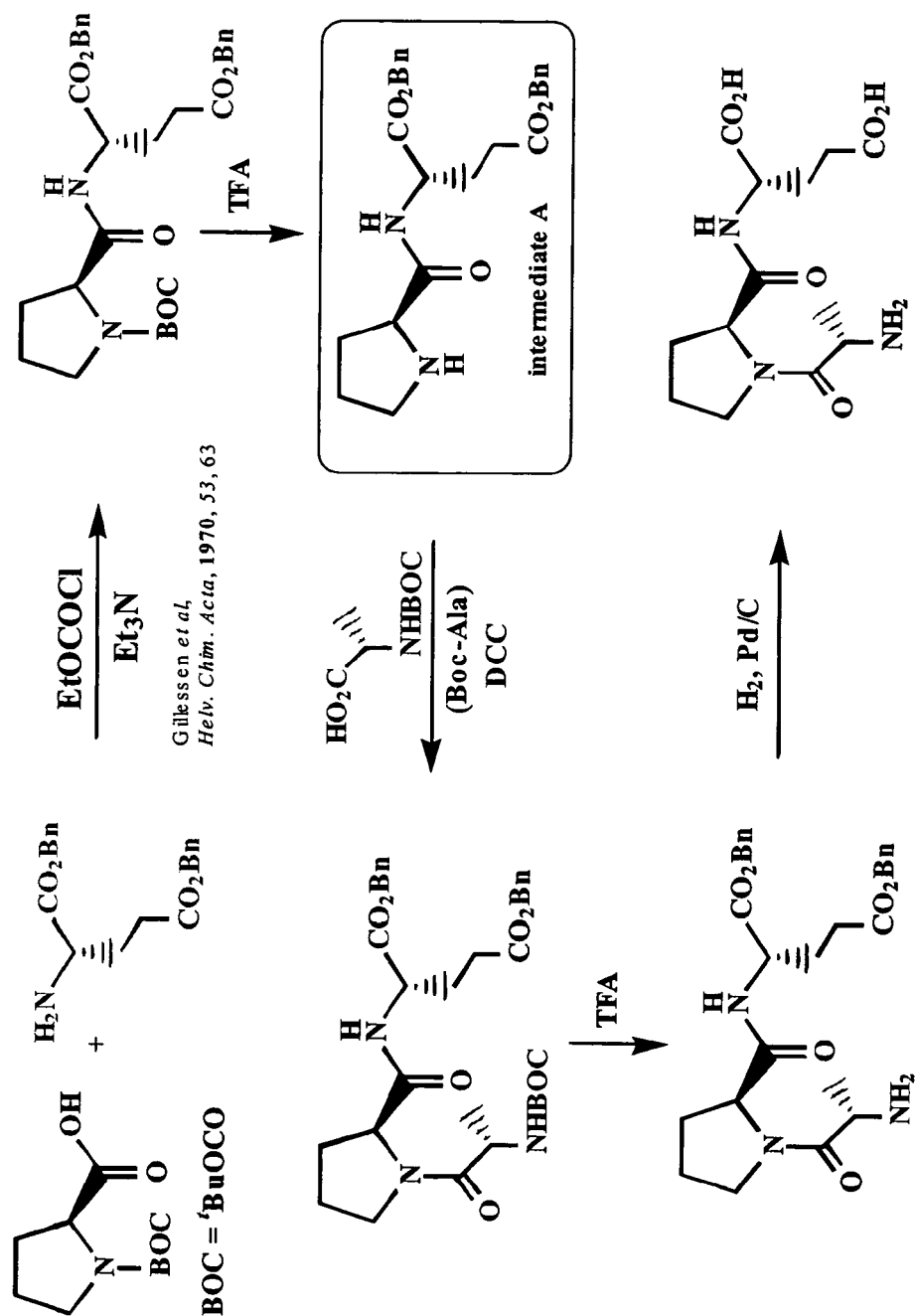
FIGS. 2 and 3 depict schemes for modifying glycine residues on GPE.
Figure 3:
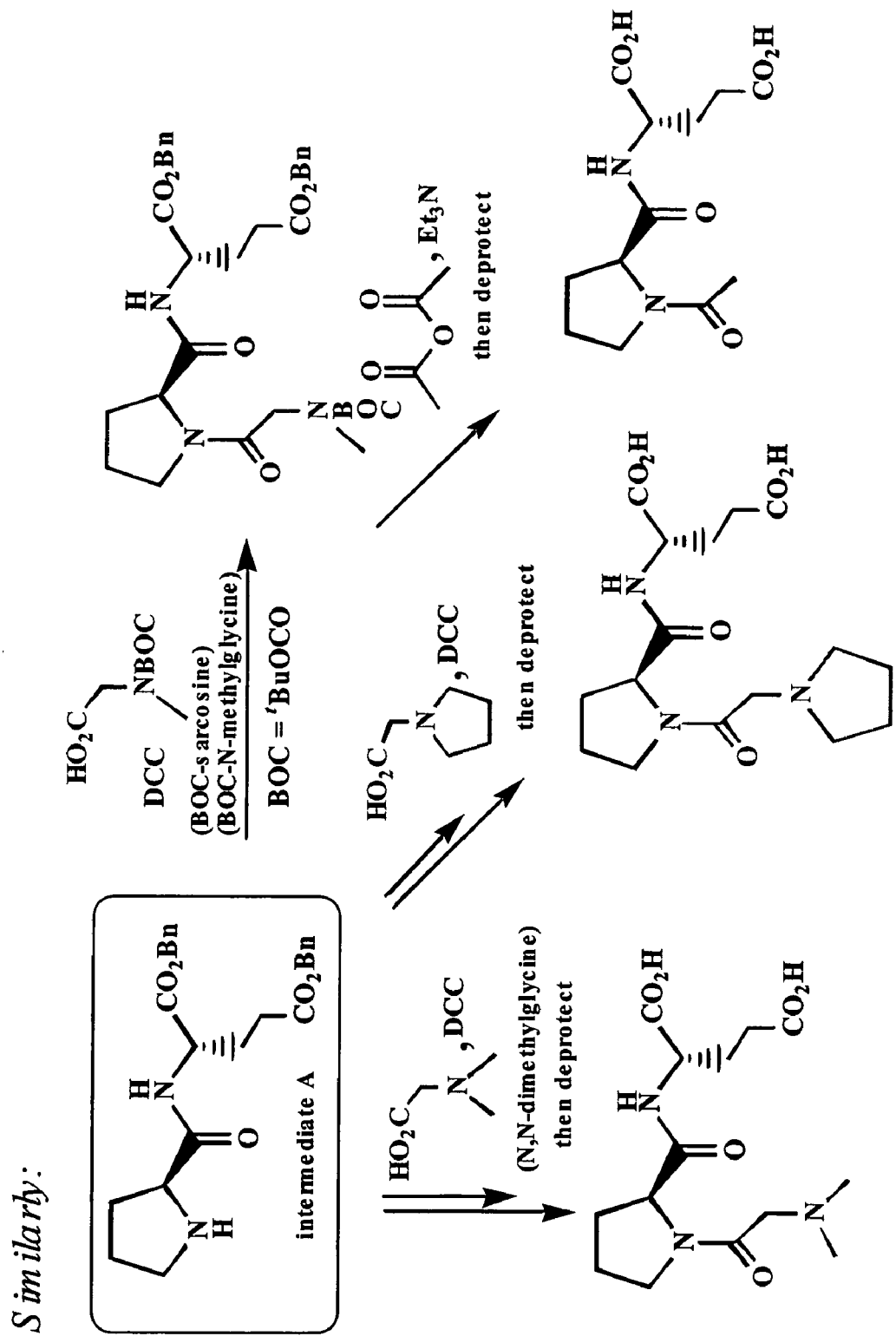
Figure 4:
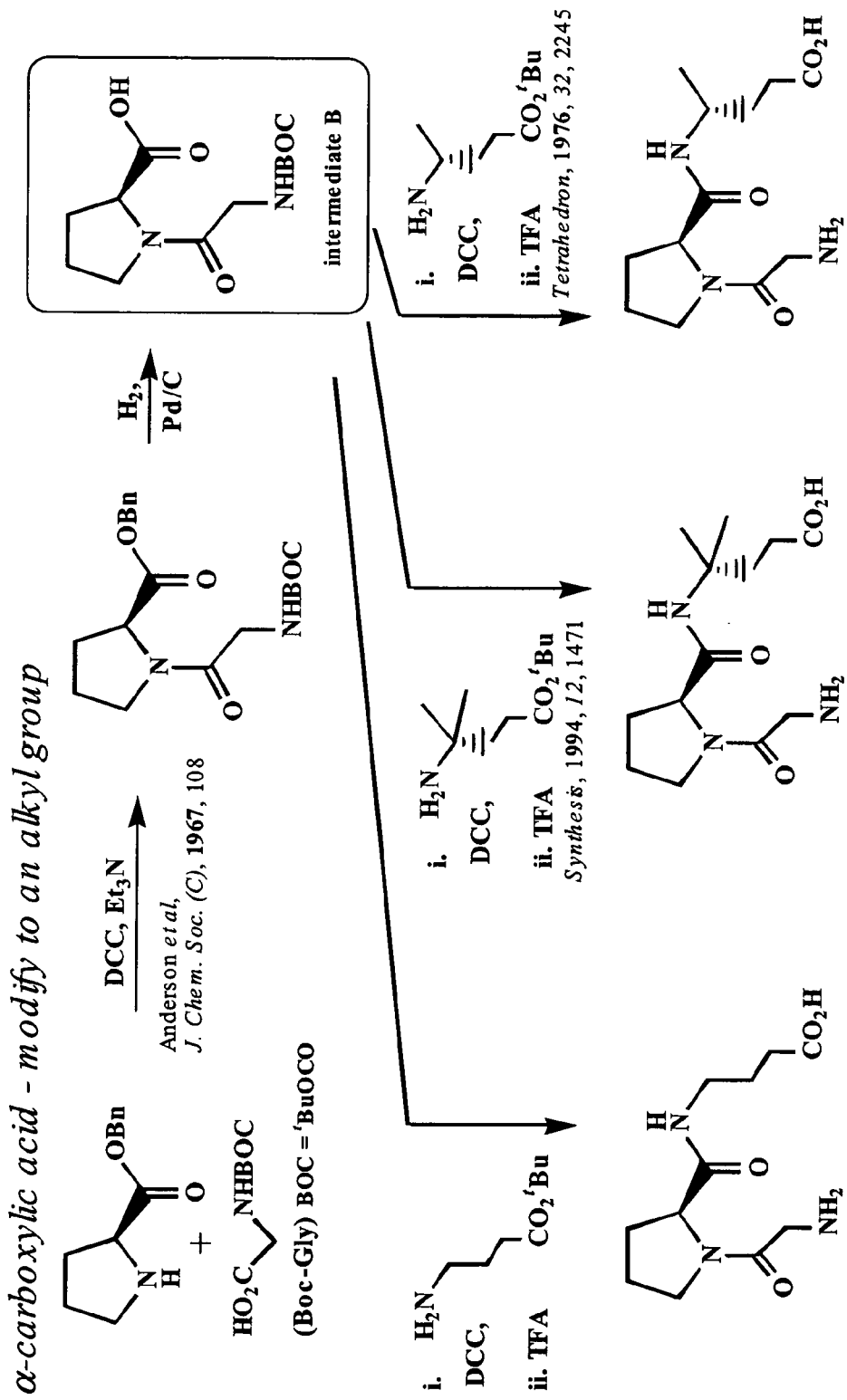
FIGS. 4 through 9 depict schemes for modifying glutamic acid residues of GPE.
Figure 5:
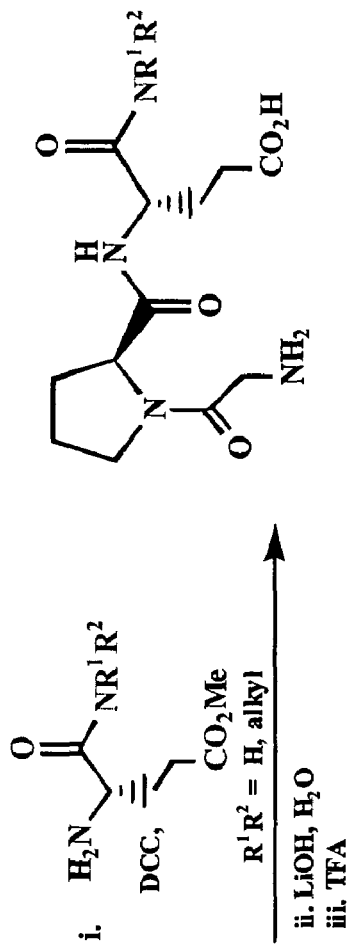
Figure 5:
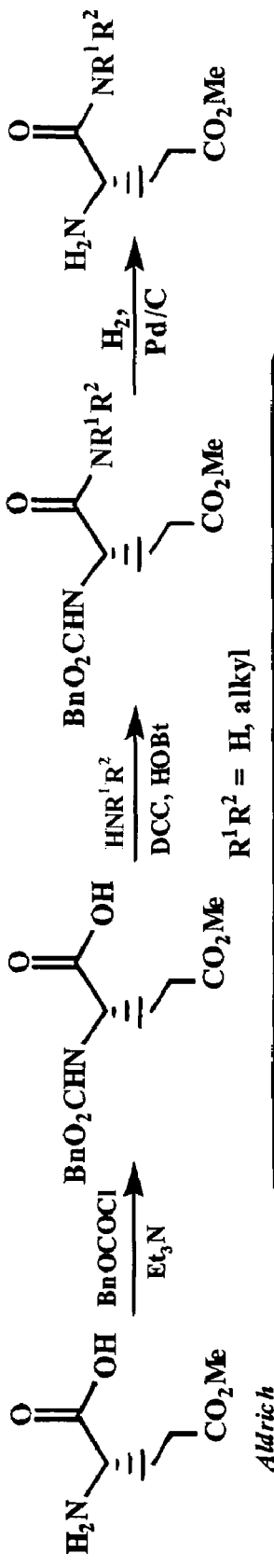
Figure 5:
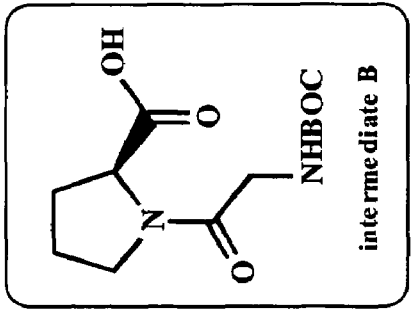
Figure 6:
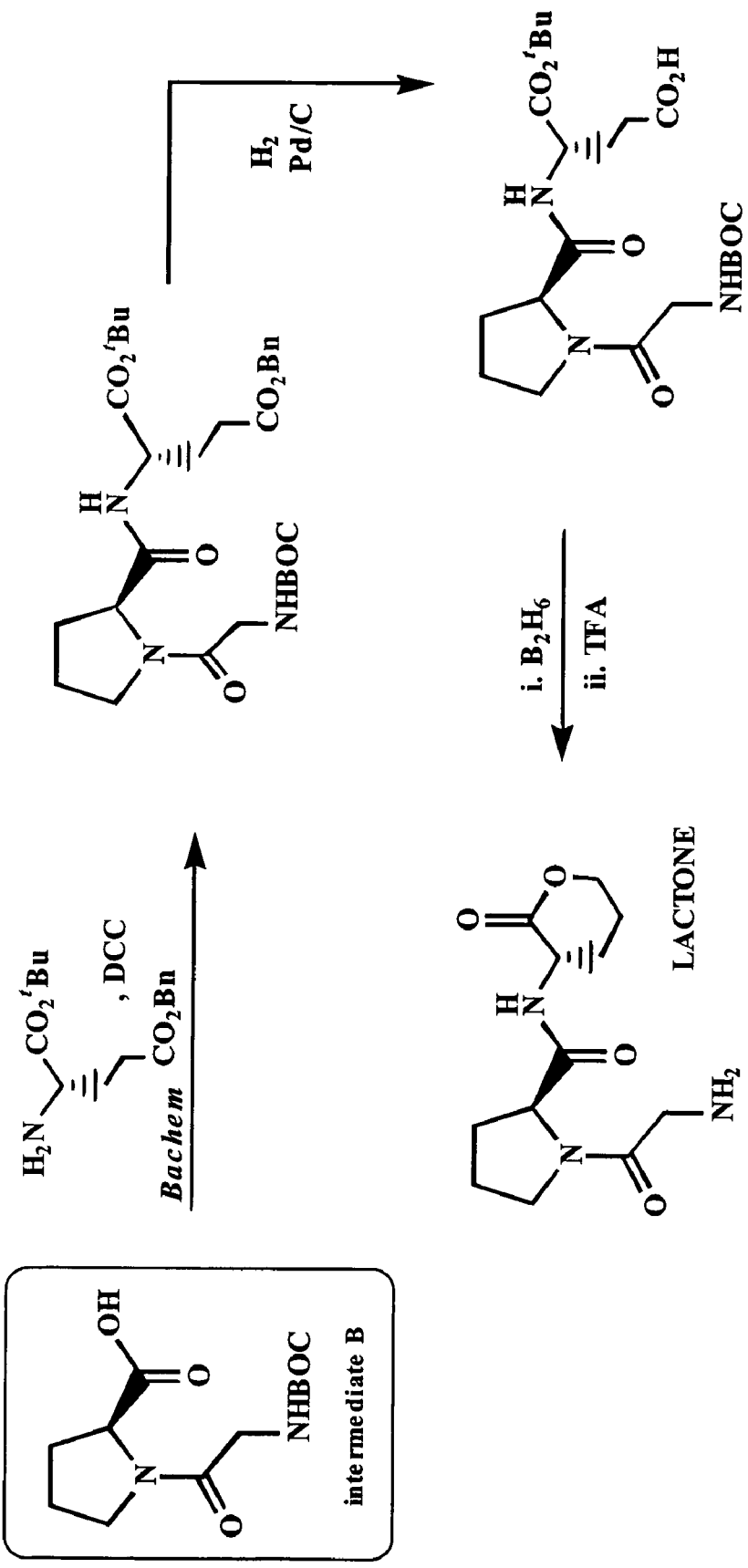
Figure 7:
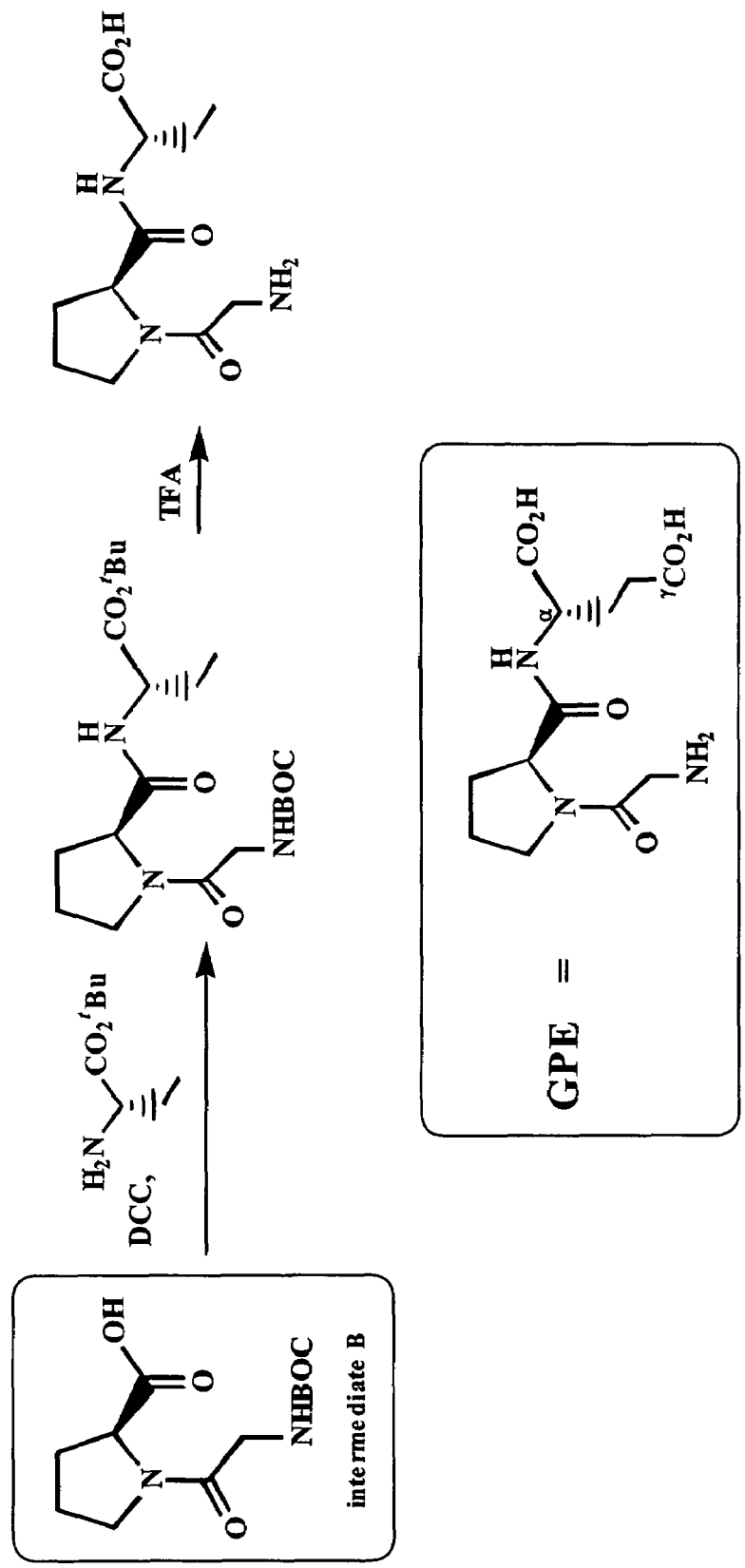
Figure 8:
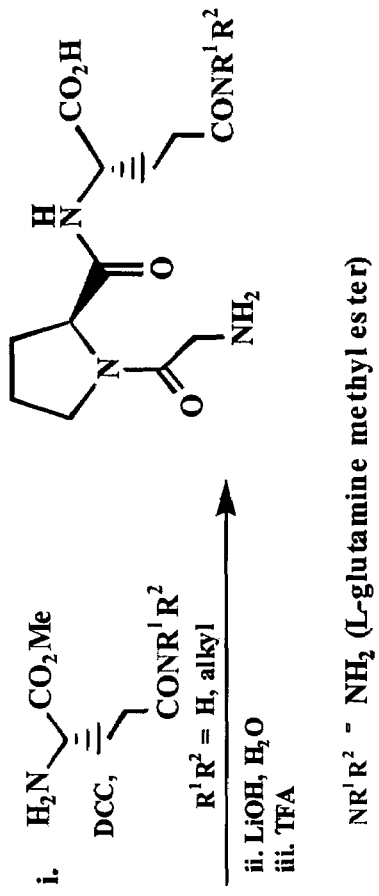
Figure 8:
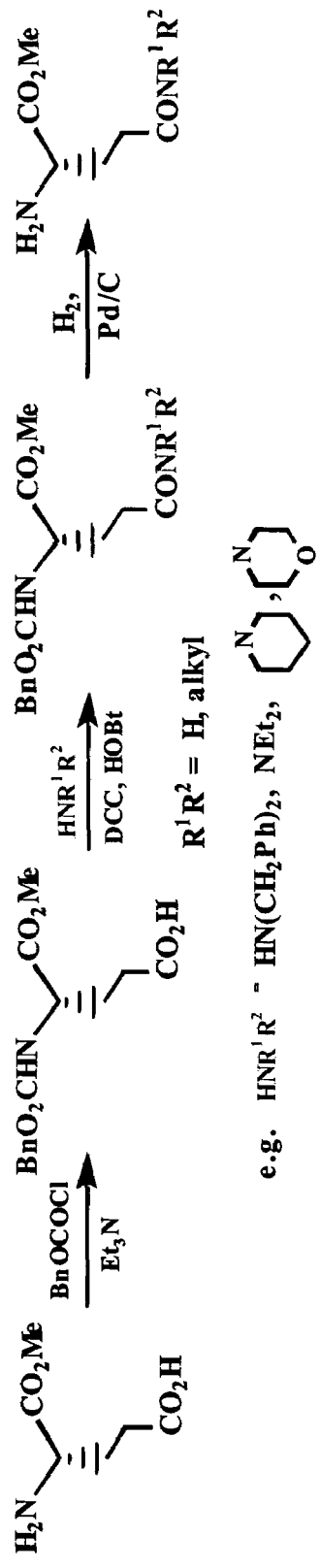
Figure 8:
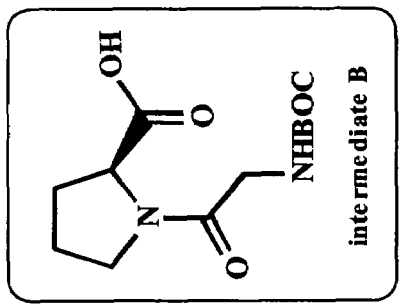
Figure 9:
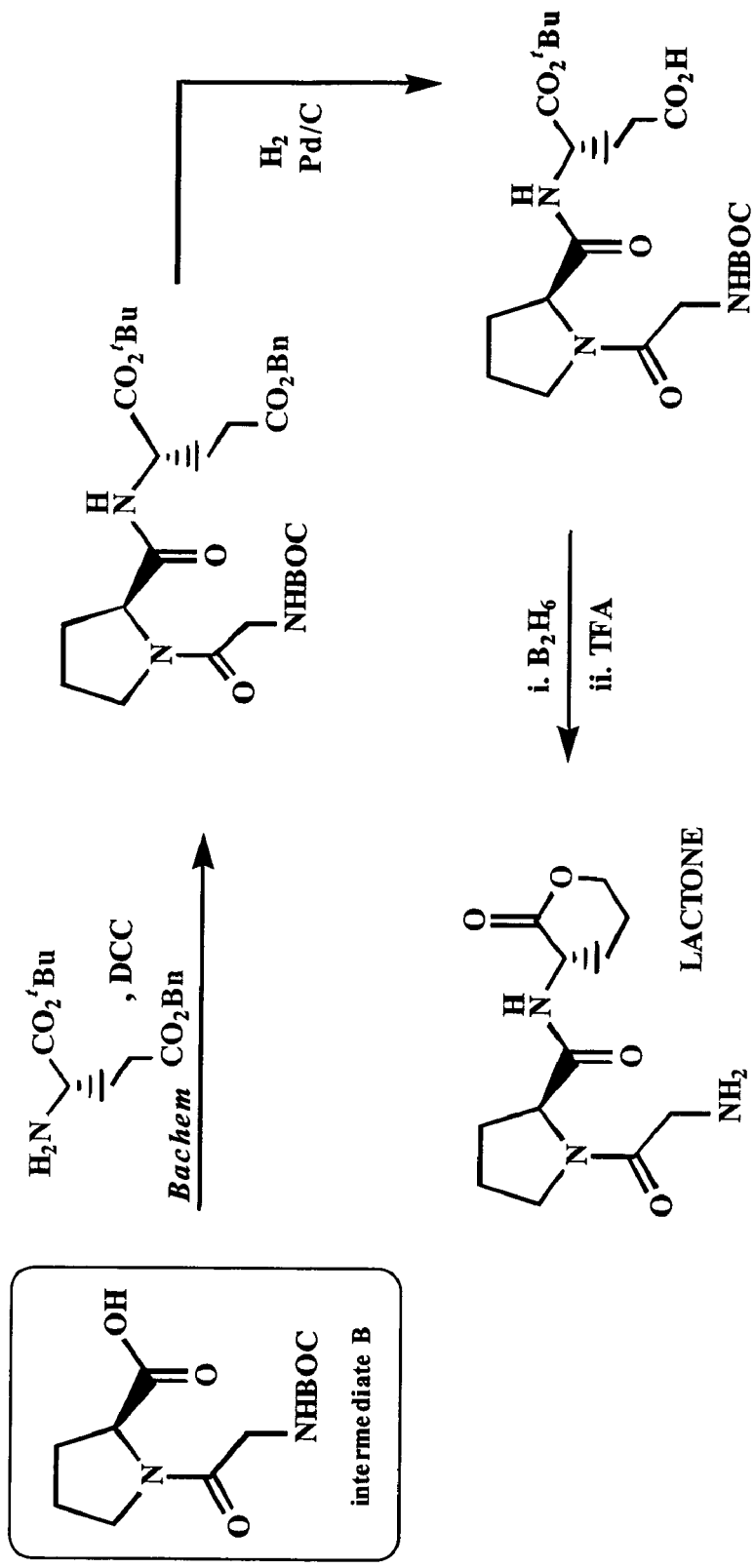
Figure 10:
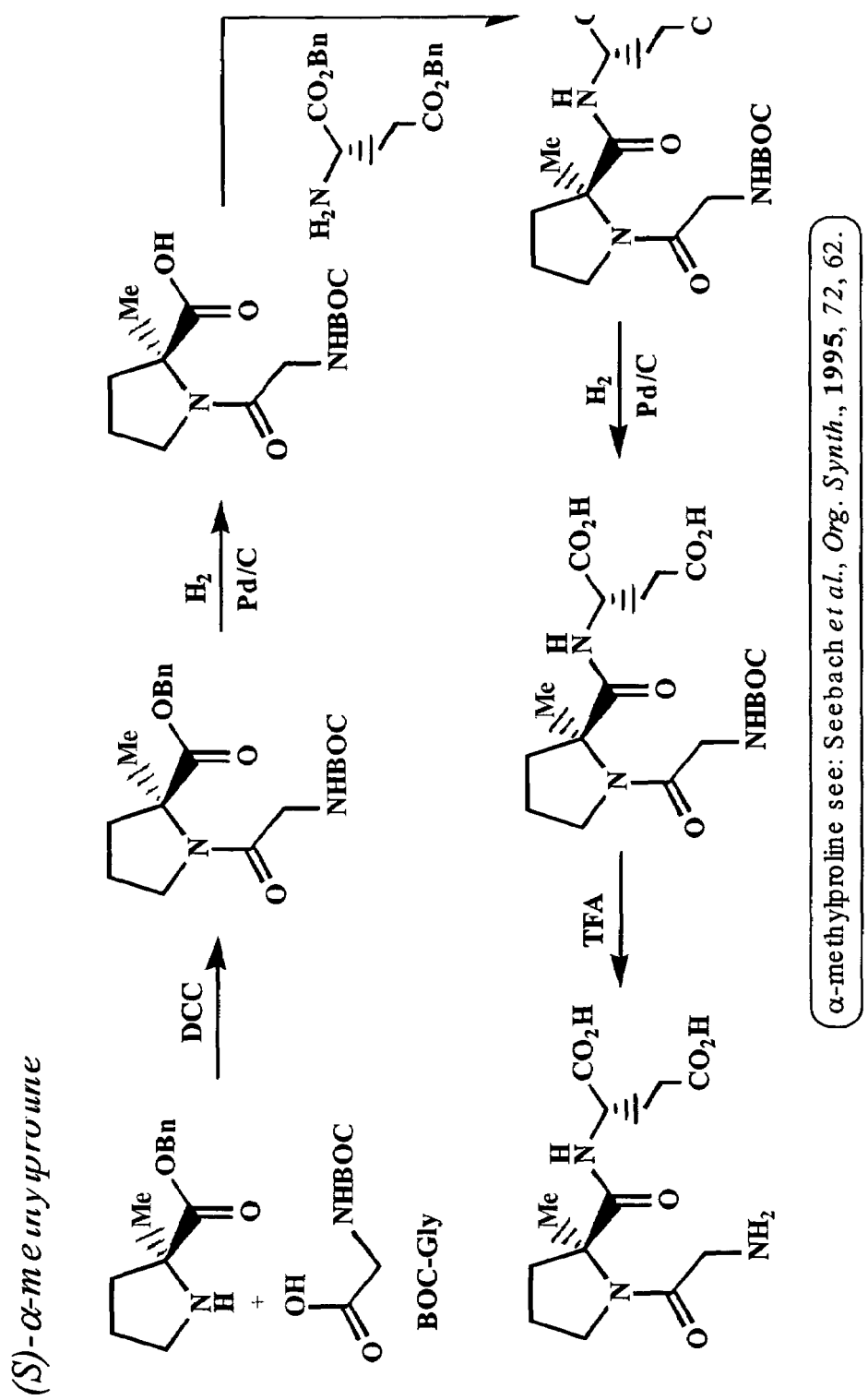
FIGS. 10 and 11 depict schemes for modifying peptide linkages of GPE.
Figure 11:
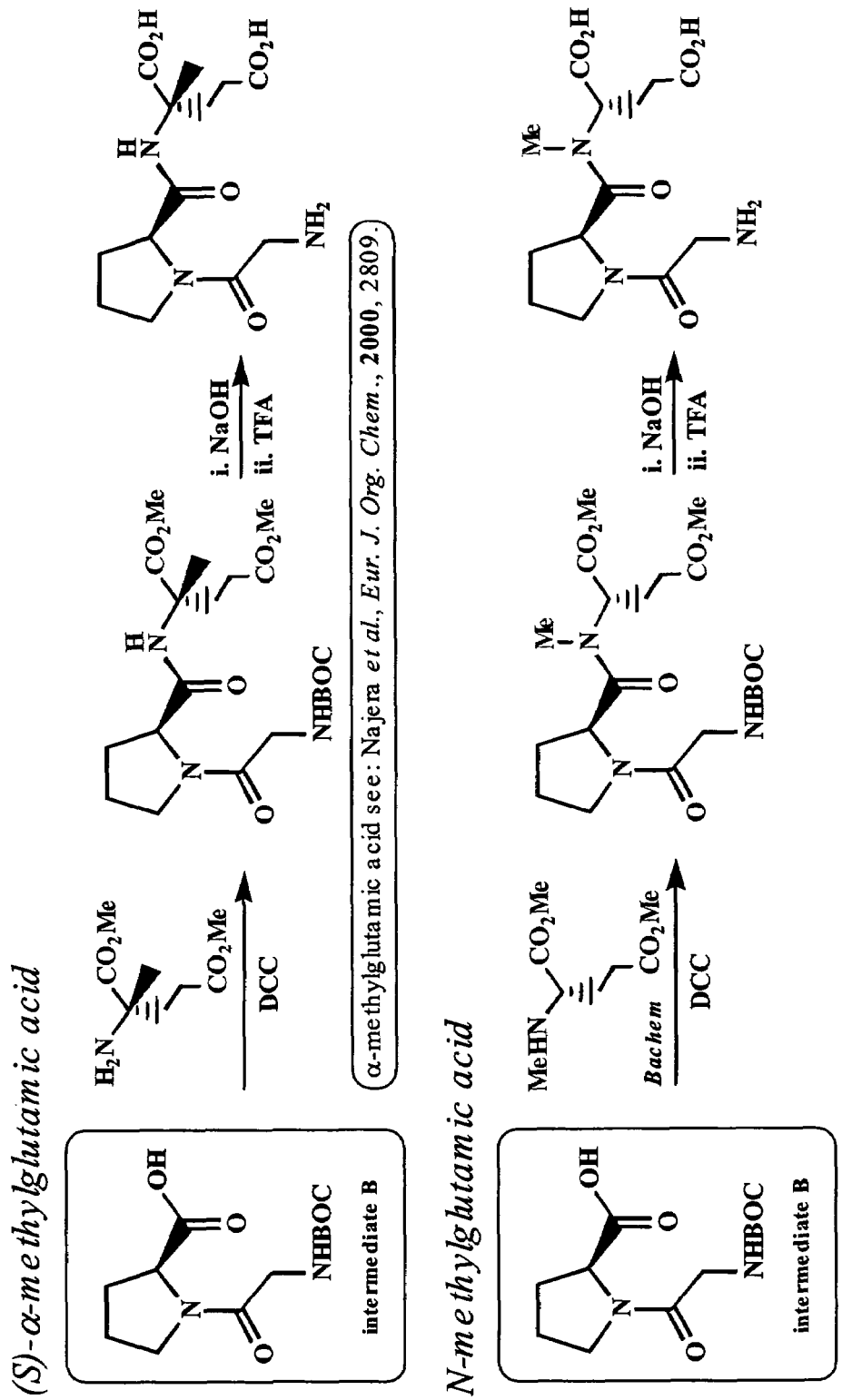
Figure 12:
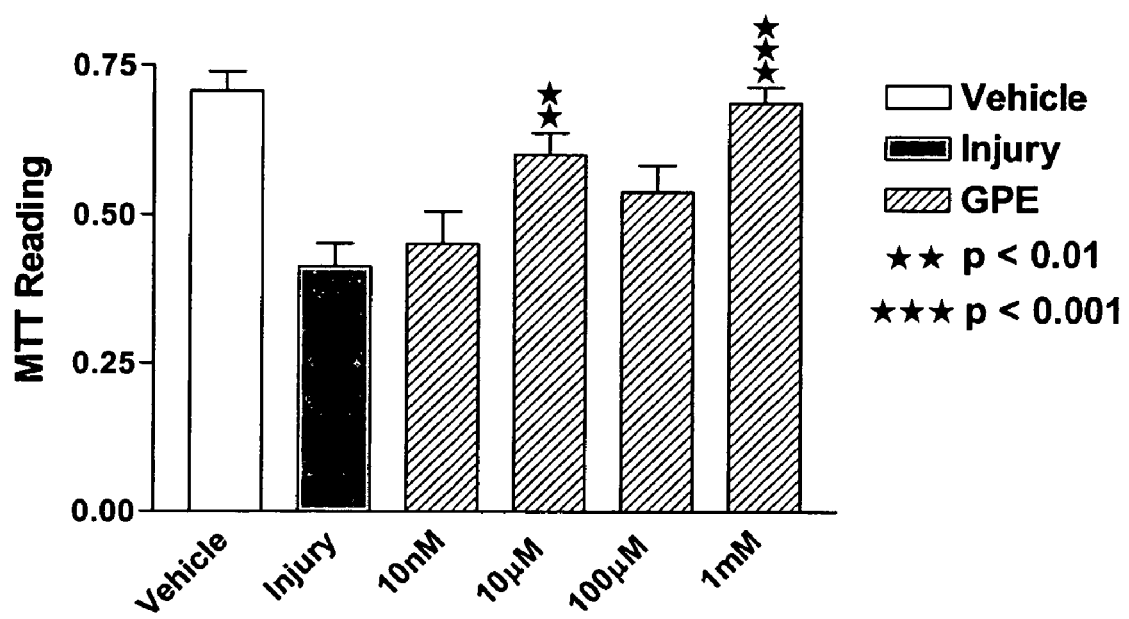
FIGS. 12-15 depict graphs summarizing results of testing neurons in vitro with GPE or G-2MePE and okadaic acid.
Figure 13:
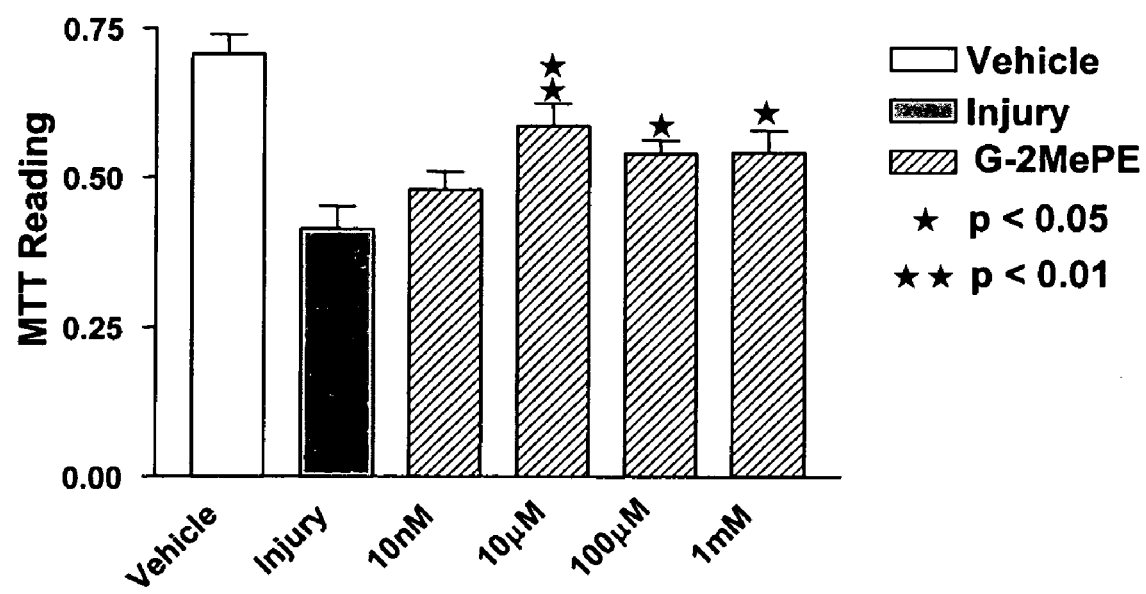

For example, analogs in which the glycine residue of GPE is replaced by an alternative amino acid, or by a non-amino acid, may conveniently be prepared by the preparation of a C-protected proline-glutamic acid dipeptide (such as the dibenzyl ester), and coupling that dipeptide with an N-protected glycine analog, such as BOC-N-methylglycine, BOC-L-valine, N-pyrrolidineacetic acid, and the like, followed by deprotection, as illustrated in FIGS. 2 and 3. Analogs in which the glutamic acid residue of GPE is replaced by an alternative amino acid or an amino acid amide or ester may conveniently be prepared by the preparation of an N-protected glycine-L-proline dipeptide (such as BOC-glycyl-L-proline), and coupling that dipeptide with a C-protected glutamic acid or analog thereof, such as tert-butyl γ-aminobutyrate, methyl 4-amino-4-dimethylcarbamoylbutyrate, L-glutamine methyl ester, dimethyl I-methylglutamate, etc. Lactones may be prepared by the preparation of an appropriate mono-acid-mono-ester derivative and reduction. Analogs in which $R^2$ is alkyl may conveniently be prepared simply by use of the appropriate 2-alkylproline in the synthesis, and similarly analogs in which $R^3$ is alkyl may conveniently be prepared by the use of the appropriate N-alkylglutamic acid or analogue in the synthesis. Where modifications are to be made to two or more amino acids, the coupling techniques will still be the same, with just more than one modified amino acid or analogue being used in the synthesis. The choice of appropriate protecting groups for the method chosen (solid-phase or solution-phase), and of appropriate substrates if solid-phase synthesis is used, will be within the skill of a person of ordinary skill in the art.

Compounds of Formula 2 may be prepared from suitably protected 5-oxo-L-proline or analogs or derivatives thereof, following methods such as the coupling of the proline carboxyl group with a protected glutamic acid or analog or derivative to give an analog of intermediate A of FIG. 2, comparable to the coupling reaction shown in FIG. 2, and then alkylating the pyrrolidine nitrogen with a group of the formula A----$(CH_2)_m$—$CH(R^1)$—$CH_2R$, protected at A if necessary, where R is a leaving group under alkylation conditions. Alternatively, the suitably protected 5-oxo-L-proline may first by alkylated at the pyrrolidine nitrogen to give an analog of intermediate B of FIG. 4, and then coupling this with a suitably protected glutamic acid or analog or derivative in the manner shown in FIGS. 4 though 9.

EXAMPLES

The following examples are intended to illustrate embodiments of this invention, and are not intended to limit the scope to these specific examples.

Example 1

Synthesis of
N,N-Dimethylglycyl-L-prolyl)-L-glutamic acid

The following non-limiting example illustrates the synthesis of a compound of the invention, N,N-Dimethylglycyl-L-prolyl-L-glutamic acid

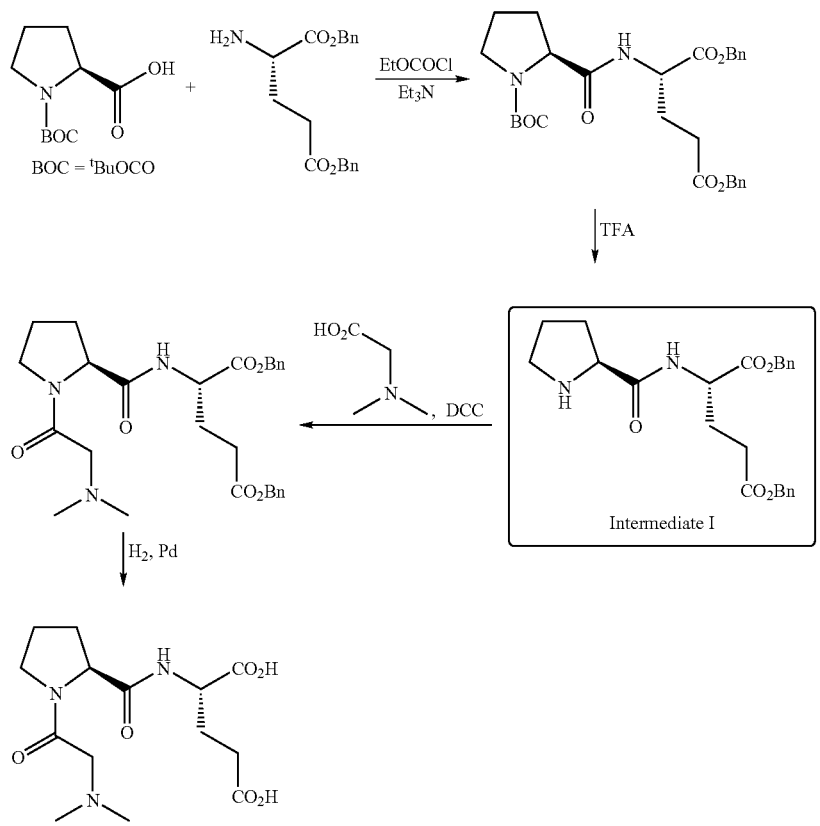

All starting materials and other reagents were purchased from Aldrich; BOC=tert-butoxycarbonyl; Bn=benzyl.

BOC-L-proline-(β-benzyl)-L-glutamic acid benzyl ester

To a solution of BOC-proline (Anderson G W and McGregor A C: J. Amer. Chem. Soc.: 79, 6810, 1994) (10 mmol) in dichloromethane (50 ml), cooled to 0° C., was added triethylamine (1.39 ml, 10 mmol) and ethyl chloroformate (0.96 ml, 10 mmol). The resultant mixture was stirred at 0° C. for 30 minutes. A solution of dibenzyl-L-glutamate (10 mmol) was then added and the mixture stirred at 0° C. for 2 hours then warmed to room temperature and stirred overnight. The reaction mixture was washed with aqueous sodium bicarbonate and citric acid (2 mol l$^{-1}$) then dried (MgSO$_4$) and concentrated at reduced pressure to give BOC-L-proline-L-glutamic acid dibenzyl ester (5.0 g, 95%).

L-proline-L-glutamic acid dibenzyl ester

A solution of BOC-L-glutamyl-L-proline dibenzyl ester (3.4 g, 10 mmol), cooled to 0° C., was treated with trifluoroacetic acid (25 ml) for 2 h. at room temperature. After removal of the volatiles at reduced pressure the residue was triturated with ether to give L-proline-L-glutamic acid dibenzyl ester.

N,N-Dimethylglycyl-L-prolyl-L-glutamic acid

A solution of dicyclohexylcarbodiimide (10.3 mmol) in dichloromethane (10 ml) was added to a stirred and cooled (0° C.) solution of L-proline-L-glutamic acid dibenzyl ester (10 mmol), N,N-dimethylglycine (10 mmol) and triethylamine (10.3 mmol) in dichloromethane (30 ml). The mixture was stirred at 0° C. overnight and then at room temperature for 3 h. After filtration, the filtrate was evaporated at reduced pressure. The resulting crude dibenzyl ester was dissolved in a mixture of ethyl acetate (30 ml) and methanol (30 ml) containing 10% palladium on charcoal (0.5 g) then hydrogenated at room temperature and pressure until the uptake of hydrogen ceased. The filtered solution was evaporated and the residue recrystallised from ethyl acetate to yield the tripeptide derivative.

It will be evident that following the method of the Example, and using alternative amino acids or their amides or esters, will yield other compounds of Formula 1.

Example 2

Synthesis of
Glycyl-L-2-Methyl-L-Prolyl-L-Glutamate

Scheme 1

Glycyl-L-2-Methylprolyl-L-Glutamic Acid (G-2MePE)

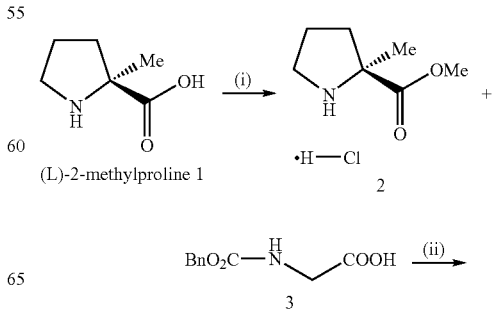

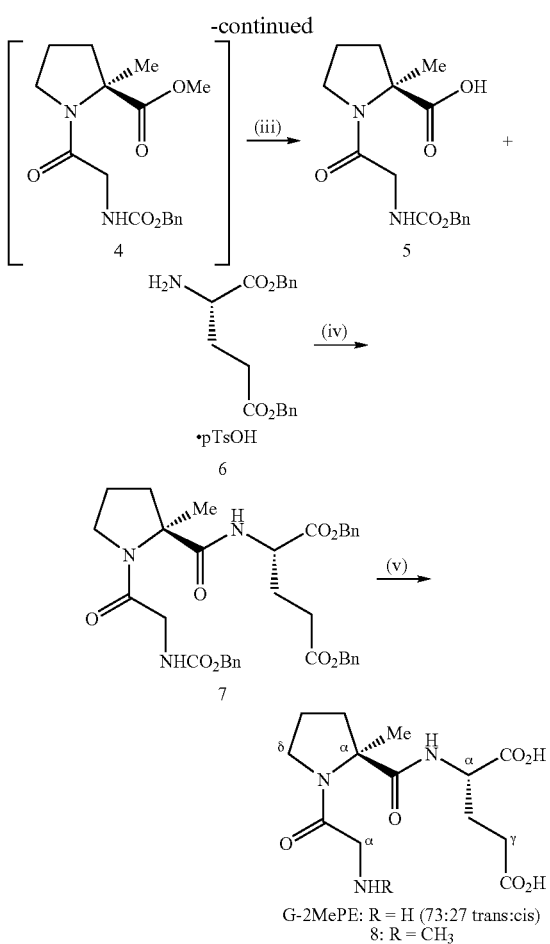

G-2MePE: R = H (73:27 trans:cis)
8: R = CH₃

Reagents, conditions and yields: (i) SOCl₂, MeOH, 79° C., N₂, 24 h (104%); (ii) Et₃N, DCC, CH₂Cl₂, 0° C. to RT, N₂, 20 h; (iii) 1 M aq. NaOH, 1,4-dioxane, 19 h (60%, 2 steps); (iv) Et₃N, BoPCl, CH₂Cl₂, RT, N₂, 17 h (89%); (v) H₂, 10% Pd/C, 91:9 MeOH—H₂O, RT, 23 h (86%).

L-2-Methylproline and L-glutamic acid dibenzyl ester p-toluenesulphonate were purchased from Bachem, N-benzyloxycarbonyl-glycine from Acros Organics and bis(2-oxo-3-oxazolidinyl)phosphinic chloride (BoPCl, 97%) from Aldrich Chem. Co.

Methyl L-2-methylprolinate hydrochloride 2

Thionyl chloride (5.84 cm³, 80.1 mmol) was cautiously added dropwise to a stirred solution of (L)-2-methylproline 1 (0.43 g, 3.33 mmol) in anhydrous methanol (30 cm³) at −5° C. under an atmosphere of nitrogen. The reaction mixture was heated under reflux for 24 h, and the resultant pale yellow-coloured solution was concentrated to dryness in vacuo. The residue was dissolved in a 1:1 mixture of methanol and toluene (30 cm³) then concentrated to dryness to remove residual thionyl chloride. This procedure was repeated twice more, yielding hydrochloride 2 (0.62 g, 104%) as an hygroscopic, spectroscopically pure, off-white solid: mp 127-131° C.; $[\alpha]_D$ −59.8 (c 0.24 in CH₂Cl₂); $\nu_{max}$ (film)/cm⁻¹ 3579, 3398 br, 2885, 2717, 2681, 2623, 2507, 1743, 1584, 1447, 1432, 1374, 1317, 1294, 1237, 1212, 1172, 1123, 981, 894, 861 and 764; $\delta_H$ (300 MHz; CDCl₃; Me₄Si) 1.88 (3H, s, Proα-CH₃), 1.70-2.30 (3H, br m, Proβ-$H_AH_B$ and Proγ-H₂), 2.30-2.60 (1H, br m, Proβ-$H_AH_B$), 3.40-3.84 (2H, br m, Proδ-H₂), 3.87 (3H, s, CO₂CH₃), 9.43 (1H, br s, NH) and 10.49 (1H, br s, HCl); $\delta_C$ (75 MHz; CDCl₃) 21.1 (CH₃, Proα-CH₃), 22.4 (CH₂, Proγ-C), 35.6 (CH₂, Proβ-C), 45.2 (CH₂, Proδ-C), 53.7 (CH₃, CO₂CH₃), 68.4 (quat., Proα-C) and 170.7 (quat., CO); m/z (FAB+) 323.1745 [M₂.H³⁵Cl.H⁺: (C₇H₁₃NO₂)₂.H³⁵Cl.H requires 323.1738] and 325.1718 [M₂.H³⁷Cl.H⁺: (C₇H₁₃NO₂)₂.H³⁷Cl.H requires 325.1708].

N-Benzyloxycarbonyl-glycyl-L-2-methylproline 5

Anhydrous triethylamine (0.45 cm³, 3.23 mmol) was added dropwise to a mixture of methyl L-2-methylprolinate hydrochloride 2 (0.42 g, 2.34 mmol) and N-benzyloxycarbonyl-glycine (98.5%) 3 (0.52 g, 2.45 mmol) in methylene chloride (16 cm³), at 0° C., under an atmosphere of nitrogen. The resultant solution was stirred for 20 min and a solution of 1,3-dicyclohexylcarbodiimide (0.56 g, 2.71 mmol) in methylene chloride (8 cm³) at 0° C. was added dropwise and the reaction mixture was warmed to room temperature and stirred for a further 20 h. The resultant white mixture was filtered through a Celite™ pad to partially remove 1,3-dicyclohexylurea, and the pad was washed with methylene chloride (50 cm³). The filtrate was washed successively with 10% aqueous hydrochloric acid (50 cm³) and saturated aqueous sodium hydrogen carbonate (50 cm³), dried (MgSO₄), filtered, and concentrated to dryness in vacuo. Further purification of the residue by flash column chromatography (35 g SiO₂; 30-70% ethyl acetate-hexane; gradient elution) afforded tentatively methyl N-benzyloxycarbonyl-glycyl-L-2-methylprolinate 4 (0.56 g), containing 1,3-dicyclohexylurea, as a white semi-solid: $R_f$ 0.65 (EtOAc); m/z (EI+) 334.1534 (M⁺. C₁₇H₂₂N₂O₅ requires 334.1529) and 224 (1,3-dicyclohexylurea).

To a solution of impure prolinate 4 (0.56 g, ca. 1.67 mmol) in 1,4-dioxane (33 cm³) was added dropwise 1M aqueous sodium hydroxide (10 cm³, 10 mmol) and the mixture was stirred for 19 h at room temperature. Methylene chloride (100 cm³) was then added and the organic layer extracted with saturated aqueous sodium hydrogen carbonate (2×100 cm³). The combined aqueous layers were carefully acidified with hydrochloric acid (32%), extracted with methylene chloride (2×100 cm³), and the combined organic layers dried (MgSO₄), filtered, and concentrated to dryness in vacuo. Purification of the ensuing residue (0.47 g) by flash column chromatography (17 g SiO₂; 50% ethyl acetate-hexane to 30% methanol-dichloromethane; gradient elution) gave N-protected dipeptide 5 (0.45 g, 60%) as a white foam in two steps from hydrochloride 2. Dipeptide 5 was shown to be exclusively the trans-orientated conformer by NMR analysis: $R_f$ 0.50 (20% MeOH—CH₂Cl₂); $[\alpha]_D$ −62.3 (c 0.20 in CH₂Cl₂); $\nu_{max}$ (film)/cm⁻¹ 3583, 3324 br, 2980, 2942, 1722, 1649, 1529, 1454, 1432, 1373, 1337, 1251, 1219, 1179, 1053, 1027, 965, 912, 735 and 698; $\delta_H$ (300 MHz; CDCl₃; Me₄Si) 1.59 (3H, s, Proα-CH₃), 1.89 (1H, 6 lines, J 18.8, 6.2 and 6.2, Proβ-$H_AH_B$), 2.01 (2H, dtt, J 18.7, 6.2 and 6.2, Proγ-H₂), 2.25-2.40 (1H, m, Proβ-$H_AH_B$), 3.54 (2H, t, J6.6, Proδ-H₂), 3.89 (1H, dd, J 17.1 and 3.9, Glyα-$H_AH_B$), 4.04 (1H, dd, J 17.2 and 5.3, Glyα-$H_AH_B$), 5.11 (2H, s, OCH₂Ph), 5.84 (1H, br t, J 4.2, N—H), 7.22-7.43 (5H, m, Ph) and 7.89 (1H, br s, —COOH); $\delta_C$ (75 MHz; CDCl₃) 21.3 (CH₃, Proα-CH₃), 23.8 (CH₂, Proγ-C), 38.2 (CH₂, Proβ-C), 43.6 (CH₂, Glyα-C), 47.2 (CH₂, Proδ-C), 66.7 (quat., Proα-C), 66.8 (CH₂, OCH₂Ph), 127.9 (CH, Ph), 127.9 (CH, Ph), 128.4, (CH, Ph), 136.4 (quat., Ph), 156.4 (quat., NCO₂), 167.5 (quat., Gly-CON) and 176.7 (quat., CO); m/z (EI+) 320.1368 (M⁺. C₁₆H₂₀N₂O₅ requires 320.1372).

Dibenzyl N-benzyloxycarbonyl-glycyl-L-2-methylprolyl-L-glutamate 7

Triethylamine (0.50 cm³, 3.59 mmol) was added dropwise to a solution of dipeptide 5 (0.36 g, 1.12 mmol) and L-glutamic acid dibenzyl ester p-toluenesulphonate 6 (0.73 g, 1.46 mmol) in methylene chloride (60 cm³) under nitrogen at room temperature, and the reaction mixture stirred for 10 min. Bis(2-oxo-3-oxazolidinyl)phosphinic chloride (BoPCl, 97%) (0.37 g, 1.41 mmol) was added and the colourless solution stirred for 17 h. The methylene chloride solution was washed successively with 10% aqueous hydrochloric acid (50 cm$^3$) and saturated aqueous sodium hydrogen carbonate (50 cm$^3$), dried (MgSO$_4$), filtered, and evaporated to dryness in vacuo. Purification of the resultant residue by repeated (2×) flash column chromatography (24 g SiO$_2$; 30-70% ethyl acetate-hexane; gradient elution) yielded fully protected tripeptide 7 (0.63 g, 89%) as a colourless oil. Tripeptide 7 was shown to be exclusively the trans-orientated conformer by NMR analysis: R$_f$ 0.55 (EtOAc); [α]$_D$ −41.9 (c 0.29 in CH$_2$Cl$_2$); ν$_{max}$ (film)/cm$^{-1}$ 3583, 3353 br, 2950, 1734, 1660, 1521, 1499, 1454, 1429, 1257, 1214, 1188, 1166, 1051, 911, 737 and 697; δ$_H$ (400 MHz; CDCl$_3$; Me$_4$Si) 1.64 (3H, s, Proα-CH$_3$), 1.72 (1H, dt, J 12.8, 7.6 and 7.6, Proβ-H$_A$H$_B$), 1.92 (2H, 5 lines, J6.7, Proγ-H$_2$), 2.04 (1H, 6 lines, J 7.3 Gluβ-H$_A$H$_B$), 2.17-2.27 (1H, m, Gluβ-H$_A$H$_B$), 2.35-2.51 (3H, m, Proβ-H$_A$H$_B$ and Gluγ-H$_2$), 3.37-3.57 (2H, m, Proδ-H$_2$), 3.90 (1H, dd, J 17.0 and 3.6, Glyα-H$_A$H$_B$), 4.00 (1H, dd, J 17.1 and 5.1, Glyα-H$_A$H$_B$), 4.56 (1H, td, J 7.7 and 4.9, Gluα-H), 5.05-5.20 (6H, m, 3×OCH$_2$Ph), 5.66-5.72 (1H, br m, Gly-NH), 7.26-7.37 (15H, m, 3×Ph) and 7.44 (1H, d, J 7.2, Glu-NH); δ$_C$ (100 MHz; CDCl$_3$) 21.9 (CH$_3$, Proα-CH$_3$), 23.4 (CH$_2$, Proγ-C), 26.6 (CH$_2$, Gluβ-C), 30.1 (CH$_2$, Gluγ-C), 38.3 (CH$_2$, Proβ-C), 43.9 (CH$_2$, Glyα-C), 47.6 (CH$_2$, Proδ-C), 52.2 (CH, Gluα-C), 66.4 (CH$_2$, OCH$_2$Ph), 66.8 (CH$_2$, OCH$_2$Ph), 67.1 (CH$_2$, OCH$_2$Ph), 68.2 (quat, Proα-C), 127.9 (CH, Ph), 128.0 (CH, Ph), 128.1, (CH, Ph), 128.2, (CH, Ph), 128.2, (CH, Ph), 128.3, (CH, Ph), 128.4, (CH, Ph), 128.5, (CH, Ph), 128.5, (CH, Ph), 135.2 (quat., Ph), 135.7 (quat., Ph), 136.4 (quat., Ph), 156.1 (quat., NCO$_2$), 167.3 (quat., Gly-CO), 171.4 (quat., CO), 172.9 (quat., CO) and 173.4 (quat., CO); m/z (FAB+) 630.2809 (MH$^+$. C$_{35}$H$_{40}$N$_3$O$_8$ requires 630.2815).

Glycyl-L-2-methylprolyl-L-glutamic acid (G-2MePE)

A mixture of the protected tripeptide 7 (0.63 g, 1.00 mmol) and 10 wt. % palladium on activated carbon (0.32 g, 0.30 mmol) in 91:9 methanol-water (22 cm$^3$) was stirred under an atmosphere of hydrogen at room temperature, protected from light, for 23 h. The reaction mixture was filtered through a Celite™ pad and the pad washed with 75:25 methanol-water (200 cm$^3$). The filtrate was concentrated to dryness under reduced pressure and the residue triturated with anhydrous diethyl ether to afford a 38:1 mixture of G-2MePE and tentatively methylamine 8 (0.27 g, 86%) as an extremely hygroscopic white solid. Analytical reverse-phase HPLC studies on the mixture (Altech Econosphere C$_{18}$ Si column, 150×4.6 mm, 5 μm; 5 min flush with H$_2$O (0.05% TFA) then steady gradient over 25 min to MeCN as eluent at flow rate of 1 m/min; detection using diode array] indicated it was a 38:1 mixture of two eluting peaks with retention times of 13.64 and 14.44 min at 207 and 197 nm, respectively. G-2MePE was shown to be a 73:27 trans:cis mixture of conformers by $^1$H NMR analysis (the ratio was estimated from the relative intensities of the double doublet and triplet at δ 4.18 and 3.71, assigned to the Gluα-H protons of the major and minor conformers, respectively): mp 144° C.$^Φ$; [α]$_D$ −52.4 (c 0.19 in H$_2$O); δ$_H$ (300 MHz; D$_2$O; internal MeOH) 1.52 (3H, s, Proα-CH$_3$), 1.81-2.21 (6H, m, Proβ-H$_2$, Proγ-H$_2$ and Gluβ-H$_2$), 2.34 (1.46H, t, J 7.2, Gluγ-H$_2$), 2.42* (0.54H, t, J 7.3, Gluγ-H$_2$), 3.50-3.66 (2H, m, Proδ-H$_2$), 3.71* (0.27H, t, J 6.2, Gluα-H), 3.85 (1H, d, J 16.6, Glyα-H$_A$H$_B$), 3.92 (1H, d, J 16.6, Glyα-H$_A$H$_B$) and 4.18 (0.73H, dd, J 8.4 and 4.7, Gluα-H); δ$_C$ (75 MHz; D$_2$O; internal MeOH) 21.8 (CH$_3$, Proα-CH$_3$), 25.0 (CH$_2$, Proγ-C), 27.8* (CH$_2$, Gluβ-C), 28.8 (CH$_2$, Gluβ-C), 32.9 (CH$_2$, Gluγ-C), 40.8 (CH$_2$, Proβ-C), 42.7 (CH$_2$, Glyα-C), 49.5 (CH$_2$, Proδ-C), 56.0* (CH, Gluα-C), 56.4 (CH, Gluα-C), 69.8 (quat, Proα-C), 166.5 (quat., Gly-CO), 177.3 (quat., Pro-CON), 179.2 (quat., Gluα-CO), 180.2* (quat., Gluγ-CO) and 180.6 (quat., Gluγ-CO); m/z (FAB+) 316.1508 (MH$^+$. C$_{13}$H$_{22}$N$_3$O$_6$ requires 316.1509).

Example 3

In Vitro Neuroprotection

Therapeutic effects of GPE analogues were examined in a series of experiments in vitro to determine their effects neurodegeneration of neural cells of different origin. The in vitro systems described herein are well-established in the art and are known to be predictive of neuroprotective effects observed in vivo, including effects in humans suffering from neurodegenerative disorders.

Material and Methods

The following experimental protocol followed guidelines approved by the University of Auckland Animal Ethics Committee.

Preparation of Cortical Astrocyte Cultures for Harvest of Metabolised Cell Culture Supernatant One cortical hemisphere from a postnatal day 1 rat was used and collected into 4 ml of DMEM. Trituration was performed using a 5 ml glass pipette and an 18-gauge needle. The cell suspension was sieved through a 100 μm cell strainer and washed in 50 ml DMEM (centrifugation for 5 min at 250 g). The sediment was resuspended in 20 ml DMEM+10% fetal calf serum. The suspension was added into two 25 cm$^3$ flasks (10 ml per flask) and cultivated at 37° C. in the presence of 10% CO$_2$ followed by a change of the medium twice a week. When cells reached confluence, they were washed three times with PBS, adjusted to Neurobasal/B27 and incubated for another 3 days. This supernatant was frozen for transient storage at −80° C.

Preparation of Stratial and Cortical Tissue from Rat E18/E19 Embryos

A dam was sacrificed by CO$_2$-treatment, and then was prepared for caesarean section. After surgery, the embryos were removed from their amniotic sacs and decapitated. The heads were placed on ice in DMEM/F12 medium for striatum and PBS+0.65% D(+)-glucose for cortex.

Striatal Tissue Extraction Procedure and Preparation of Cells

A whole brain was removed from the skull with the ventral side facing upwards in DMEM/F12 medium. The striatum was dissected out from both hemispheres under a stereomicroscope and the striatal tissue was placed into a Falcon tube on ice. Striatal tissue was then triturated using a P1000 pipettor in 1 ml of volume. The tissue was triturated by gently pipetting the solution up and down into the pipette tip about 15 times, using shearing force on alternate outflows. The tissue pieces settled to the bottom of the Falcon tube within 30 seconds. The supernatant containing a suspension of dissociated single cells was then transferred to a new sterile Falcon tube on ice. The tissue pieces were triturated again to avoid excessively damaging already dissociated cells, by over triturating them. 1 milliliter of ice-cold DMEM/F12 medium was added to the tissue pieces in the first tube and triturated as before. The tissue pieces were allowed to settle and the supernatant was removed to a new sterile Falcon tube on ice. The cells were centrifuged at 250 g for 5 minutes at 4° C.

Plating and Cultivation of Striatal Cells

Striatal cells were plated into Poly-L-Lysine (0.1 mg/ml) coated 96-well plates (the inner 60 wells only) at a density of 200,000 cells/cm$^2$ in Neurobasal/B27 medium (Invitrogen). The cells were cultivated in the presence of 5% $CO_2$ at 37° C. under 100% humidity. Medium was changed on days 1, 3 and 6.

Cortical Tissue Extraction Procedure and Preparation of Cells

The two cortical hemispheres were carefully removed by spatula from the whole brain with the ventral side facing upside into a PBS +0.65%D(+)-glucose containing petri dish. Forceps were put into the rostral part (near *B. olfactorius*) of the cortex in order to fix the tissue and two lateral-sagittal oriented cuts were made to remove the paraform and entorhinal cortices. A frontal oriented cut at the posterior end was made to remove the hippocampal formation. A final frontal cut was done a few millimetres away from the last cut in order to get hold of area 17/18 of the visual cortex.

Cortices were placed on ice in PBS+0.65%(+)-glucose and centrifuged at 350 g for 5 minutes. The supernatant was removed and trypsin/EDTA (0.05%/0.53 mM) was added for 8 min at 37° C. The reaction was stopped by adding an equal amount of DMEM and 10% fetal calf serum. The supernatant was removed by centrifugation followed by two subsequent washes in Neurobasal/B27 medium.

The cells were triturated once with a glass Pasteur pipette in 1 ml of Neurobasal/B27 medium and subsequently twice by using a 1 ml insulin syringe with a 22 gauge needle. The cell suspension was passed through a 100 μm cell strainer and rinsed by 1 ml of Neurobasal/B27 medium. Cells were counted and adjusted to 50,000 cells per 60 μl.

Plating and Cultivation of Cortical Cells 96-well plates were coated with 0.2 mg/ml Poly-L-Lysine and subsequently coated with 2 μg/ml laminin in PBS, after which 60 μl of cortical astrocyte-conditioned medium was added to each well. Subsequently, 60 μl of cortical cell suspension was added. The cells were cultivated in the presence of 10% $CO_2$ at 37° C. under 100% humidity. At day 1, there was a complete medium change (1:1—Neurobasal/B27 and astrocyte-conditioned medium) with addition of 1 μM cytosine-β-D-arabino-furanoside (mitosis inhibitor). On days 2 and 5, ⅔ of the medium was changed.

Cerebellar Microexplants From P8 Animals: Preparation, Cultivation and Fixation

Laminated cerebellar cortices of the two hemispheres were explanted from a P8 rat, cut into small pieces in PBS +0.65% D(+) glucose solution and triturated with a 23 gauge needle and subsequently pressed through a 125 μm pore size sieve. The obtained microexplants were centrifuged (60 g) twice (media change) into serum-free BSA-supplemented STARTV-medium (Biochrom). For cultivation, 40 μl of cell suspension was adhered for 3 hours on a 0.1 mg/ml Poly-L-Lysine coated cover slip placed in 35 mm sized 6 well plates in the presence of 5% $CO_2$ under 100% humidity at 34° C. Subsequently, 1 ml of STARTV-medium was added together with the toxins and drugs. The cultures were monitored (evaluated) after 2-3 days of cultivation in the presence of 5% $CO_2$ under 100% humidity. For cell counting analysis, the cultures were fixed in rising concentrations of paraformaldehyde (0.4%, 1.2%, 3% and 4% for 3 min each) followed by a wash in PBS.

Toxin and drug administration for cerebellar cortical and striatal cells; analysis To study neuroprotective effects of GPE analogues, we carried out a series of experiments in vitro using okadaic acid to cause toxic injury to neural cells. Okadaic acid is an art-recognized toxin that is known to cause injury to neurons. Further, recovery of neural cells or neural cell function after injury by okadaic acid is recognized to be predictive of recoveries from injuries caused by other toxins.

To cause toxic injury to neurons, we exposed neurons to 1:100 parts of okadaic acid at concentrations of 30 nM or 100 nM and 0.5 mM 3-nitropropionic acid (for cerebellar microexplants only). GPE (1 nM-1 mM) or G-2MePE (1 nM-1 mM) was used at 8 days in vitro (DIV) for cortical cultures and 9DIV for striatal cultures. The incubation time was 24 hours. The survival rate was determined by a colorimetric end-point MTT-assay at 595 nm in a multi-well plate reader. For the cerebellar microexplants four windows (field of 0.65 mm$^2$) with highest cell density were chosen and cells displaying neurite outgrowth were counted.

Results

The GPE analogue G-2MePE exhibited comparable neuroprotective effects within all three tested in vitro systems (FIGS. 12-15).

Cortical cultures responded to 10 μM concentrations of GPE (FIG. 12) or G-2MePE (10 μM, FIG. 13) with 64% and 59% neuroprotection, respectively.

Figure 14:
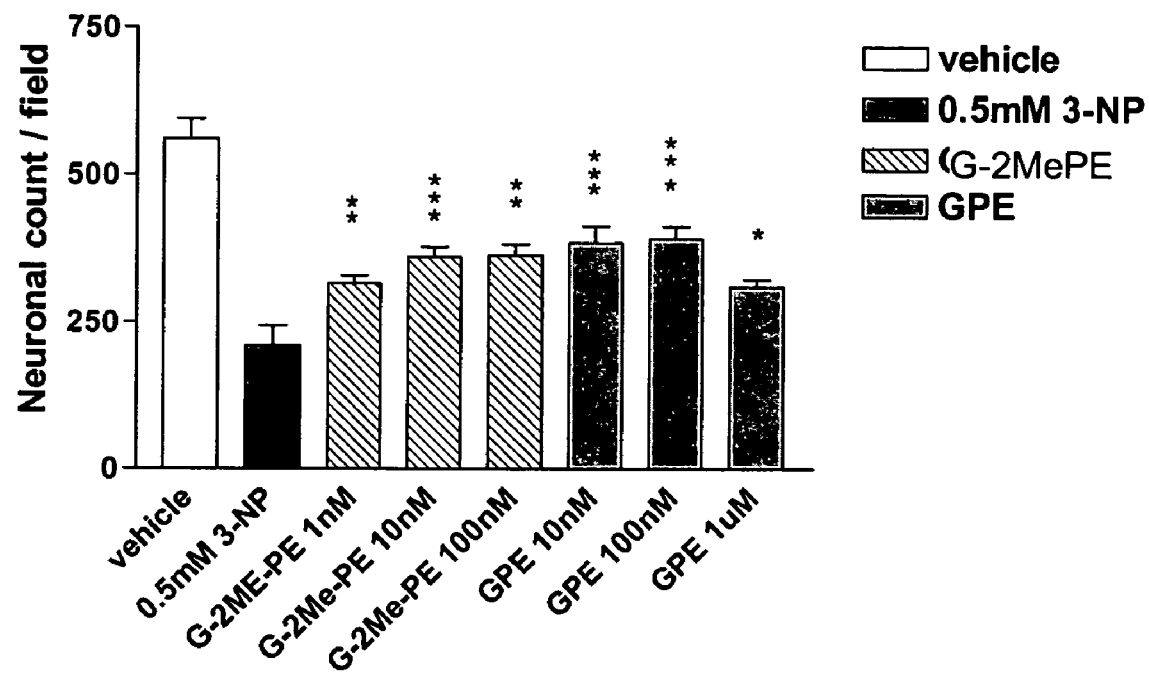
Figure 15:
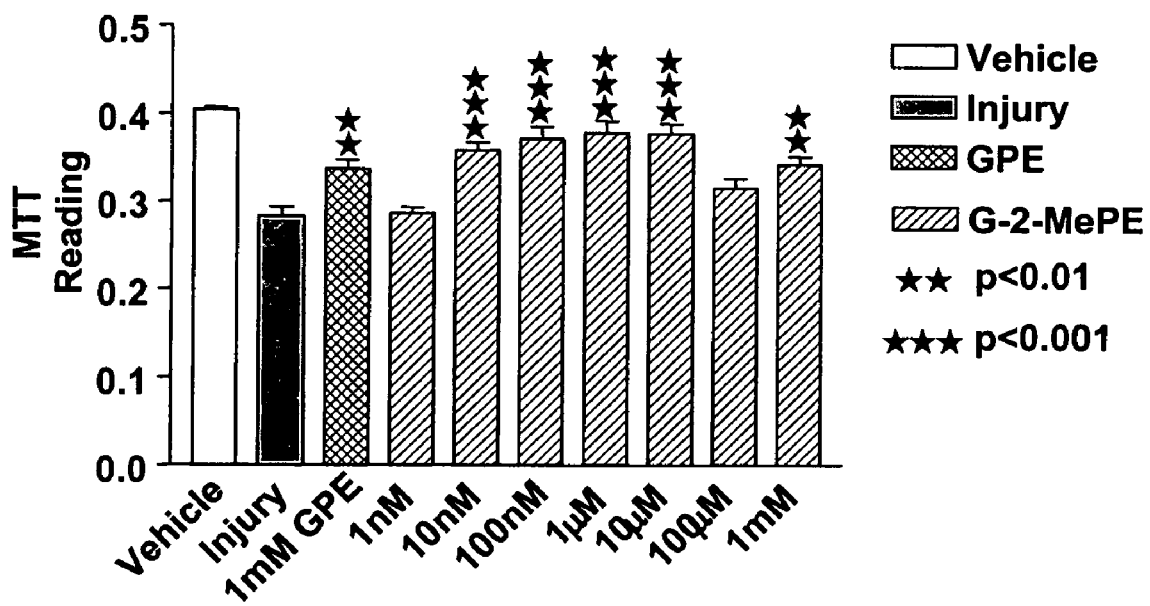

The other 2 types of cultures demonstrated neuroprotection at lower doses of G-2MePE (cerebellar microexplants: FIG. 14 and striatal cells: FIG. 15). Striatal cells demonstrated neuroprotection within the range of 1 nM to 1 mM of G-2MePE (FIG. 15), while the postnatal cerebellar microexplants demonstrated neuroprotection with G-2MePE in the dose range between about 1 nM and about 100 nM (FIG. 14). Thus, we conclude that G-2MePE is a neuroprotective agent and can have therapeutic effects in humans suffering from neurodegenerative disorders.

Example 4

Effect of G2MePE Following Hypoxic-Ischaemic (HI) Injury

To determine whether G-2MePE can be useful for treating hypoxia or ischemia, we undertook a series of studies in vivo in adult rats. Adult rats are well known system for studying neurological and pathophysiological conditions, and therefore are predictive of such effects in humans.

Methods and Materials

These studies were approved by the Animal Ethics Committee of the University of Auckland. Every effort was made to minimize animal suffering and to reduce the number of animals used.

G-2MePE was synthesized by the Department of Medicinal Chemistry, University of Auckland using a solid phase synthesis process and stored at −20C. G-2MePE was dissolved in normal saline before the treatment.

Groups of HI injured rats were given a continuous 4 h i.v. infusion (0.3 mg/kg/h) of G-2MePE or saline beginning 1 h after HI injury (treatment window 1-5 h post injury). After 5 days the rats were killed and the brains collected for histological analysis. Any rats that showed prolonged seizure activity or were considered to be suffering unnecessarily were euthanised prior to the end of the study in accordance with the University of Auckland's Animal Ethics Committees guidelines. Any rats that died during the HI procedure, and were therefore not treated with drug, were omitted from the study.

Experimental Procedures

Procedure for Induction of Unilateral Brain Damage

Adult male Wistar rats (280-310 g) were obtained from the Animal Resources Unit colony, University of Auckland. Acute brain injury was induced using the modified Levine preparation and (Guan et al., 1993). The conscious rat HI model is considered to be an excellent animal model of hypoperfusion injury that is often associated with heart failure or following cardiac bypass surgery. Hypoxic-ischaemic brain injury was induced by unilateral carotid artery ligation followed by inhalation asphyxia. The right carotid artery was double ligated under general aneathesia (3% halothane/oxygen). After 1 h recovery from the anaesthesia the rats were placed in an incubator where the humidity (90±5%) and temperature (31±0.5° C.) were controlled for a further 1 h. The rats were then exposed to 15 min hypoxia (6±0.2% oxygen). The animals were maintained in the incubator for a further 30 min after the hypoxia.

Rats had previously been chronically catheterized to allow treatments to be administered by continuous i.v. infusion 3 days prior to the experiment as described earlier by Thomas et al. (1997), herein expressly incorporated fully by reference. Briefly rats were surgically fitted with an indwelling jugular venous catheter and housed individually in metabolic cages. The surgery was conducted under general anaesthesia with 3% halothane/oxygen, where the right jugular vein was exposed and a polyethylene catheter inserted. The catheter were exteriorized and passed out of the cage via a protective stainless steel spring and connected with a fluid-tight swivel joint. This was to allow the animal free movement within the cage. After a 3 day post-surgery recovery period, the catheter was connected to a peristaltic infusion pump to facilitate the infusion of G-2MePE or saline.

All rats were monitored regularly throughout the experiment by staff who were blinded to the treatment codes. Treatment groups were defined according to Table 1 below.

TABLE 1

| Treatment Group | Treatment groups | |
|---|---|---|
| | Number of rats used | Number of rats that died after treatment |
| Saline controls | 28 | 9 |
| G-2MePE (1-5 h) | 25 | 0 |

Histological Evaluation

The histological procedures have been previously described (Guan et al., 1993; Guan et al., 1996). Briefly, 5 days after HI injury and G-2MePE treatment the rats were perfused transcardially under deep anaesthesia with normal saline followed by 10% formalin. The brains were kept in the same fixative for 2 days before being processed using a paraffin procedure. Three coronal (6 μm) sections were cut from the striatum, cerebral cortex and hippocampus, mounted on glass slides and stained with thionine and acid fuchsin.

Dead neurons were identified as those with acidophilic (red) cytoplasm and contracted nuclei (Auer et al., 1985; Brown and Brierley, 1972). Brain tissues with selective neuronal death, cellular reaction and/or pan-necrosis were considered damaged (Guan et al., 2000; Markgraf et al., 1993). The severity of brain damage in the lateral cortex assessed using three levels, the dentate gyrus and the CA1-2, 3 and 4 sub-regions of the hippocampus using two levels, and the striatum using one level was scored as following: 0=no damage; 1=<5% tissue damaged; 2=<50% tissue damaged; 3=>50% tissue damaged and 4=>95% damaged (Guan et al., 2000; Lundgren et al., 1992). The average tissue damage scores in different brain regions were used for data analysis (Guan et al., 2000).

Statistical Analysis

Histological data were analyzed in two ways. First we used two-way ANOVA to compare G-2MePE- and saline-treated groups. To compare seizure-related fatalities (all in vehicle-treated group) with the drug effect relating to the histological scoring, we applied the Kruskal-Wallis non-parametric test followed by pair-wise comparisons using the Dunn's multiple comparison test. Data are presented as mean±SEM.

Results

Treatment Studies

HI brain injury resulted in severe neuronal injury in the ligated right hemisphere 5 days after HI injury. Massive neuronal loss was seen in all sub-regions of the hippocampus. A mixture of selective neuronal loss, tissue pan-necrosis and cellular reaction were found in the cerebral cortex, all sub-regions of the hippocampus, the dentate gyrus and the striatum. There was no neuronal loss in uninjured contralateral left hemisphere.

Nine out of 28 saline-treated control rats showed seizures generally beginning 3 h after HI injury. If no recovery was seen in these rats after 24 h they were euthanized to minimize their suffering and abide by AEC guidelines. Because the pattern of brain damage following HI injury has been shown to vary with time, rats killed (generally 24-48 h after injury) before the end of the experiment at day 5 were analyzed as a separate group from non-seizure control rats. None of the 25 rats treated with G-2MePE showed any seizure activity and all survived to the end of the experiment at day 5.

Figure 16A:
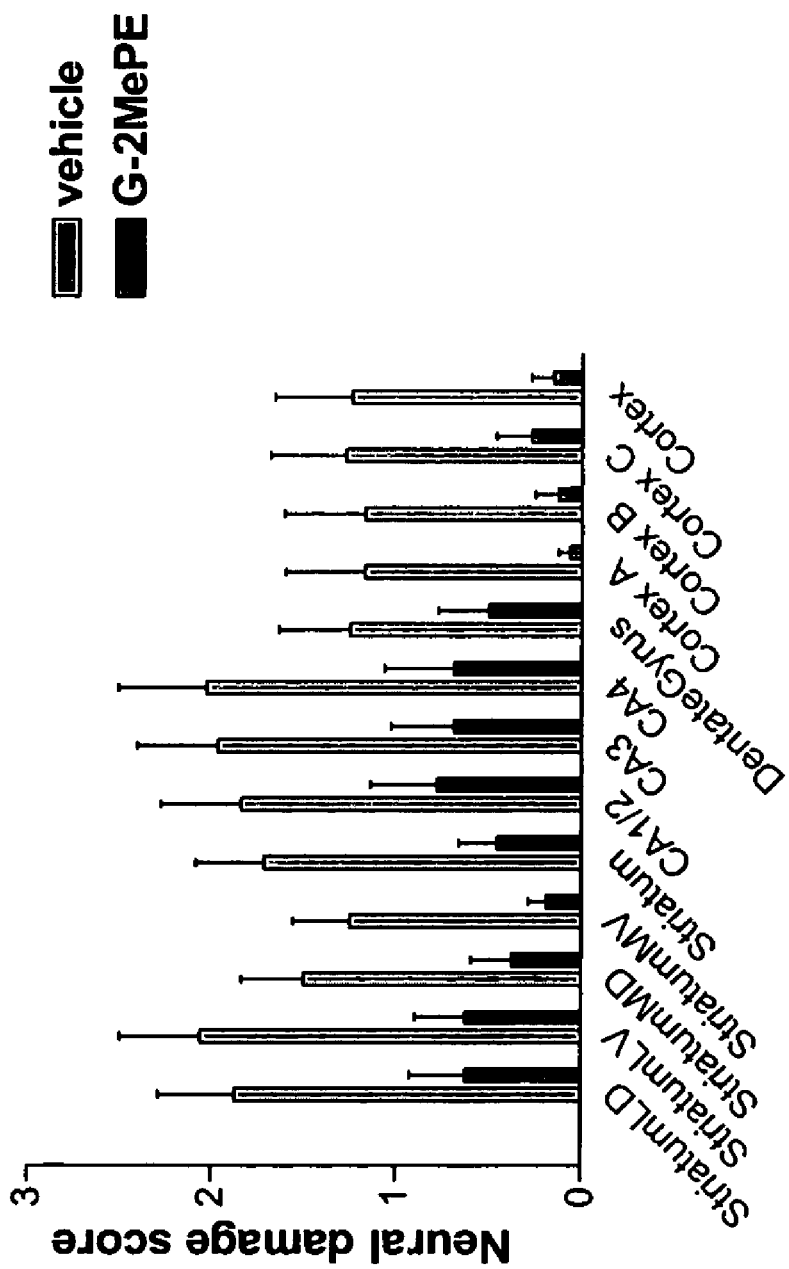
FIGS. 16A-16B show the effects of a 4 h continuous intravenous (i.v.) infusion of 0.3 mg/kg G-2MePE administered 1 h after HI injury in animals treated.
Figure 16B:
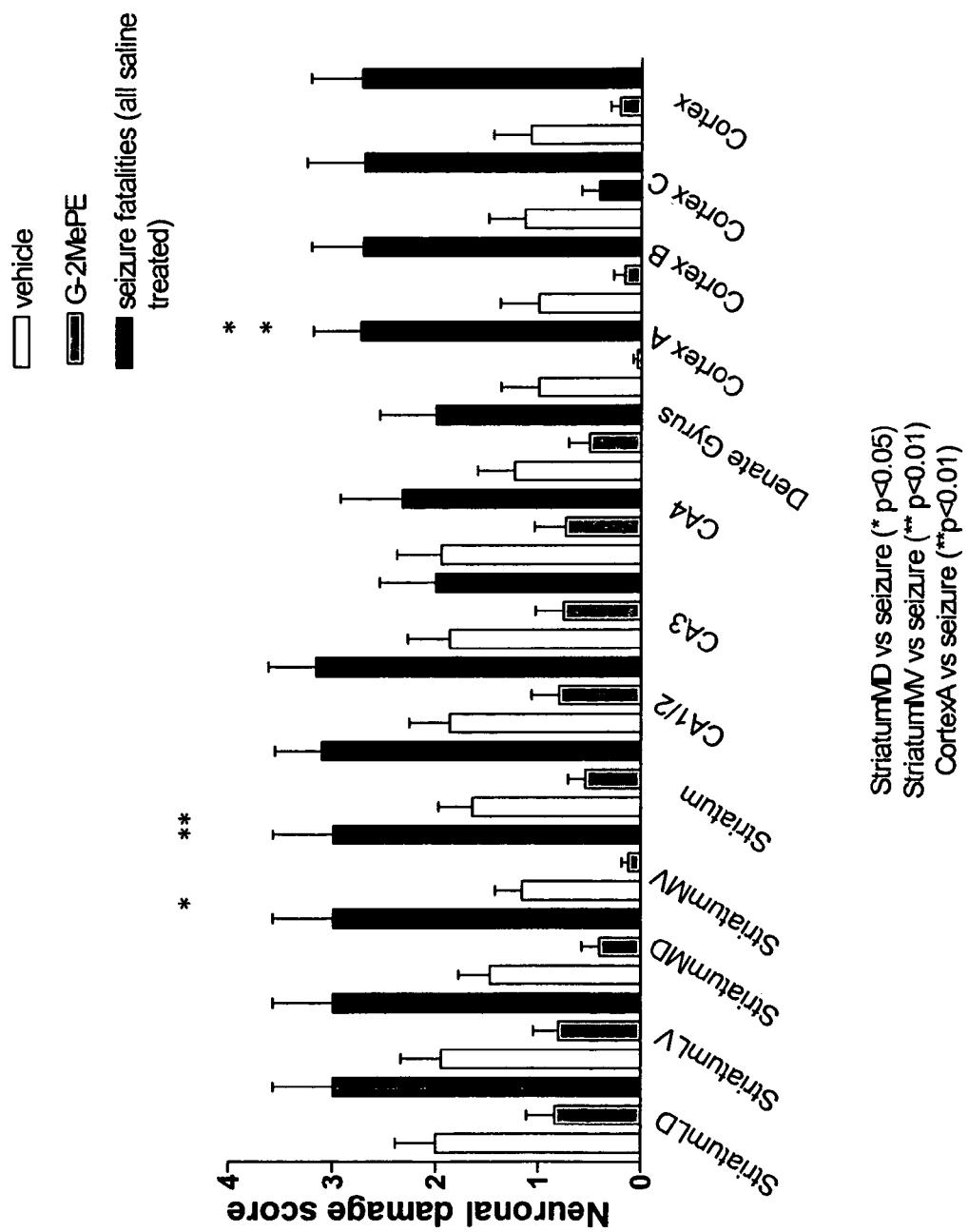

In animals treated with a 4 h continuous i.v. infusion of 0.3 mg/kg G-2MePE 1 h after HI injury there was a highly significant reduction (overall $P<0.001$) in the tissue damage in the injured right hemisphere when compared with the saline-treated control group (FIG. 16A). Post-hoc analysis (Dunn) showed that G-2MePE treatment significantly reduced ($P<0.01$) the tissue damage in 2 different striatal areas (medio-ventrial ($p<0.05$) and medio-dorsal ($p<0.01$)) and one cortical area ($p<0.05$) when compared with control rats that displayed post-ischaemic seizure activity (FIG. 16B).

This study demonstrated that G-2MePE exhibits potent neuroprotective effects when given as a continuous 4 h i.v. infusion in adult rats 1-5 h after HI brain injury. In addition, G-2MePE may also be effective in blocking post-ischaemic seizure activity. We conclude from these studies that G-2MePE is neuroprotective and can be a useful agent in therapy of a neurodegeneration caused by hypoxia/ischemia. Further, because these studies were carried out in an animal system that is predictive of therapeutic effects in humans, G-2MePE is a good candidate for use in humans to treat neurodegeneration caused by hypoxia/ischemia, such as that caused by cardiac bypass graft surgery.

Example 5

Effects of G2MePE on Animals With Stroke

To determine whether G-2MePE might be a suitable therapeutic with applications for treating stroke, we carried out a series of studies in an art-recognized model of stroke in rats, namely, middle coronary artery occlusion (MCAO). This system is known to mimic neurological and behavioural signs and symptoms of stroke in humans, and therefore, the results obtained are predictive of therapeutic effects in humans with strokes. We measured infarct size, and the appearance of GFAP-positive astrocytes and microglial cell activation, both of which are recognized in the art as being indicators of brain damage. Thus, results obtained using GFAP and microglial cell activation are indicative of stroke in human beings and reductions in GFAP staining and microglial cell activation are predictive of therapeutic effects in humans suffering from stroke.

Materials and Methods

Endothelin-1 Induced Middle Cerebral Artery Occlusion

All surgical and experimental procedures carried out in this study had been approved by the University of Auckland Animal Ethics Committee. All efforts were made to minimise any animal suffering and the number of animals used. Adult male Sprague-Dawley rats (280-350 g) were used.

An inhalation anaesthetic (halothane) was co-administered with oxygen to anaesthetise the rats. Initially 5% halothane/oxygen was applied to anaesthetise the animal, and then 2.5% halothane was used to maintain the anaesthesia. Once under anaesthesia, a guide cannula was implanted on the skull of the anaesthetized rats, which was fixed into position with dental cement. Following this implantation, the jugular vein of the animal was also cannulated. Three days post cannula implantation and cannulation, the rats were anaesthetized again as above and subjected to MCA occlusion according to the method of Sharkey and co-workers (Sharkey et al., 1993). This involved placing the head of each rat on a stereotaxic frame and locking it into position. The animals were also placed on a heating pad, which is designed to maintain body temperature within the physiological range for the duration of the surgical procedure.

The hair over the scalp was clipped short with a pair of scissors, sponged and wiped dry with a solution of Betadine® (iodine). Following this, a midline skin incision was made through the scalp to expose the coronal suture line (bregma) of the skull prior to a small opening being drilled through the cranial bone using the following co-ordinates 0.2 mm anterior to and 5.2 mm lateral to bregma. Through the guide cannula, a 28-gauge infusion needle that was connected to a 10 μl syringe containing 100 pmol of porcine endothelin-1 (Et-1; Sigma-Aldrich Inc., Saint Louis, Mo., USA) in 3 μl of saline was vertically inserted to a depth of 8.7 mm below the surface of the skull. At a delivery rate of 1 μl per minute, a total volume of 3 μl of solution was manually infused over the period of three minutes. With the completion of the infusion, the needle was left in place for five more minutes before being withdrawn from the brain whilst the skin incision was sutured and the animals moved to a warmed incubator (37° C.) in order to recover from the surgery. Once awake, the animals were then transferred to their cages where they had full access to both food and water.

GPE and G-2MePE Treatment

At five hours post Et-1 (100 pmol) injection, GPE (3 mg/kg/h) (Bachem AG, Basal, Switzerland) or succinate buffer (vehicle treated group) in the first study and G-2MePE (0.3 mg/kg/h) (Neuren Pharmaceuticals Ltd, New Zealand) or succinate buffer (vehicle treated group) in the second study was continuously infused i.v. into the animal via the jugular vein cannula at a delivery rate of 0.5 ml/h for four hours.

Histological Procedures

Five days following the drug treatment, the animals were sacrificed using an overdose of sodium pentobarbital and the brains collected for histological evaluation of neuronal survival. The rats were perfused transcardially with 0.9% normal saline followed by 10% formalin. The brain was removed from the skull and stored in the same fixative solution for at least 24 hours. Three 2 mm coronal sections using a rodent brain matrix (RBM-3000C/RBM-4000C, ASI Instruments, USA) were cut. Section A: directly in front of the optical chiasma, section B: directly following section A posterior to the optical chiasma and section C directly following section B. The slices were held in 10% formalin for at least 24 hours, processed in increasing percentage of alcohol and in chloroform and embedded in paraffin for further cutting. At a thickness of 8 μm, coronal sections were cut on a Leica® microtome (Leica Instruments, Nussloch, Germany), mounted onto Polysine™ microscope coated slides (BioLab Scientific, NZ) and stained with thionin-acid fuchsin prior to microscopic evaluation.

Immunohistochemistry

Eight-micron thickness paraffin-embedded sections were mounted to microscope slides, dewaxed in xylene and brought up to water through the standard graded ethanol procedure. These slides were then washed three times for five minutes (3×5 min) in 0.1 M phosphate buffered saline (PBS), before being transferred to a solution of 1% $H_2O_2$ in absolute methanol for 30 minutes at room temperature in order to block for endogenous peroxidases. Following another conventional wash, non-specific protein binding was blocked with 2% normal horse serum (NHS) (Vector Laboratories Inc., Burlingame, Calif., USA) in 0.1M PBS at room temperature for an hour. After this time period, the NHS was drained away carefully and the respective primary antibodies were loaded onto the sections.

For astrocytic immunostaining, glial fibrillary acidic protein (GFAP) was used as a marker. These sections were incubated with a primary monoclonal anti-GFAP (Sigma-Aldrich Inc., Saint Louis, Mo., USA) antibody from mouse at a dilution of 1:1000 in 0.1M PBS containing 2% NHS overnight at 4° C. in a humidified chamber. The primary antibody was washed off the next day with 0.1M PBS (3×5 min) and the section was incubated with horse-anti-mouse biotinylated secondary antibody (1:200, Vector Laboratories Inc., Burlingame, Calif., USA) in 0.1M PBS plus 2% NHS overnight at 4° C. in a humidified chamber. The antibody was washed off the following day and the section incubated with ExtrAvidin peroxidase conjugate (1:500, Sigma) in 0.1M PBS plus 2% NHS at room temperature. After three hours, the slides were washed and developed with DAB for the required time until a brown reaction product was observed.

For microglial immunostaining, isolectin $B_4$ peroxidase labelled from *Bandeiraea simplicifolia* (Sigma-Aldrich Inc., Saint Louis, Mo., USA) was used as a marker. With the only exception of using 0.1M Tris-buffered saline (TBS) plus 0.2% triton as opposed to 0.1M PBS, these sections went through the exact similar protocol to that required for immunolabelling of GFAP. However, in this assay, there was no blocking for non-specific protein binding. Therefore, following the blocking for endogenous peroxidases step, a standard wash (3×5 min) in TBS plus 0.2% triton was carried out prior to the sections being loaded with reconstituted isolectin $B_4$ (10 μg/ml). The slides were incubated overnight at 4° C. in a humidified chamber. After 24 hours, the isolectin $B_4$ was washed off and sections developed with DAB for the required time until a brown reaction product was noticeable.

The time required for DAB colour development was controlled to be equal for all sections within both studies. Following DAB colour development, the stained sections were dehydrated through the standard increasing ethanol gradient and xylene procedure. Finally the slides were quickly allowed to air dry, mounted using DPX mounting medium and coverslipped.

Image Analysis

Slides were visualised under bright-field illumination and the extent of neuronal damage, as well as the astrocytic and microglial responses were analysed on a Carl Zeiss Axioskope™ microscope using AxioVision™ software (AxioVision 3.0, Carl Zeiss Software, Hallbergmoos, Germany). For analysis of GFAP immunohistochemistry, the area of total GFAP immunostaining in the peri-infarct zone was calculated in mm² and converted into a percentage against the total area (in mm²) of the ipsilateral (injured) hemisphere, whilst for isolectin $B_4$, the microglial immunopositive cells were counted in three screen fields (×10 magnification) and then averaged. Also, in every experiment, a control section with no primary antibody was used as a negative control. Furthermore, the histology and immunohistochemistry was analysed by an individual blinded to the treatment groups.

Statistical Analysis

Student t-test was used for comparing the treatment effects of GPE and G-2MePE to its vehicle groups, respectively. All statistical calculations were carried out using GraphPad Prism™ software (Version 3.02, GraphPad Software Inc., San Diego, Calif., USA). Data are presented as mean±S.E.M. and significance was defined at $p<0.05$.

Results

Effect of GPE and G-2MePE on Infarct Size

Figure 17:
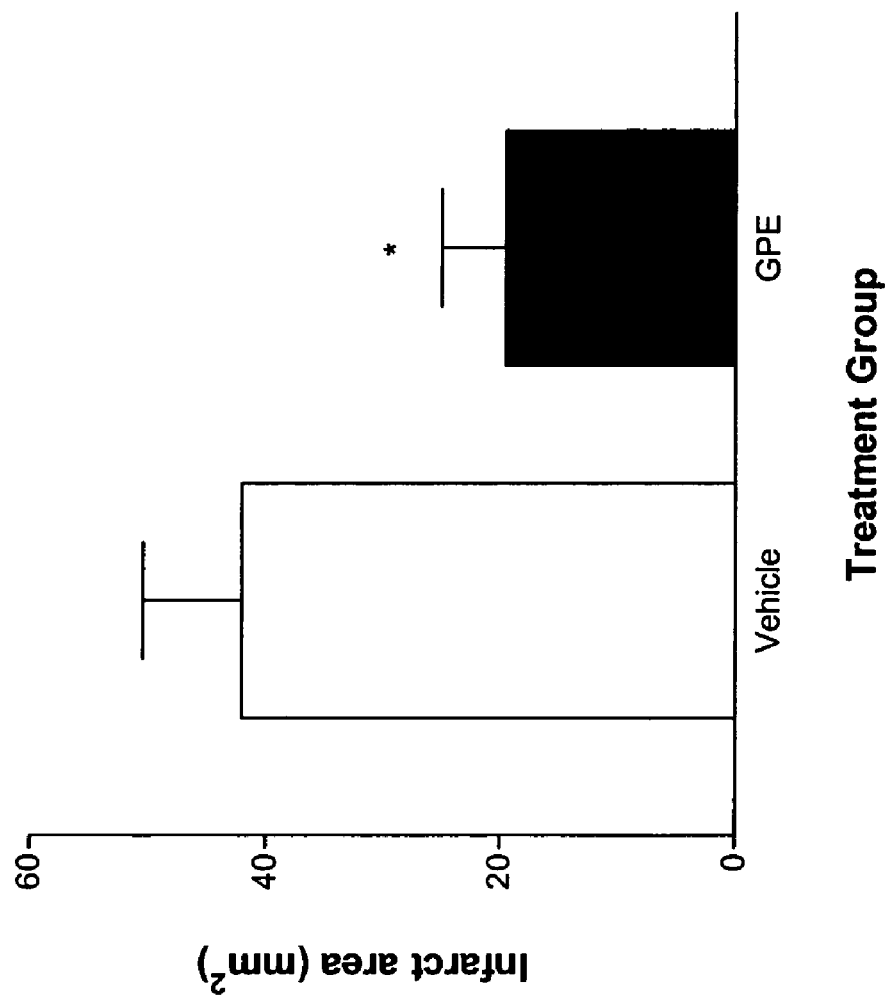
FIG. 17 shows the effect of delayed administration of GPE or vehicle treatment on area of infarct (in $mm^2$) following an Et-1 MCAO model. Five hours post Et-1 injection, GPE-treated (3 mg/kg/h) (■, n=15) or vehicle-treated (succinate buffer) (□, n=14) animals were continuously infused i.v. via the jugular vein at 0.5 ml/h for four hours. Data are presented as mean±S.E.M. and significance was defined at $p<0.05$.
Figure 18:
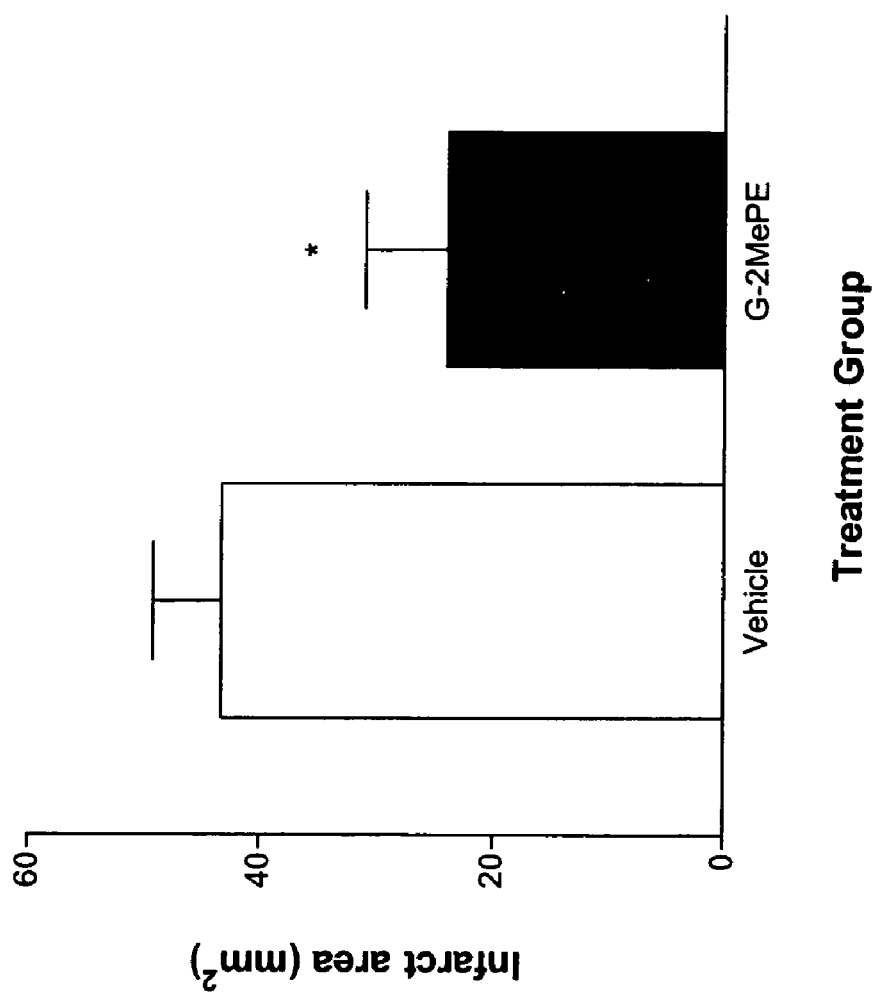
FIG. 18 shows the effect of delayed administration of G-2MePE or vehicle treatment on area of infarct (in $mm^2$) following an Et-1 MCAO model. Five hours post Et-1 injection, G-2MePE -treated (0.3 mg/kg/h) (■, n=14) or vehicle-treated (succinate buffer) (□, n=13) animals were continuously infused i.v. via the jugular vein at 0.5 ml/h for four hours. Data are presented as mean±S.E.M. and significance was defined at $p<0.05$.

In the GPE study, the area of infarct in animals treated with vehicle was 42.0±8.4 mm² (n=14, FIG. 17). Treatment with GPE (3 mg/kg/h) significantly reduced the area of the infarct to 19.6±5.4 mm² when compared to its vehicle treated group (n=15, * $P<0.05$). By contrast, in the G-2MePE study, animals treated with vehicle had an area of infarct of 43.2±6.0 mm² (n=13, FIG. 18). Treatment with G-2MePE (0.3 mg/kg/h) significantly reduced the area of the infarct to 24.0±7.0 mm² as opposed to its vehicle treated group (n=14, * $P<0.05$).

GFAP Immunostaining

Figure 19:
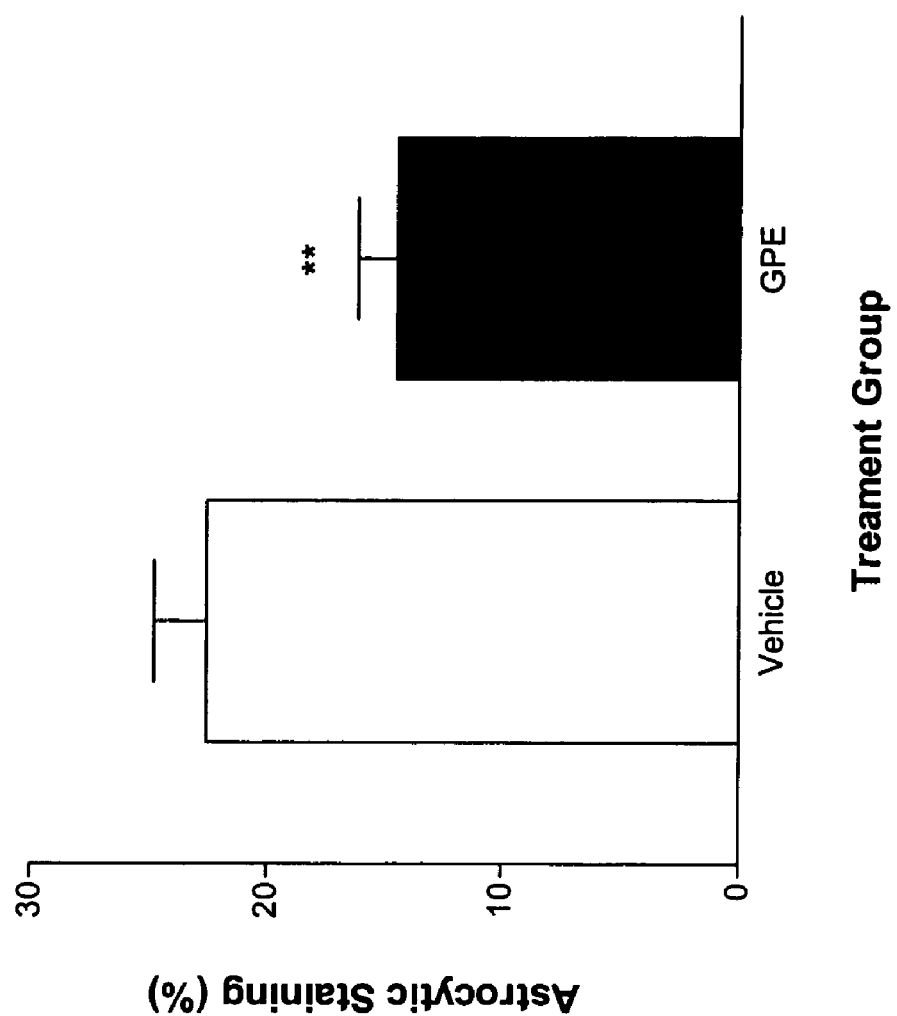
FIG. 19 shows the effect of delayed administration of GPE or vehicle treatment on GFAP staining (as a percentage) following an Et-1 MCAO model. Five hours post Et-1 injection, GPE-treated (3 mg/kg/h) (■, n=10) or vehicle-treated (succinate buffer) (□, n=10) animals were continuously infused i.v. via the jugular vein at 0.5 ml/h for four hours. Data are presented as mean±S.E.M. and significance was defined at $p<0.01$.
Figure 20:
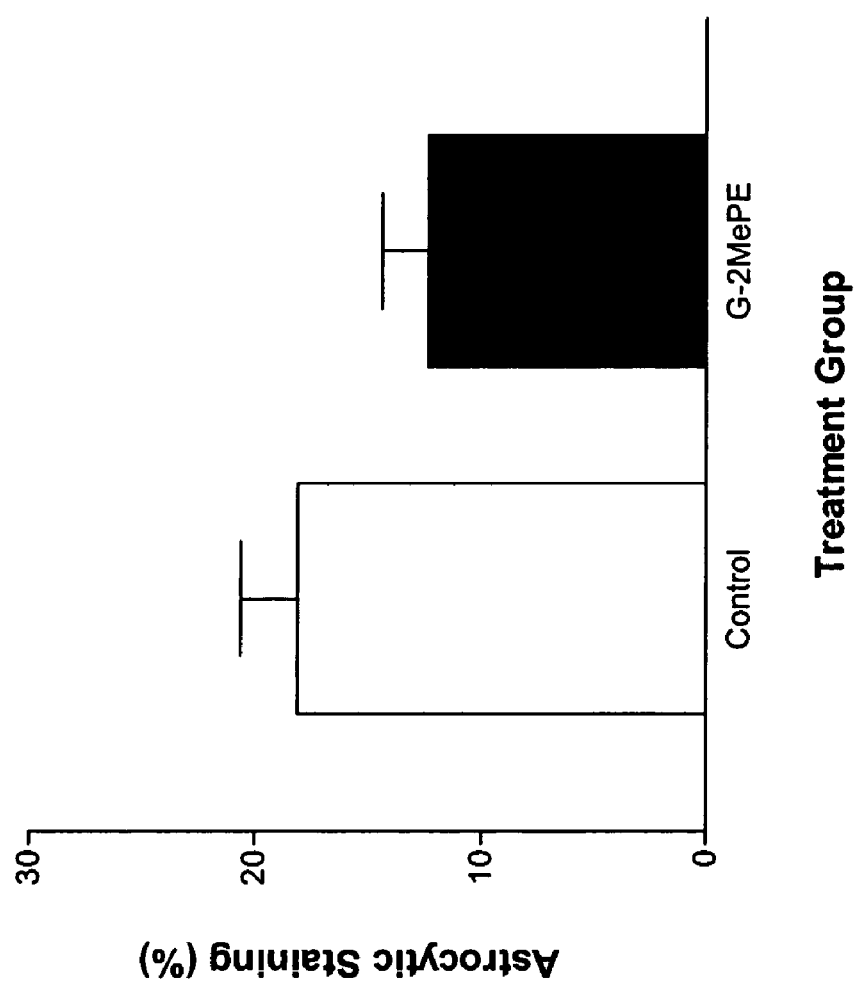
FIG. 20 shows the effect of delayed administration of G-2MePE or vehicle treatment on GFAP staining (as a percentage) following an Et-1 MCAO model. Five hours post Et-1 injection, G-2MePE -treated (0.3 mg/kg/h) (■, n=10) or vehicle-treated (succinate buffer) (□, n=10) animals were continuously infused i.v. via the jugular vein at 0.5 ml/h for four hours. Data are presented as mean±S.E.M.

The astrocytic (GFAP positive cells) response following Et-1 induced MCA occlusion was determined in both studies. There was a significant reduction in the area of GFAP immunostaining after GPE treatment (14.5±1.7%, n=10,  $P<0.01$) when compared with to its vehicle treated group (22.5±2.2%, n=10, FIG. 19). However, treatment with G-2MePE revealed only a strong inhibitory trend in GFAP immunostaining as opposed to its vehicle treated group (12.4±2.0% vs. 18.1±2.5% for the control group, n=10, FIG. 20**).

Microglia Immunostaining

Figure 21:
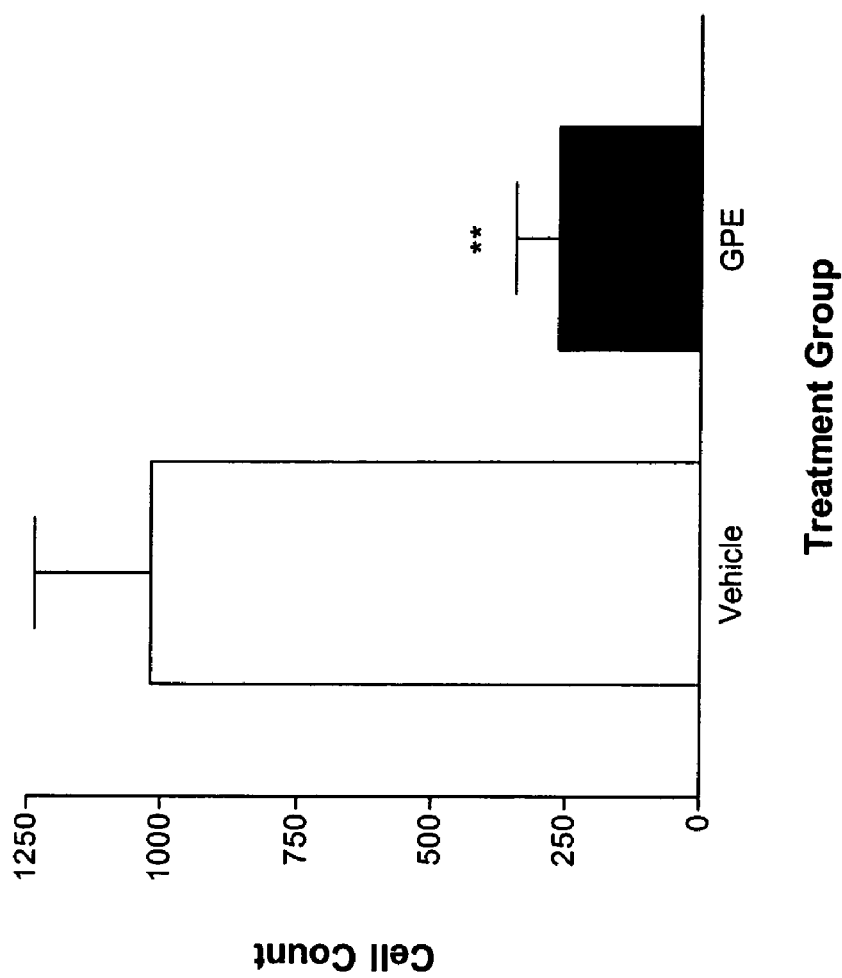
FIG. 21 shows the effect of delayed administration of GPE or vehicle treatment on microglial activation (cell count) following an Et-1 MCAO model. Five hours post Et-1 injection, GPE-treated (3 mg/kg/h) (■, n=10) or vehicle-treated (succinate buffer) (□, n=10) animals were continuously infused i.v. via the jugular vein at 0.5 ml/h for four hours. Data are presented as mean±S.E.M. and significance was defined at $p<0.01$.
Figure 22:
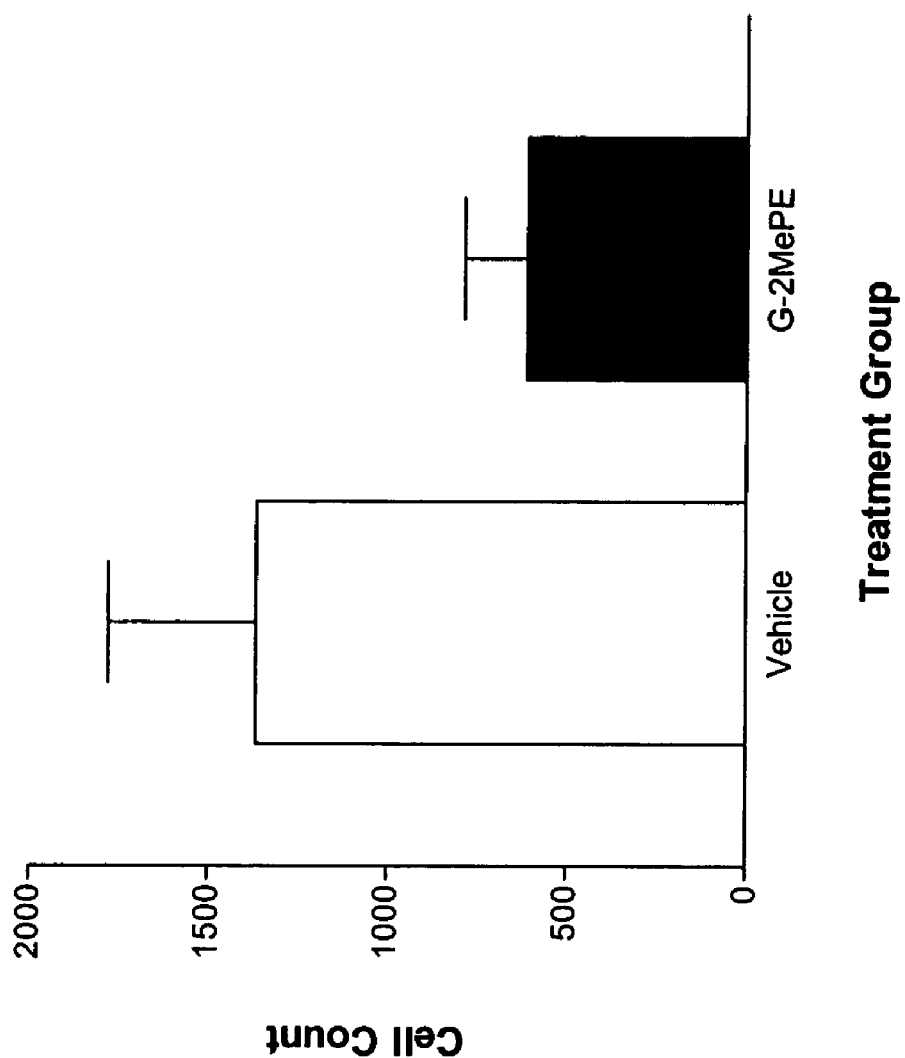
FIG. 22 shows the effect of delayed administration of G-2MePE or vehicle treatment on microglial activation (cell count) following an Et-1 MCAO model. Five hours post Et-1 injection, G-2MePE -treated (0.3 mg/kg/h) (■, n=10) or vehicle-treated (succinate buffer) (□, n=10) animals were continuously infused i.v. via the jugular vein at 0.5 ml/h for four hours. Data are presented as mean±S.E.M.

The response of microglia (isolectin $B_4$ positive cells) was investigated. The number of microglial immunopositive cells showed a significant ( $P<0.01$) decrease (264±81 vs. 1019±217 for the vehicle treated group) after GPE treatment (n=10, FIG. 21). G-2MePE treated animals (n=10, FIG. 22**) also showed a reduction in the number of microglial immunopositive cells as opposed to the vehicle treated group (612.2±174.6 vs. 1367±409.0 for the vehicle group) although this difference did not reach statistical significance.

Conclusions

GPE and G-2MePE exhibited strong neuroprotective actions following continuous i.v. infusion in adult male rats subsequent to an Et-1 induced MCA occlusion in a model of cerebral ischaemia. Interestingly, the neuroprotective effects of both these compounds were evident when administered at a time point of 5-9 h after focal cerebral ischaemia demonstrating a wide window of therapeutic opportunity. These neuroprotective effects may be related to an inhibition of both astrocytic and microglial activation following cerebral ischaemia. We conclude from these studies that both GPE and G-2MePE can be effective therapeutic agents useful in treating animals with middle cerebral artery occlusion. We further conclude that because the effects were observed in an animal system in vivo, in an art-recognized animal system that is predictive of effects in humans with stroke, that both GPE and G-2MePE can be effective in treating humans with stroke or other hypoxic or ischemic injury of the brain.

Example 6

Neuroprotective Effects G-2MePE in a Penetrating Ballistic Brain Injury

To determine whether G-2MePE might be a useful therapeutic agent in treating brain injury, we carried out a series of studies in rats that had received penetrating ballistic brain injury (PBBI) that mimics the types of injuries experienced by humans. In particular, behavioural tests of rats subjected to PBBI are useful in determining neurological deficits that commonly occur with such injuries.

Introduction

The rat penetrating ballistic brain injury (PBBI) paradigm models head injury caused by a high-energy bullet wound. It is a severe model of traumatic brain injury and has been characterised by using neurological, physiological and histopathological outcomes (Williams et al. Journal of Neurotrauma. 2005: 22(2); pp. 314-332.)), herein expressly incorporated fully by reference. G-2MePE was evaluated in the PBBI model to investigate its effect on post-injury locomotor skills, defined by the competence of post-injury rats to traverse an elevated walking beam.

PBBI Method

Sprague-Dawley rats were anaesthetised (induced with 5% isoflurane, maintained with 2% isoflurane) for surgery and placed in a stereotaxic device to enable an accurate and reproducible injury. A small burr hole was drilled in the skull to expose the right frontal pole (+4.5 mm AP, +2 mm medial; relative to Bregma) and additional bone was removed 1 mm anterior to the burr hole to enable insertion of the PBBI probe. The probe was mounted to the arm of the stereotaxic frame, at 50° from vertical and 25° counter-clockwise from the midline.

The PBBI insult in this paradigm is designed to model the immediate tract caused by a 7.62 mm high velocity round, as well as the cavity that forms in the tract by energy dissipation from the missile. To achieve this, the probe was lowered to 12 mm depth from dura and the balloon that covers the probe expanded with a sudden inflation of air to create the cavity injury. The inflation/deflation lasts no more than 10-20 ms. After induction of the injury the probe was removed and the skull resealed with bone wax, and the scalp wound sutured.

Thirty minutes following injury, rats were given either saline control or G-2MePE (0.3 and 3.0 mg/kg/h) delivered by intravenous infusion for 4 or 12 hours.

Rats were allowed a recovery period of either 24 hours or 72 hours post surgery prior to behavioural testing. For behavioural testing rats were placed on an elevated walking beam, and their capacity to traverse the beam was assessed. Automatic tracking of foot-faults occurring when the rats walked along the beam were recorded. In addition, rats were scored for severity of clinical signs (neurobehavioural dysfunction) and post-mortem for injury size following the PBBI (H&E staining) and activated microglia cell counts (OX-18 staining)

Results

The effects of G-2MePE administered i.v. for 4 h (0, 0.3, 3 mg/kg/h) on foot-faults and neurological disability score were tested either 24 h or 72 h following PBBI.

Figure 23A:
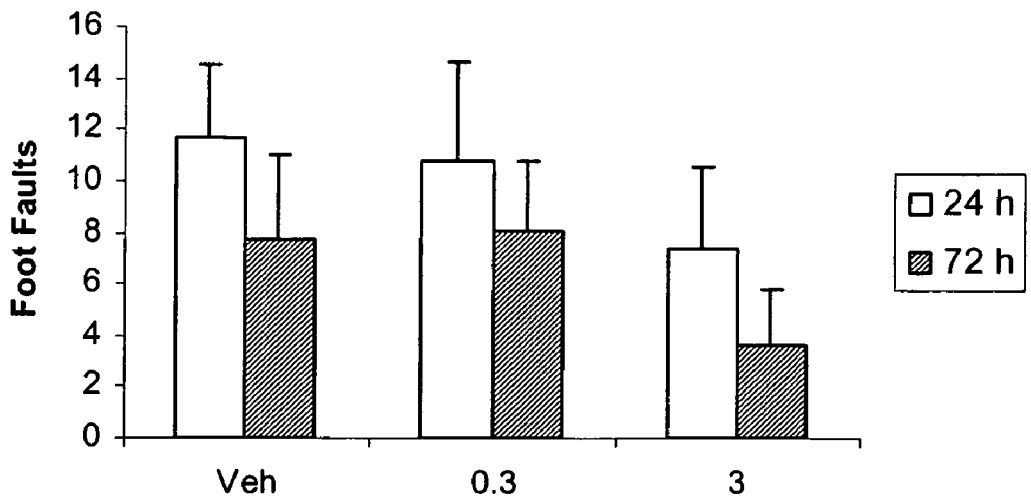
FIG. 23 shows the effect of G-2MePE administered i.v. (0, 0.3, 3 mg/kg/h) on foot-faults (FIG. 23A) and neurological disability score (FIG. 23B), tested either 24 h or 72 h following penetrating ballistic brain injury (PBBI).
Figure 23B:
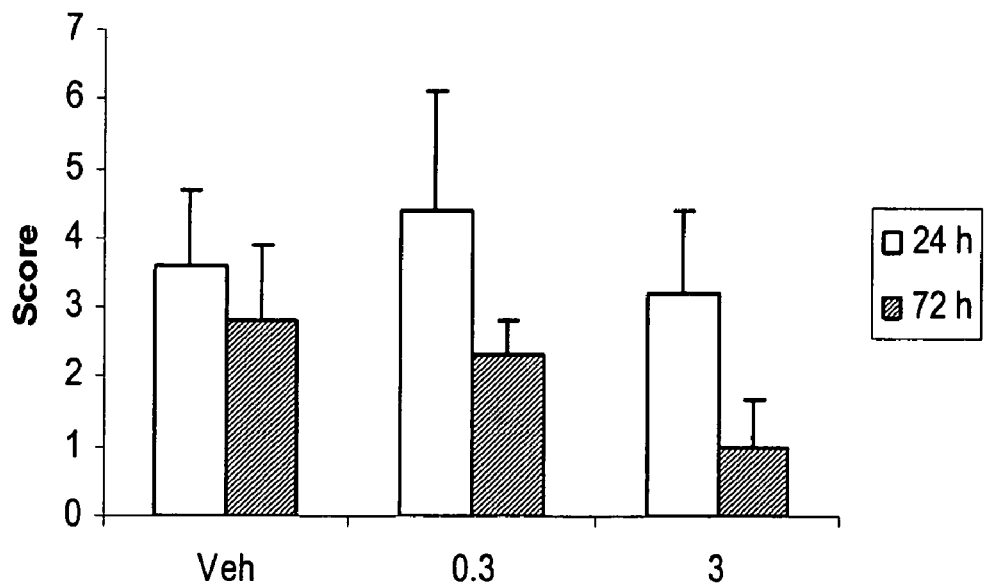

Foot-fault count was 54% lower and neurological disability score was 69% lower, in rats administered 3 mg/kg/h G-2MePE when tested 72 h post-injury (FIGS. 23A and 23B respectively).

Figure 24:
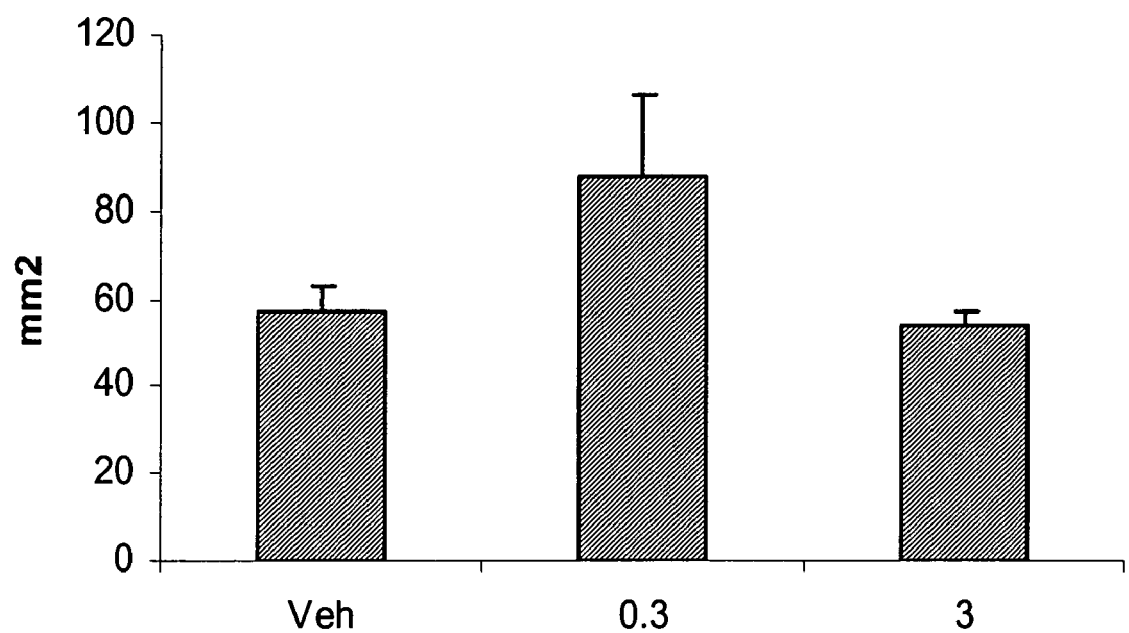
FIG. 24 shows the effect of G-2MePE administered i.v. (0, 0.3, 3 mg/kg/h) on total injury volume to the brain assessed post-mortem following PBBI insult.

No significant effect of G-2MePE administered i.v. (0, 0.3, 3 mg/kg/h) on total injury volume to the brain assessed post-mortem following PBBI insult was observed (FIG. 24).

Figure 25:
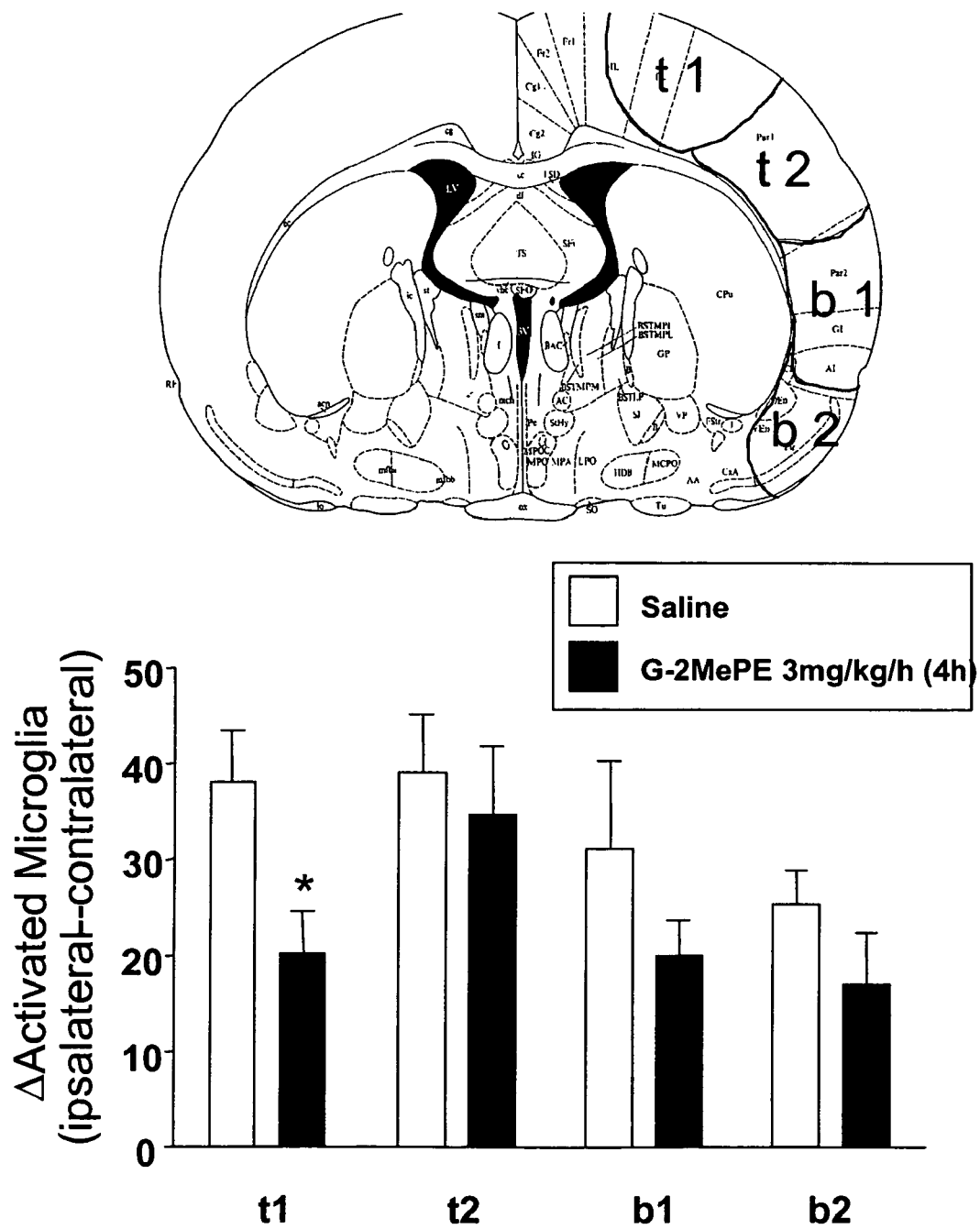
FIG. 25 shows the effect of G-2MePE (administered i.v; 3.0 mg/kg/h; 4 h infusion) 30 min post-PBBI on the activation of microglia, measured by OX-18 staining.

The effect of G-2MePE (3.0 mg/kg/h; administered i.v. as a 4 h infusion commencing 30 min post-PBBI) on the activation of microglia were, measured by OX-18 staining (FIG. 25). Microglia activation in area t1 was significantly reduced in the G-2MePE-treated group, and in areas t2, b1 and b2 a marked trend towards reduction of microglial activation was observed in all G-2MePE treated groups.

Experiment 2

In experiment 2 Rats were given either saline control or G-2MePE for 12 hours at either 1.0 or 3.0 mg/kg/h, with infusion initiated 30 min post-PBBI insult.

Results

Figure 26A:
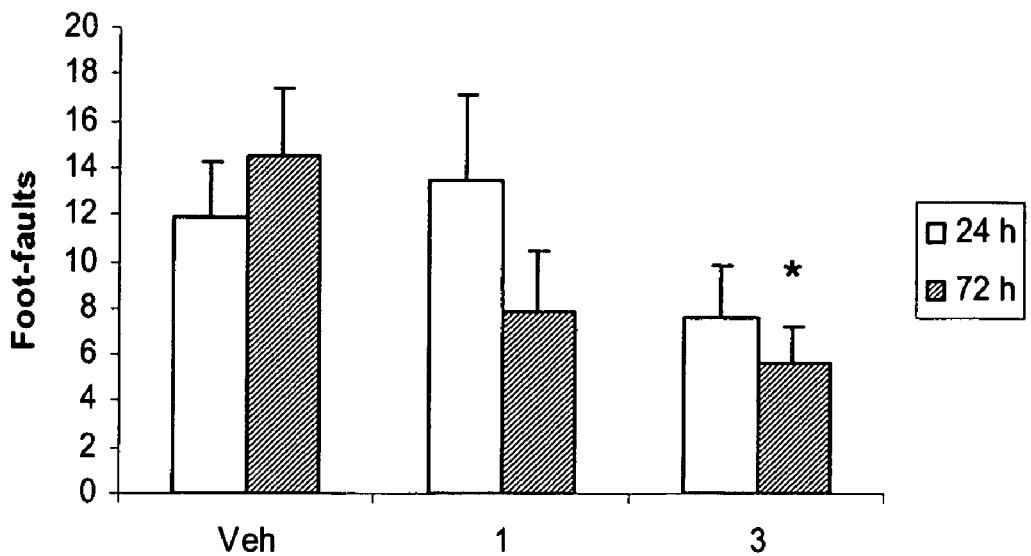
FIG. 26 shows the efficacy of G-2MePE administered for 12 hours post-trauma on beam-walking performance (FIG. 26A) and neurological disability score (FIG. 26B).
Figure 26B:
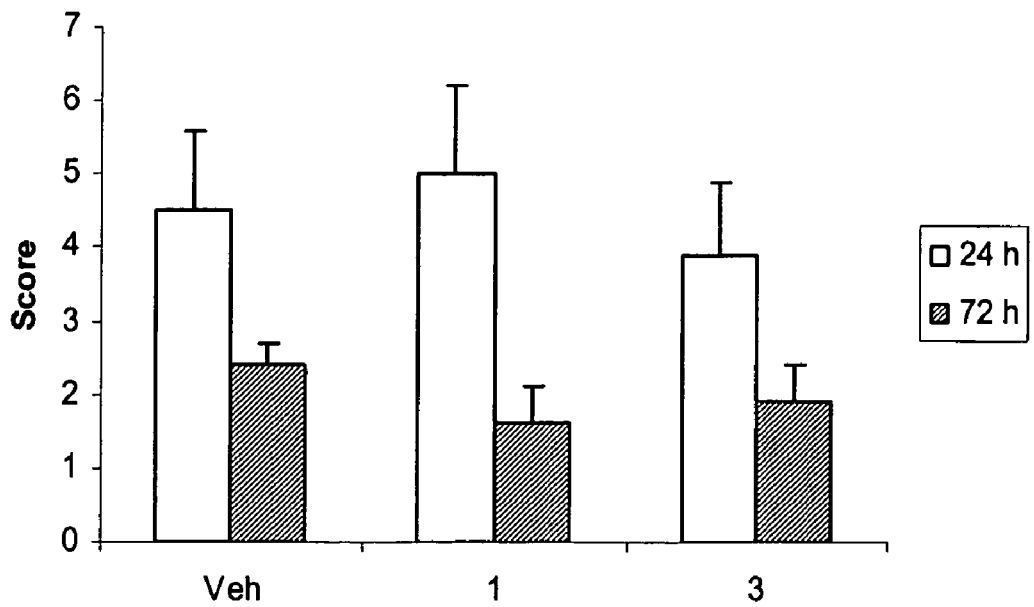

At a dose of 3 mg/kg/h G-2MePE significantly reduced foot-fault count measured at 72 h post surgery (* p<0.01, ANOVA with Bonferroni post-hoc test) (FIG. 26A). No statistically significant effects on neurological score (FIG. 26B) or injury size (data not shown) were observed.

Conclusion

We conclude from these studies that G-2MePE is effective in reducing behavioural disorders associated with neural injury. Because the studies were in vivo studies in an art-recognized animal system for study of brain injury, these results are predictive of effects observed in humans with similar types of injuries. Therefore, we conclude that G-2MePE can be an effective therapeutic agent in treating people with penetrating brain injuries.

Example 7

Prophylactic Effects of G-2MePE in a Model of Multiple Sclerosis

To determine whether G-2MePE might be a suitable therapy for multiple sclerosis (MS), we studied an art-recognized system that mimics MS in humans. Experimental autoimmune encephalomyelitis (EAE) is well recognized as exhibiting many of the neurological and behavioural deficits that commonly occur in humans suffering from MS. Therefore, studies of mice in vivo of EAE are relevant to human MS. Further, effects of therapeutic agents on EAE in rats can be highly probative of such effects in humans suffering from MS.

Materials and Methods

Animals

Female mice, 6-8 weeks old, strain C57B1/6J weighing an average of 24 g each were used.

Induction of EAE

A 200 ul volume of an emulsion containing 200 ug of the encephalitogenic peptide MOG35-55 (MEVGWYRSPFS-RVVHLYRNGK; SEQ ID NO:1) was obtained from C S Bio Co. USA in complete Freund adjuvant (Difco, Detroit, USA) containing 800 ug *Mycobacterium tuberculosis* (Difco, Detroit, USA). The formulation was injected subcutaneously into one flank. Mice were immediately injected intraperitoneally with 400 ng pertussis toxin (List Biological Laboratories, USA) and again 48 hours later. Animals were then divided into 2 treatment groups, vehicle (n=7 in Experiment 1; n=8 in Experiment 2) and G-2MePE (n=7 in Experiment 1; n=7 in Experiment 2).

Treatment

Mice in a G-2MePE-treated group were injected with 5 ug per day of G-2MePE intraperitoneally for 14 consecutive days commencing on day 5 after the encephalitogenic challenge with MOG35-55.

Assessment of Neurological Impairment

Mice were monitored daily and neurological impairment was scored on an arbitrary clinical score as follows: 0, no clinical sign; 1, flaccid tail; 2, hind limb weakness; 3, hind limb paralysis; 4, hind limb weakness and fore limb weakness; 5, paraplegia; 6, death. These measures are recognized in the art as indicatinve of neurological impairment in animals including humans. Therefore, studies of neurological impairment using these methods is predictive of neurological impairment in humans, and that therapeutic effects observed in animals using this test are predictive of therapeutic effects in human beings suffering from neurological impairment.

Results

In animals with EAE, disease typically develops from 10 days following the immunization with MOG. Intraperitoneal injection started on day 5 after immunization with MOG and continued until day 18.

Figure 27A:
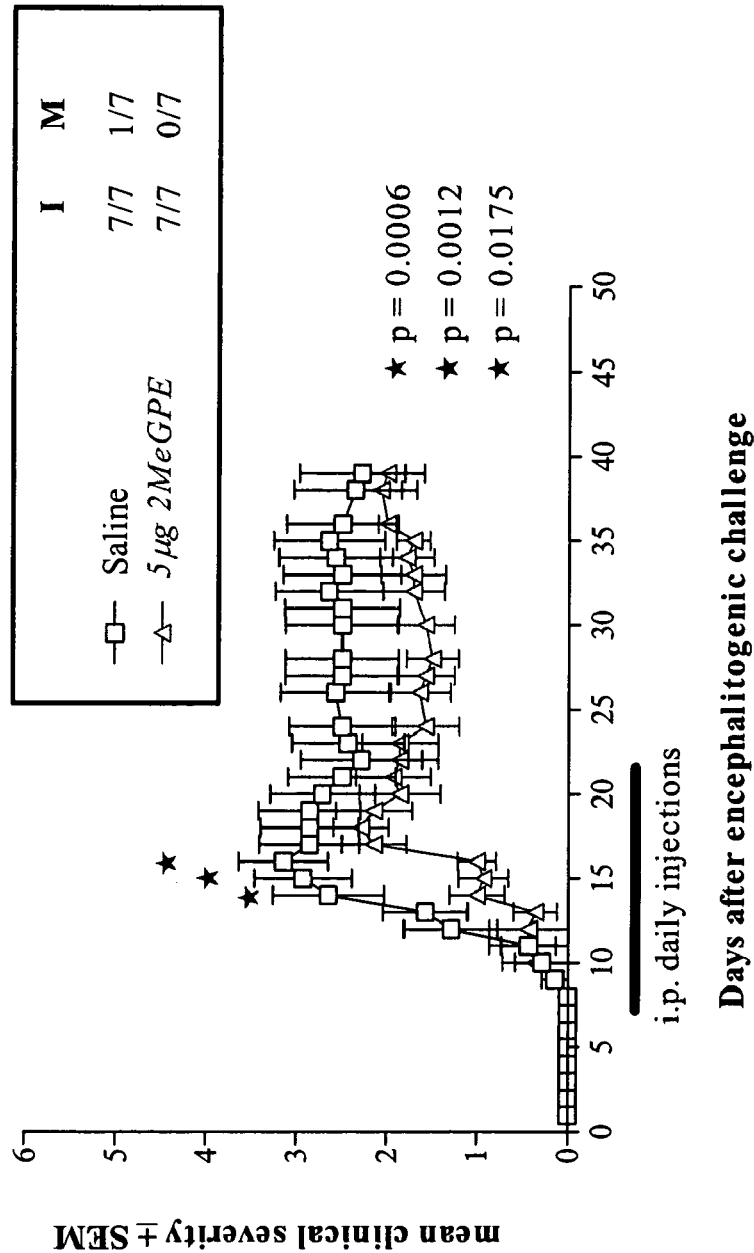
FIGS. 27A and 27B show the effects of G-2MePE (5 μg; administered daily i.p. for 14 days) in a chronic progressive EAE mouse model. I=disease incidence; M=mortality rate.
Figure 27B:
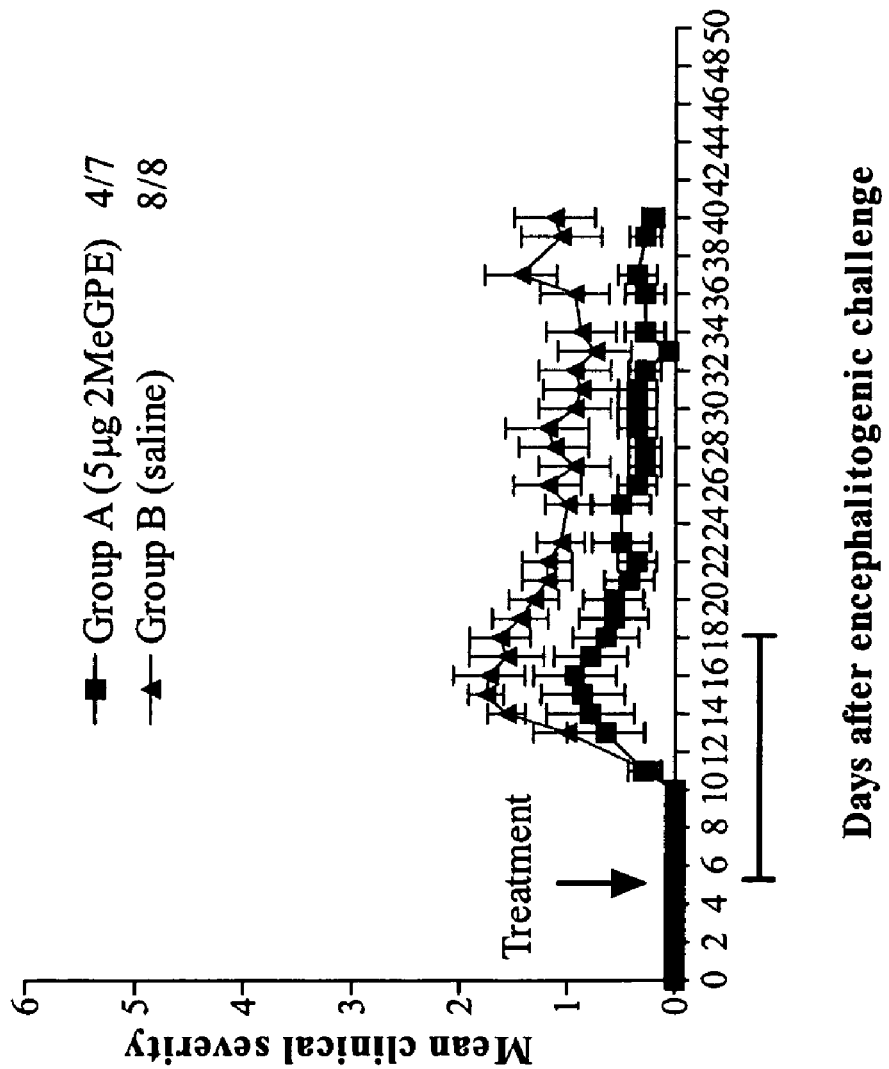

FIGS. 27A and 27B depict results of studies comparing effects of G-2MePE on EAE in mice in two Experiments. FIG. 27A depicts a graph showing the efficacy of G-2MePE in attenuating development of motor symptoms of EAE following immunization with MOG (as can be seen from day 13-15). At three time points, comparison of G-2MePE-treated and vehicle-treated animals was statistically significant, with p values of less than 0.02 in each case. For the remainder of the study, the G-2MePE-treated animals exhibited a lower mean clinical severity score than the vehicle-treated animals. "I" stands for induction of the disease and "M" stands for mortality. In the control group as well as in the G-2MePE-treated group, all 7 of 7 animals developed clinical symptoms of disease, as reflected in the increased clinical score. None of the animals in the G-2MePE group died, and 1 animal in the vehicle-treated group died.

FIG. 27B depicts results showing the efficacy of G-2MePE in attenuating the development of motor symptoms of EAE. All 8 of the 8 animals in the vehicle-treated group developed symptoms of EAE, whereas only 4 of the 7 animals in the G-2MePE-treated group developed symptoms of EAE. No animals died as a result of development of EAE in either group.

In Experiment 1 from day 13 to 15, the animals treated with G-2MePE exhibited significant attenuation of the disease profile (e.g., recovery of motor deficits) compared to the control group treated with saline only.

We conclude that G-2MePE can be useful in treating motor deficits caused by autoimmune disorders of the brain, and therefore can be useful in treating multiple sclerosis in human beings.

Example 8

Comparison of the Pharmacokinetics of GPE and G-2MePE

The purpose of these studies was to compare pharmacokinetic profiles of GPE and G-2MePE in animals in vivo using standard pharmacokinetic methods.

Methods

Adult male Wistar rats weighing between 180 and 240 g were used to determine the pharmacokinetics of GPE and G2MePE. To facilitate intravenous bolus injections and blood sampling, all rats were surgically implanted with an indwelling jugular venous cannula under halothane anesthesia three days before the experiment. Groups of six rats were given a single intravenous bolus injection of either 30 mg/kg GPE or 10 mg/kg G2MePE dissolved in 0.1M succinate buffer (pH 6.5). Blood samples (about 220 µl each) were collected into heparinized tubes containing Sigma protease inhibitor cocktail for mammalian tissues at 10 and 0 min before injection of either GPE or G2MePE, and 1, 2, 4, 8, 16, 32, 64 and 128 min after injection of either GPE or G2MePE. The samples were centrifuged at 3000 g for 15 min at 4° C. and the plasma removed and stored at −80° C. until extraction and assay by either radioimmunoassay ("RIA") or reverse phase HPLC. The RIA and HPLC methods used were conventional.

Drug elimination after a single intravenous bolus injection was found to be a first-order process following the equation $C=C_0 e^{-kt}$, where C represents drug concentration in any time point, $C_0$ is the concentration when time (t) equals zero and k is the first-order rate constant expressed in units of concentration per hour. The k and half-life ($t_{1/2}$) were calculated from the slope of the linear regression line in the elimination phase of the semi-logarithmic plot of plasma concentration versus time as: Log $C=-kt/2.3+\log C_0$. Results were expressed as mean±standard error.

Results

Figure 28:
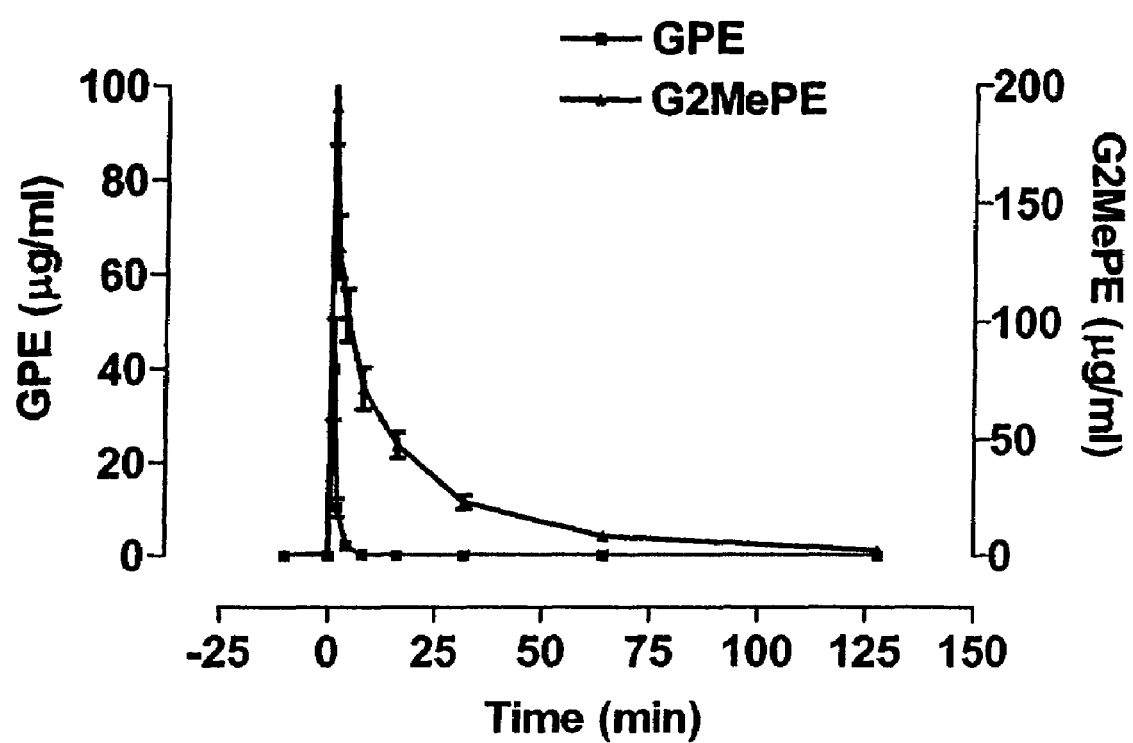
FIG. 28 shows a graph of the plasma concentration of GPE and G-2MePE after intravenous injection.

FIG. 28 shows a graph of plasma concentrations in vivo of GPE and G-2MePE after intravenous (i.v.) injection. Filled squares represent concentrations of GPE at each time point, and filled triangles represent concentrations of G-2MePE at each time point.

Plasma concentrations of GPE and G-2MePE were markedly increased within 1 min after injection. After injection of 30 mg/kg GPE, a peak concentration of 40.0±10.8 mg/ml was observed. Plasma concentrations of GPE then rapidly declined according to a first-order kinetic process. The first order rate constant for GPE was found to be 0.15±0.014 ng/ml/min, the $t_{1/2}$ was found to be 4.95±0.43 min and the estimated clearance of GPE from plasma was found to be 137.5±12.3 ml/hr.

After injection of 10 mg/kg G-2MePE, the peak concentration was found to be 191±16.1 mg/ml. Plasma concentrations of G-2MePE then declined according to a first-order kinetic process. The first order rate constant for G-2MePE was found to be 0.033±0.001 ng/ml/min, the $t_{1/2}$ was found to be 20.7±0.35 min and the estimated clearance was found to be 30.1±0.5 ml/hr.

After injection, the maximal plasma concentration of G-2MePE was about 4.8 times greater than the maximal plasma concentration of GPE, in spite of the larger dose of GPE delivered (30 mg/kg) compared to the dose of G-2MePE delivered (10 mg/kg).

The finding of greater plasma concentrations of G-2MePE than for GPE at all time points less than 125 minutes, in spite of a lower delivered dose of G-2MePE was totally unexpected based on known plasma concentrations of GPE. The $t_{1/2}$ for G-2MePE was over 4 times longer than the $t_{1/2}$ for GPE.

The finding of increased half-life of G-2MePE compared to that of GPE was completely unexpected based on the $t_{1/2}$ of GPE. The increased $t_{1/2}$ of G-2MePE means that G-2MePE is cleared more slowly from the circulation. This finding is totally unexpected based on the clearance rate of GPE.

While this invention has been described in terms of certain preferred embodiments, it will be apparent to a person of ordinary skill in the art having regard to that knowledge and this disclosure that equivalents of the compound of this invention may be prepared and administered for the conditions described in this application, and all such equivalents are intended to be included within the claims of this application. Unless specified with particularity in the foregoing descriptions, each and every reference and publication cited herein is explicitly incorporated fully by reference, as though it had been separately so incorpoarated.

The invention claimed is:

1. A method of treating an animal having a neurological injury caused by traumatic brain injury, comprising administration to an animal in need thereof a therapeutically effective amount of glycyl-L-2-methyl prolyl-L-glutamic acid (G-2MePE) to provide relief from a symptom of said traumatic brain injury.

2. The method of claim 1 where said traumatic brain injury causes stroke.

3. The method of claim 1 where said injury is penetrating brain injury.

4. The method of claim 1 where said traumatic brain injury causes hypoxia of the brain.

5. The method of claim 1 where said traumatic brain injury causes ischemia of the brain.

6. The method of claim 1 where at least one other anti-apoptotic or neuroprotective agent is administered.

7. The method of claim 1, where said traumatic brain injury is characterized by loss of neural cells from said animal's brain.

8. The method of claim 1, where said symptom of traumatic brain injury is a seizure.

9. The method of claim 1, where said symptom of traumatic brain injury is a motor disorder.

10. The method of claim 9, where said motor disorder is a disorder of gait.

11. The method of claim 1, where said traumatic brain injury causes injury to cortical cells, striatal cells, or cerebellar cells.

12. The method of claim 1, where said condition or injury is characterized by an increase astrocytic or microglial cell activation within the said animal's brain.

13. A method for reducing a seizure induced by traumatic brain injury comprising administering to an animal in need thereof a pharmacologically effective amount of G-2MePE.

* * * * *

UNITED STATES PATENT AND TRADEMARK OFFICE
CERTIFICATE OF CORRECTION

PATENT NO. : 7,605,177 B2
APPLICATION NO. : 11/314424
DATED : October 20, 2009
INVENTOR(S) : Gluckman et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 419 days.

Signed and Sealed this

Fifth Day of October, 2010

David J. Kappos
*Director of the United States Patent and Trademark Office*